(12) United States Patent
Rosenthal

(10) Patent No.: US 6,566,091 B1
(45) Date of Patent: *May 20, 2003

(54) NEUROTROPHIC FACTOR

(75) Inventor: Arnon Rosenthal, Pacifica, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/451,390

(22) Filed: May 26, 1995

Related U.S. Application Data

(60) Division of application No. 08/426,419, filed on Apr. 19, 1995, now abandoned, which is a continuation of application No. 08/030,013, filed as application No. PCT/US91/06950 on Sep. 24, 1991, now abandoned, application No. 08/451,390, which is a continuation-in-part of application No. 07/648,482, filed on Jan. 31, 1991, now abandoned, which is a continuation-in-part of application No. 07/587,707, filed on Sep. 25, 1990, now Pat. No. 5,364,769.

(51) Int. Cl.$^7$ .............................. C12N 15/12; C12N 5/00
(52) U.S. Cl. ......................... 435/69.1; 435/6; 435/69.4; 435/320.1; 435/325; 536/23.5; 536/23.51
(58) Field of Search ............................ 536/23.5, 23.51; 435/6, 69.1, 69.4, 320.1, 240.1, 252.3, 325

(56) References Cited

U.S. PATENT DOCUMENTS

| | | | |
|---|---|---|---|
| 4,699,875 A | 10/1987 | Appel | |
| 4,997,929 A | 3/1991 | Collins et al. | |
| 5,169,764 A | * 12/1992 | Shooter et al. | 435/69.7 |

FOREIGN PATENT DOCUMENTS

| | | | |
|---|---|---|---|
| DE | 3113963 | 10/1983 | |
| WO | WO 93/25684 | 12/1993 | C12N/5/12 |

OTHER PUBLICATIONS

Ip., N. et al., *PNAS*, 89:3060–3064, Apr. 1992.*
Barde et al., "Purification of a New Neurotrophic Factor From Mammalian Brain" *EMBO Journal* 1(5):549–553 (1982).
Barde, Y. A., "Trophic Factors and Neuronal Survival" *Neuron.* 2:1525–1534 (1989).
Barinaga *Science* 264:772–774 (1994).
Berkemeier et al., "Neurotrophin–5: A Novel Neurotrophic Factor That Activates trk and trkB" *Neuron* 7:857–866 (Nov. 1991).
Coughlin et al., "NGF–Independent Development of Embryonic Mouse Sympathetic Neurons in Dissociated Cell Culture" *Dev. Biol.* 110:392–401 (1985).
Hallbook et al., "Evolutionary Studies of the Nerve Growth Factor Family Reveal a Novel Member Abundantly Expressed in Xenopus Ovary" *Neuron* 6:845–858 (May 1991).
Hefti, Franz, "Nerve Growth Factor Promotes Survival of Septal Cholinergic Neurons after Fimbrial Transections" *J. of Neuroscience* 6 (8): 2155–2162 (Aug. 1986).
Hohn et al., "Identification and Characterization of a novel member of the nerve growth factor/brain–derived neurotrophic factor family" *Nature* 344:339–341 (Mar. 22, 1990).
Ibanez et al., "Structure–Function Studies of Nerve Growth Factor: Functional Importance of Highly Conserved Amino Acid Residues" *EMBO Journal* 9 (5): 1477–1483 (1990).
Johnson et al., "The Role of NGF in Sensory Neurons in Vivo" *Trends in NeuroScience* pp. 33–37 (1986).
Korsching et al., "Nerve Growth Factor in Sympathetic Ganglia and Corresoponding Target Organs of the Rat: Correlation with Density of Sympathetic Innervation" *Proc. Natl. Acad. Sci. USA* 80:3513–3516 (1983).
Leibrock et al., "Molecular cloning and expression of brain–derived neurotrophic factor" *Nature* 341:149–152 (Sep. 14, 1989).
Levi–Montalcini et al., "Selective Growth Stimulating Effects of Mouse Sarcoma on the Sensory and Sympathetic Nervous System of the Chick Embryo" *J. Exp. Zool* 116:321–361 (1951).
Lin et al., "Purification, Cloning, and Expression of Ciliary Neurotrophic Factor (CNTF)" *Science* 246:1023–1025 (1989).
Lindsay et al., "Placode and Neural Crest–Derived Sensory Neurons are Responsive at Early Development Stages to Brain–Derived Neurotrophic Factor" *Dev. Bio.* 112:319–328 (1985).
Maisonpierre et al., "Neurotrophin–3: A Neurotrophic Factor Related to NGF and BDNF" *Science* 247:1446–1451 (Mar. 23, 1990).
Oppenheim et al., "Cell Death of Motoneurons in the Chick Embryo Spinal Cord. VI Reduction of Naturally Occurring Cell Death in the Thoracolumbar Column of Terni by Nerve Growth Factor" *J. Comparative Neur.* 210:174–189 (1989).
Rosenthal et al., "Primary Structure and Biological Activity of a Novel Human Neurotrophic Factor" *Neuron* 4:767–773 (May 1990).

(List continued on next page.)

Primary Examiner—Marianne P. Allen
(74) Attorney, Agent, or Firm—Ginger R. Dreger, Esq.; Heller Ehrman White & McAuliffe, LLP

(57) ABSTRACT

A novel polypeptide, designated neurotrophic factor-4 (NT-4), has been identified by PCR amplification of human genomic DNA. Provided herein is nucleic acid encoding NT-4 useful in diagnostics and in the recombinant preparation of NT-4. Also provided herein are nucleic acids encoding naturally occurring amino acid sequence variants of NT-4, designated NT-4β, NT-4γ, and NT-4Δ. The neurotropic factors of the invention are useful in the treatment of nerve cells and in diagnostic assays.

29 Claims, 6 Drawing Sheets

OTHER PUBLICATIONS

Shelton et al., "Expression of the β–nerve growth factor gene correlates with the density of sympathetic innervation in effector organs" *Proc. Natl. Acad. Sci. USA* 81: 7951–7955 (Dec. 1984).

Thoenen et al., "The Physiological Function of Nerve Growth Factor in the Central Nervous System: Comparison With the Periphery" *Rev. Physiol. Biochem. Pharmacol.* 109:146–178 (1987).

Tiercy et al., "Early changes in the Synthesis of Nuclear and Cytoplasmic Proteins Are Induced by Nerve Growth Factor in Differentiating Rat PC12 Cells" *Journal of Cell Biology* 103(6):2367–2378 (Dec. 1986).

Wion et al., "Molecular Cloning of the Avian β–Nerve Growth Factor Gene: Transcription in Bran" *FEBS Letters* 203(1):82–86 (1986).

* cited by examiner

```
ATG CTC CCT CTC CCC TCA TGC TCC CTC CCC ATC CTC CTC CTT TTC
Met Leu Pro Leu Pro Ser Cys Ser Leu Pro Ile Leu Leu Leu Phe

CTC CTC CCC AGT GTG CCA ATT GAG TCC CAA CCC CCA CCC TCA ACA TTG
Leu Leu Pro Ser Val Pro Ile Glu Ser Gln Pro Pro Pro Ser Thr Leu

CCC CCT TTT CTG GCC CCT GAG TGG GAC CTT CTC TCC CCC CGA GTA GTC
Pro Pro Phe Leu Ala Pro Glu Trp Asp Leu Leu Ser Pro Arg Val Val
                                                  *

CTG TCT AGG GGT GCC CCT GCT GGG CCC CCT CTG CTC TTC CTG CTG GAG
Leu Ser Arg Gly Ala Pro Ala Gly Pro Pro Leu Leu Phe Leu Leu Glu

GCT GGG GCC TTT CGG GAG TCA GCA GGT GCC CCG GCC AAC CGC AGC CGG
Ala Gly Ala Phe Arg Glu Ser Ala Gly Ala Pro Ala Asn Arg Ser Arg
            ↓

CGT GGG GTG AGC GAA ACT GCA CCA GCG AGT CGT CGG GGT GAG CTG GCT
Arg Gly Val Ser Glu Thr Ala Pro Ala Ser Arg Arg Gly Glu Leu Ala
 1                                          10

GTG TGC GAT GCA GTC AGT GGC TGG GTG ACA GAC CGC CGG ACC GCT GTG
Val Cys Asp Ala Val Ser Gly Trp Val Thr Asp Arg Arg Thr Ala Val
             20                                           30

GAC TTG CGT GGG CGC GAG GTG GAG GTG TTG GGC GAG GTG CCT GCA GCT
Asp Leu Arg Gly Arg Glu Val Glu Val Leu Gly Glu Val Pro Ala Ala
                             40

GGC GGC AGT CCC CTC CGC CAG TAC TTC TTT GAA ACC CGC TGC AAG GCT
Gly Gly Ser Pro Leu Arg Gln Tyr Phe Phe Glu Thr Arg Cys Lys Ala
             50                                     60

GAT AAC GCT GAG GAA GGT GGC CCG GGG GCA GGT GGA GGG GGC TGC CGG
Asp Asn Ala Glu Glu Gly Gly Pro Gly Ala Gly Gly Gly Gly Cys Arg
                         70

GGA GTG GAC AGG AGG CAC TGG GTA TCT GAG TGC AAG GCC AAG CAG TCC
Gly Val Asp Arg Arg His Trp Val Ser Glu Cys Lys Ala Lys Gln Ser
80                                       90

TAT GTG CGG GCA TTG ACC GCT GAT GCC CAG GGC CGT GTG GGC TGG CGA
Tyr Val Arg Ala Leu Thr Ala Asp Ala Gln Gly Arg Val Gly Trp Arg
                 100                                      110

TGG ATT CGA ATT GAC ACT GCC TGC GTC TGC ACA CTC CTC AGC CGG ACT
Trp Ile Arg Ile Asp Thr Ala Cys Val Cys Thr Leu Leu Ser Arg Thr
                             120

GGC CGG GCC TGA G
Gly Arg Ala OP*
        130
```

```
  1 C   GAG AGA TGC TCT GAG AGA TGC TCC CAC TCC CCC AGG CTC CCT CCG
  1       Glu Arg Cys Ser Glu Arg Cys Ser His Ser Pro Arg Leu Pro Pro

47 CAT CCC CCT CAT TTT CCT CCT CCC CAG TGT GTC AAT GGA GTC CTA ACC
 16 His Pro Pro His Phe Pro Pro Pro Gln Cys Val Asn Gly Val Leu Thr

95 CCA TCC TCG ACA TTG TCG CCT TTT CCT CCT CCA GAG TGG GAC CTT CTT
 32 Pro Ser Ser Thr Leu Ser Pro Phe Pro Pro Pro Glu Trp Asp Leu Leu

143 TTC CCC CGA GTG GTC CTG TCT AGG GGT GCC GCT GCC GGG CCC CCT CTG
 48 Phe Pro Arg Val Val Leu Ser Arg Gly Ala Ala Ala Gly Pro Pro Leu

191 GTC TTC CTG CTG GAG ACT GGA GCC TTT CGG GAG TCA GCA GGC GCC CGG
 64 Val Phe Leu Leu Glu Thr Gly Ala Phe Arg Glu Ser Ala Gly Ala Arg

239 GCC AAC CGC AGC CAG CGA GGG GTG AGC GAT ACT TCA CCG GCG AGT CAT
 80 Ala Asn Arg Ser Gln Arg Gly Val Ser Asp Thr Ser Pro Ala Ser His

287 CAG GGT GAG CTG GCC GTG TGC GAT GCA GTC AGT GTC TGG GTG ACA GAC
 96 Gln Gly Glu Leu Ala Val Cys Asp Ala Val Ser Val Trp Val Thr Asp

335 CCC TGG ACT GCT GTG GAC TTG GGT GTG CTC GAG GTG GAG GTG TTG GGC
112 Pro Trp Thr Ala Val Asp Leu Gly Val Leu Glu Val Glu Val Leu Gly

383 GAG GTG CCT GCA GCT GTC GGC AGT TCC CTC CGC CAG CAC TTC TTT GTT
128 Glu Val Pro Ala Ala Val Gly Ser Ser Leu Arg Gln His Phe Phe Val

431 GCC CGC TTC GAG GCC GAT AAA TCT GAG GAA GGT GGC CCG GGG GTA GGT
144 Ala Arg Phe Glu Ala Asp Lys Ser Glu Glu Gly Gly Pro Gly Val Gly

479 GGA GGG GCT GCC GCC GGG GTG TGG ACC GGG GGG CAC TGG GTG TCT GAG
160 Gly Gly Ala Ala Ala Gly Val Trp Thr Gly Gly His Trp Val Ser Glu

527 TGC AAG GCC AAG CAG TCC TAT GTG CGG GCA TTG ACC GCT GAT GCC CAG
176 Cys Lys Ala Lys Gln Ser Tyr Val Arg Ala Leu Thr Ala Asp Ala Gln

575 GGC CGT GTG GAC TGG CGA TGG ATT CAA ATT GGC ACA GCC TGT GTC TGC
192 Gly Arg Val Asp Trp Arg Trp Ile Gln Ile Gly Thr Ala Cys Val Cys

623 ACA CTC CTC AGC CGG ACT GGC CGG GCC TGA   GACTTATA CCCAGGAACT
208 Thr Leu Leu Ser Arg Thr Gly Arg Ala OP*

671 GGTCAGGCAG AAAAA
```

FIG. 3

```
   1 ACTGGAGCGC AGCACCACGC CCAGCTAATT TTGGTATTAT CAGTAGAGAT GTTGTTTCAC
  61 AGTGTTGGCC AGGCTGCTCT CAAACTCCTG ACCTCAAGTC AAACACCCGC CTCAGCCTCC
 121 CAAAGTGCTG GGACTACAGG TGTGAGCCAT AGTGCCTGAC CTGTAGTTGT TGAATATTTA
 181 TTATTAATCT ACAAGTTGGG TGTGATGCAA GTCCTTTATA TGGAGTCCCC CAAACTTCTA
 241 G   AGC AAG GGC TTC CCC ATA ATC CTG GCA GGC AGG CCT CCC CTG GGG TTC
   1     Ser Lys Gly Phe Pro Ile Ile Leu Ala Gly Arg Pro Pro Leu Gly Phe

290 CCA ACT TCT GAC CCC ACT GAA GTG TTT ATC TTC TTC CCT AAT CCC AGC CTC
  17 Pro Thr Ser Asp Pro Thr Glu Val Phe Ile Phe Phe Pro Asn Pro Ser Leu

341 CTT TTC CCT GTC TCC ATG TGC TCT GAG AGA TGC TCT GAG AGA TGC TCC TGC
  34 Leu Phe Pro Val Ser Met Cys Ser Glu Arg Cys Ser Glu Arg Cys Ser Cys

392 TCC CCC AGG CTC CCT CCG CAT CCC CCT CAT TTT CCT CCT CCC CAG TGT GTC
  51 Ser Pro Arg Leu Pro Pro His Pro Pro His Phe Pro Pro Pro Gln Cys Val

443 ATT GGA GTC CTA ACC CCA TCC TCG ACA TTG TCG CGT TTT CCT CCT CCA GAG
  68 Ile Gly Val Leu Thr Pro Ser Ser Thr Leu Ser Arg Phe Pro Pro Pro Glu

494 TGG GAC CTT CTT TTC CCC CGA GTG GTC CTG TCT AGG GGT GCC GCT GCC GGG
  85 Trp Asp Leu Leu Phe Pro Arg Val Val Leu Ser Arg Gly Ala Ala Ala Gly

545 CCC CCT CTG GTC TTC CTG CTG GAG ACT GGA GCC TTT CGG GAG TCA GCA GGC
 102 Pro Pro Leu Val Phe Leu Leu Glu Thr Gly Ala Phe Arg Glu Ser Ala Gly

596 GCC CGG GCC AAC CGC AGC CAG CGT GGG GTG AGC GAT ACT TCA CCG GTG AGT
 119 Ala Arg Ala Asn Arg Ser Gln Arg Gly Val Ser Asp Thr Ser Pro Val Ser

647 CAT CAG GGT GAG CTG GCC GTG TGC GAT GCA GTC ACT GTC TGG GTG ACA GAC
 136 His Gln Gly Glu Leu Ala Val Cys Asp Ala Val Thr Val Trp Val Thr Asp

698 CCC TGG ACT GCT GTG GAC TTG GGT GTG CTC GAG GTG GAG GTG TTG GGT GAG
 153 Pro Trp Thr Ala Val Asp Leu Gly Val Leu Glu Val Glu Val Leu Gly Glu

749 GTG CCT GCA GCT GGC AGC AGT TCC CTC CGC CAG CAC TTC TTT GTT ACC CGC
 170 Val Pro Ala Ala Gly Ser Ser Ser Leu Arg Gln His Phe Phe Val Thr Arg

800 TTC GAG GCC GAT AAA TCT AAG GAA GGT GGC CCG GGG GTA GGT GGA GGA CCT
 187 Phe Glu Ala Asp Lys Ser Lys Glu Gly Gly Pro Gly Val Gly Gly Gly Pro

851 GCC GCC GGG GTG TGG ACC GGG GGG CAC TGG GTG TCT GAG TGC AAG GCC AAG
 204 Ala Ala Gly Val Trp Thr Gly Gly His Trp Val Ser Glu Cys Lys Ala Lys

902 CAG TCC TAT GGG CGG GCA TTG ACC ACT GAT GCC CAG GGC CGT GTG GAC TGG
 221 Gln Ser Tyr Gly Arg Ala Leu Thr Thr Asp Ala Gln Gly Arg Val Asp Trp

953 CGA TGG ATT CAA ATT GGC ACT GCC TGT GTC TGC ACA CTC CTC AGC CGG ACT
 238 Arg Trp Ile Gln Ile Gly Thr Ala Cys Val Cys Thr Leu Leu Ser Arg Thr

1004 GGC CGG GCC TGA  GACTT ATACCCAGGA ACTGGTCAGG CAGAAAAGA ACAGAGCTGG
 255 Gly Arg Ala OP*

1061 ATGCTGAGAG ACCTCAGGGT TGGCCCAGCT GCTCTACGGA CGGACCCCAG TTGGGGAACT
1121 CATCAAATCA TCGCAAAATC TCAACTGTCT GAATTTGAGC TCAATCTCTG TAGGATGGGT
1181 GCAACAATGT
```

FIG. 4

```
  1 TTTGAACTCC TGACCTCAAG TCAAACACCG CCTCAGCCTC CCAAAGTGCT GGGACCACAG

61 GTGTGAGCCA TAGTGCCTGA CCTGTAGTTG TTGAATATTT ATTATTAATC TACAAGTTGG

121 GTGTGATGCA AGTCCCATAC ATGGAGTCCC CCAAACTTCT AGAGCAAGGG CTTCCCCATA

181 ATCCTGGCAG GCAGGCCTCC CCTGGGGTTC CCAACTTCTG ACCTCACTGA AGTGTTTATC

241 CTCTTCTCTA ATCCCAGCCT CCTTTTCCCT GTTTCCATGT CCTCTGAGAG ATGCTCCCGC

301 TCCCCCAGGC TCCCTCTGCA TCCCCCTCAT TTGCTTCCTC CCCAGTGTGT CAATGGAGTC
```

361 CTAA    CCC CCA CCC TTG ACA TTG TCC CCT TTT CCT CCT CCA GAG TGG
  1         Pro Pro Pro Leu Thr Leu Ser Pro Phe Pro Pro Pro Glu Trp

407 GAC CTT ATT TTC CCC CAA GTG GTC CTG TCT AGG GGT GCC GCT GCC GGG
 15 Asp Leu Ile Phe Pro Gln Val Val Leu Ser Arg Gly Ala Ala Ala Gly

455 CCC CCT CTG GTC TTC CTG CTG GAG ACT GGG GCC TTT TGG GAG TCA GCA
 31 Pro Pro Leu Val Phe Leu Leu Glu Thr Gly Ala Phe Trp Glu Ser Ala

503 GGC ACC CGG GCC AAC CGC AGC CAG CGA GGG GTG AGC GAT ACT TCA CCG
 47 Gly Thr Arg Ala Asn Arg Ser Gln Arg Gly Val Ser Asp Thr Ser Pro

551 GCG AGT CAT CAG GGT GAG CTG GCC GTG TGC GAT GCA GTC AGT GTC TGG
 63 Ala Ser His Gln Gly Glu Leu Ala Val Cys Asp Ala Val Ser Val Trp

599 GTG ACA GAC CCC CGG ACC GCT GTG GAC TTG GTT GTG CTC GAG GTG GAG
 79 Val Thr Asp Pro Arg Thr Ala Val Asp Leu Val Val Leu Glu Val Glu

647 GTG TTG GGT GAG GTG CCT GCA GCT GGC AGC AGT TCC CTC CAC CAA CAC
 95 Val Leu Gly Glu Val Pro Ala Ala Gly Ser Ser Ser Leu His Gln His

695 TTC TTT GTC ACC TGC TTC AAG GCC GAT AAC TCT GAA GAA GGT GGC CCA
111 Phe Phe Val Thr Cys Phe Lys Ala Asp Asn Ser Glu Glu Gly Gly Pro

743 GGG GTA GGT GGA GGG GCT GCC GCT GGG GTG TGG ACC GGG GGG CAC TGG
127 Gly Val Gly Gly Gly Ala Ala Ala Gly Val Trp Thr Gly Gly His Trp

791 GTG TCT GAG TGC AAG GCC AAG CAG TCC TAT GTG CGG GCA TTG ACC GCT
143 Val Ser Glu Cys Lys Ala Lys Gln Ser Tyr Val Arg Ala Leu Thr Ala

839 GAT GCC CAG GGC CGT GTG GAC TGG CGA TGG ATT CAA ACT GGC ACA GCC
159 Asp Ala Gln Gly Arg Val Asp Trp Arg Trp Ile Gln Thr Gly Thr Ala

887 TGT GTC TGC ACA CTC CTC AGC CGG ACT GGC CGG GCC TGA   GACTT
175 Cys Val Cys Thr Leu Leu Ser Arg Thr Gly Arg Ala OP*

931 ATACCCAGGA ACTGGTCAGG CAGAAAAAGA ACAGAGCTAG G

SEQUENCE LISTING (1) GENERAL INFORMATION:

(iii) NUMBER OF SEQUENCES: 100

(2) INFORMATION FOR SEQ ID NO:1:

(i) SEQUENCE CHARACTERISTICS:
      (A) LENGTH: 634 bases
      (B) TYPE: nucleic acid
      (C) STRANDEDNESS: single
      (D) TOPOLOGY: linear (xi) SEQUENCE DESCRIPTION: SEQ ID NO:1:

```
ATGCTCCCTC TCCCCTCATG CTCCCTCCCC ATCCTCCTCC TTTTCCTCCT              50

CCCCAGTGTG CCAATTGAGT CCCAACCCCC ACCCTCAACA TTGCCCCCTT             100

TTCTGGCCCC TGAGTGGGAC CTTCTCTCCC CCCGAGTAGT CCTGTCTAGG             150
```

```
GGTGCCCCTG CTGGGCCCCC TCTGCTCTTC CTGCTGGAGG CTGGGGCCTT         200

TCGGGAGTCA GCAGGTGCCC CGGCCAACCG CAGCCGGCGT GGGGTGAGCG         250

AAACTGCACC AGCGAGTCGT CGGGGTGAGC TGGCTGTGTG CGATGCAGTC         300

AGTGGCTGGG TGACAGACCG CCGGACCGCT GTGGACTTGC GTGGGCGCGA         350

GGTGGAGGTG TTGGGCGAGG TGCCTGCAGC TGGCGGCAGT CCCCTCCGCC         400

AGTACTTCTT TGAAACCCGC TGCAAGGCTG ATAACGCTGA GGAAGGTGGC         450

CCGGGGGCAG GTGGAGGGGG CTGCCGGGGA GTGGACAGGA GGCACTGGGT         500

ATCTGAGTGC AAGGCCAAGC AGTCCTATGT GCGGGCATTG ACCGCTGATG         550

CCCAGGGCCG TGTGGGCTGG CGATGGATTC GAATTGACAC TGCCTGCGTC         600

TGCACACTCC TCAGCCGGAC TGGCCGGGCC TGAG                          634
```

(2) INFORMATION FOR SEQ ID NO:2:

(i) SEQUENCE CHARACTERISTICS:
        (A) LENGTH: 210 amino acids
        (B) TYPE: amino acid
        (D) TOPOLOGY: linear (xi) SEQUENCE DESCRIPTION: SEQ ID NO:2:

```
Met Leu Pro Leu Pro Ser Cys Ser Leu Pro Ile Leu Leu Leu Phe
 1               5                  10                  15

Leu Leu Pro Ser Val Pro Ile Glu Ser Gln Pro Pro Pro Ser Thr
                20                  25                  30

Leu Pro Pro Phe Leu Ala Pro Glu Trp Asp Leu Leu Ser Pro Arg
                35                  40                  45

Val Val Leu Ser Arg Gly Ala Pro Ala Gly Pro Pro Leu Leu Phe
                50                  55                  60

Leu Leu Glu Ala Gly Ala Phe Arg Glu Ser Ala Gly Ala Pro Ala
                65                  70                  75

Asn Arg Ser Arg Arg Gly Val Ser Glu Thr Ala Pro Ala Ser Arg
                80                  85                  90

Arg Gly Glu Leu Ala Val Cys Asp Ala Val Ser Gly Trp Val Thr
                95                 100                 105

Asp Arg Arg Thr Ala Val Asp Leu Arg Gly Arg Glu Val Glu Val
               110                 115                 120

Leu Gly Glu Val Pro Ala Ala Gly Gly Ser Pro Leu Arg Gln Tyr
               125                 130                 135

Phe Phe Glu Thr Arg Cys Lys Ala Asp Asn Ala Glu Glu Gly Gly
               140                 145                 150

Pro Gly Ala Gly Gly Gly Gly Cys Arg Gly Val Asp Arg Arg His
               155                 160                 165

Trp Val Ser Glu Cys Lys Ala Lys Gln Ser Tyr Val Arg Ala Leu
               170                 175                 180

Thr Ala Asp Ala Gln Gly Arg Val Gly Trp Arg Trp Ile Arg Ile
               185                 190                 195

Asp Thr Ala Cys Val Cys Thr Leu Leu Ser Arg Thr Gly Arg Ala
               200                 205                 210
```

(2) INFORMATION FOR SEQ ID NO:3:

(i) SEQUENCE CHARACTERISTICS:
        (A) LENGTH: 247 amino acids
        (B) TYPE: amino acid
        (D) TOPOLOGY: linear (xi) SEQUENCE DESCRIPTION: SEQ ID NO:3:

```
Met Thr Ile Leu Phe Leu Thr Met Val Ile Ser Tyr Phe Gly Cys
 1               5                  10                  15

Met Lys Ala Ala Pro Met Lys Glu Ala Asn Ile Arg Gly Gln Gly
                20                  25                  30

Gly Leu Ala Tyr Pro Gly Val Arg Thr His Gly Thr Leu Glu Ser
                35                  40                  45

Val Asn Gly Pro Lys Ala Gly Ser Arg Gly Leu Thr Ser Leu Ala
                50                  55                  60

Asp Thr Phe Glu His Met Ile Glu Glu Leu Leu Asp Glu Asp Gln
                65                  70                  75

Lys Val Arg Pro Asn Glu Glu Asn Asn Lys Asp Ala Asp Leu Tyr
                80                  85                  90

Thr Ser Arg Val Met Leu Ser Ser Gln Val Pro Leu Glu Pro Pro
                95                 100                 105

Leu Leu Phe Leu Leu Glu Glu Tyr Lys Asn Tyr Leu Asp Ala Ala
               110                 115                 120

Asn Met Ser Met Arg Val Arg Arg His Ser Asp Pro Ala Arg Arg
               125                 130                 135

Gly Glu Leu Ser Val Cys Asp Ser Ile Ser Glu Trp Val Thr Ala
               140                 145                 150

Ala Asp Lys Lys Thr Ala Val Asp Met Ser Gly Gly Thr Val Thr
               155                 160                 165

Val Leu Glu Lys Val Pro Val Ser Lys Gly Gln Leu Lys Gln Tyr
               170                 175                 180

Phe Tyr Glu Thr Lys Cys Asn Pro Met Gly Tyr Thr Lys Glu Gly
               185                 190                 195

Cys Arg Gly Ile Asp Lys Arg His Trp Asn Ser Gln Cys Arg Thr
               200                 205                 210

Thr Gln Ser Tyr Val Arg Ala Leu Thr Met Asp Ser Lys Lys Arg
               215                 220                 225

Ile Gly Trp Arg Phe Ile Arg Ile Asp Thr Ser Cys Val Cys Thr
               230                 235                 240

Leu Thr Ile Lys Arg Gly Arg
               245     247
```

(2) INFORMATION FOR SEQ ID NO:4:

(i) SEQUENCE CHARACTERISTICS:
        (A) LENGTH: 257 amino acids
        (B) TYPE: amino acid
        (D) TOPOLOGY: linear (xi) SEQUENCE DESCRIPTION: SEQ ID NO:4:

```
Met Ser Ile Leu Phe Tyr Val Ile Phe Leu Ala Tyr Leu Arg Gly
 1               5                  10                  15

Ile Gln Gly Asn Asn Met Asp Gln Arg Ser Leu Pro Glu Asp Ser
                20                  25                  30

Leu Asn Ser Leu Ile Ile Lys Leu Ile Gln Ala Asp Ile Leu Lys
                35                  40                  45

Asn Lys Leu Ser Lys Gln Met Val Asp Val Lys Glu Asn Tyr Gln
                50                  55                  60

Ser Thr Leu Pro Lys Ala Glu Ala Pro Arg Glu Pro Glu Arg Gly
                65                  70                  75
```

-continued

```
Gly Pro Ala Lys Ser Ala Phe Gln Pro Val Ile Ala Met Asp Thr
                 80                  85                  90

Glu Leu Leu Arg Gln Gln Arg Arg Tyr Asn Ser Pro Arg Val Leu
                 95                 100                 105

Leu Ser Asp Ser Thr Pro Leu Glu Pro Pro Leu Tyr Leu Met
                110                 115                 120

Glu Asp Tyr Val Gly Ser Pro Val Val Ala Asn Arg Thr Ser Arg
                125                 130                 135

Arg Lys Arg Tyr Ala Glu His Lys Ser His Arg Gly Glu Tyr Ser
                140                 145                 150

Val Cys Asp Ser Glu Ser Leu Trp Val Thr Asp Lys Ser Ser Ala
                155                 160                 165

Ile Asp Ile Arg Gly His Gln Val Thr Val Leu Gly Glu Ile Lys
                170                 175                 180

Thr Gly Asn Ser Pro Val Lys Gln Tyr Phe Tyr Glu Thr Arg Cys
                185                 190                 195

Lys Glu Ala Arg Pro Val Lys Asn Gly Cys Arg Gly Ile Asp Asp
                200                 205                 210

Lys His Trp Asn Ser Gln Cys Lys Thr Ser Gln Thr Tyr Val Arg
                215                 220                 225

Ala Leu Thr Ser Glu Asn Asn Lys Leu Val Gly Trp Arg Trp Ile
                230                 235                 240

Arg Ile Asp Thr Ser Cys Val Cys Ala Leu Ser Arg Lys Ile Gly
                245                 250                 255

Arg Thr
    257

(2) INFORMATION FOR SEQ ID NO:5:

(i) SEQUENCE CHARACTERISTICS:
        (A) LENGTH: 241 amino acids
        (B) TYPE: amino acid
        (D) TOPOLOGY: linear (xi) SEQUENCE DESCRIPTION: SEQ ID NO:5:

Met Ser Met Leu Phe Tyr Thr Leu Ile Thr Ala Phe Leu Ile Gly
  1               5                  10                  15

Ile Gln Ala Glu Pro His Ser Glu Ser Asn Val Pro Ala Gly His
                 20                  25                  30

Thr Ile Pro Gln Val His Trp Thr Lys Leu Gln His Ser Leu Asp
                 35                  40                  45

Thr Ala Leu Arg Arg Ala Arg Ser Ala Pro Ala Ala Ile Ala
                 50                  55                  60

Ala Arg Val Ala Gly Gln Thr Arg Asn Ile Thr Val Asp Pro Arg
                 65                  70                  75

Leu Phe Lys Lys Arg Arg Leu Arg Ser Pro Arg Val Leu Phe Ser
                 80                  85                  90

Thr Gln Pro Pro Arg Glu Ala Ala Asp Thr Gln Asp Leu Asp Phe
                 95                 100                 105

Glu Val Gly Gly Ala Ala Pro Phe Asn Arg Thr His Arg Ser Lys
                110                 115                 120

Arg Ser Ser Ser His Pro Ile Phe His Arg Gly Glu Phe Ser Val
                125                 130                 135

Cys Asp Ser Val Ser Val Trp Val Gly Asp Lys Thr Thr Ala Thr
                140                 145                 150
```

-continued

```
Asp Ile Lys Gly Lys Glu Val Met Val Leu Gly Glu Val Asn Ile
            155                 160                 165

Asn Asn Ser Val Phe Lys Gln Tyr Phe Glu Thr Lys Cys Arg
            170                 175                 180

Asp Pro Asn Pro Val Asp Ser Gly Cys Arg Gly Ile Asp Ser Lys
            185                 190                 195

His Trp Asn Ser Tyr Cys Thr Thr Thr His Thr Phe Val Lys Ala
            200                 205                 210

Leu Thr Met Asp Gly Lys Gln Ala Ala Trp Arg Phe Ile Arg Ile
            215                 220                 225

Asp Thr Ala Cys Val Cys Val Leu Ser Arg Lys Ala Val Arg Arg
            230                 235                 240

Ala
241
```

(2) INFORMATION FOR SEQ ID NO:6:

(i) SEQUENCE CHARACTERISTICS:
        (A) LENGTH: 168 amino acids
        (B) TYPE: amino acid
        (D) TOPOLOGY: linear (xi) SEQUENCE DESCRIPTION: SEQ ID NO:6:

```
Ser Pro Arg Val Val Leu Ser Arg Gly Ala Pro Ala Gly Pro Pro
 1               5                  10                  15

Leu Leu Phe Leu Leu Glu Ala Gly Ala Phe Arg Glu Ser Ala Gly
                20                  25                  30

Ala Pro Ala Asn Arg Ser Arg Arg Gly Val Ser Glu Thr Ala Pro
                35                  40                  45

Ala Ser Arg Arg Gly Glu Leu Ala Val Cys Asp Ala Val Ser Gly
                50                  55                  60

Trp Val Thr Asp Arg Arg Thr Ala Val Asp Leu Arg Gly Arg Glu
                65                  70                  75

Val Glu Val Leu Gly Glu Val Pro Ala Ala Gly Gly Ser Pro Leu
                80                  85                  90

Arg Gln Tyr Phe Phe Glu Thr Arg Cys Lys Ala Asp Asn Ala Glu
                95                  100                 105

Glu Gly Gly Pro Gly Ala Gly Gly Gly Gly Cys Arg Gly Val Asp
                110                 115                 120

Arg Arg His Trp Val Ser Glu Cys Lys Ala Lys Gln Ser Tyr Val
                125                 130                 135

Arg Ala Leu Thr Ala Asp Ala Gln Gly Arg Val Gly Trp Arg Trp
                140                 145                 150

Ile Arg Ile Asp Thr Ala Cys Val Cys Thr Leu Leu Ser Arg Thr
                155                 160                 165

Gly Arg Ala
        168
```

(2) INFORMATION FOR SEQ ID NO:7:

(i) SEQUENCE CHARACTERISTICS:
        (A) LENGTH: 685 bases
        (B) TYPE: nucleic acid
        (C) STRANDEDNESS: single
        (D) TOPOLOGY: linear (xi) SEQUENCE DESCRIPTION: SEQ ID NO:7:

```
CGAGAGATGC TCTGAGAGAT GCTCCCACTC CCCCAGGCTC CCTCCGCATC          50
```

```
CCCCTCATTT TCCTCCTCCC CAGTGTGTCA ATGGAGTCCT AACCCCATCC           100

TCGACATTGT CGCCTTTTCC TCCTCCAGAG TGGGACCTTC TTTTCCCCCG           150

AGTGGTCCTG TCTAGGGGTG CCGCTGCCGG GCCCCCTCTG GTCTTCCTGC           200

TGGAGACTGG AGCCTTTCGG GAGTCAGCAG GCGCCCGGGC CAACCGCAGC           250

CAGCGAGGGG TGAGCGATAC TTCACCGGCG AGTCATCAGG GTGAGCTGGC           300

CGTGTGCGAT GCAGTCAGTG TCTGGGTGAC AGACCCCTGG ACTGCTGTGG           350

ACTTGGGTGT GCTCGAGGTG GAGGTGTTGG GCGAGGTGCC TGCAGCTGTC           400

GGCAGTTCCC TCCGCCAGCA CTTCTTTGTT GCCCGCTTCG AGGCCGATAA           450

ATCTGAGGAA GGTGGCCCGG GGGTAGGTGG AGGGGCTGCC GCCGGGGTGT           500

GGACCGGGGG GCACTGGGTG TCTGAGTGCA AGGCCAAGCA GTCCTATGTG           550

CGGGCATTGA CCGCTGATGC CCAGGGCCGT GTGGACTGGC GATGGATTCA           600

AATTGGCACA GCCTGTGTCT GCACACTCCT CAGCCGGACT GGCCGGGCCT           650

GAGACTTATA CCCAGGAACT GGTCAGGCAG AAAAA                           685
```

(2) INFORMATION FOR SEQ ID NO:8:

(i) SEQUENCE CHARACTERISTICS:
        (A) LENGTH: 216 amino acids
        (B) TYPE: amino acid
        (D) TOPOLOGY: linear (xi) SEQUENCE DESCRIPTION: SEQ ID NO:8:

```
Glu Arg Cys Ser Glu Arg Cys Ser His Ser Pro Arg Leu Pro Pro
  1               5                  10                  15

His Pro Pro His Phe Pro Pro Pro Gln Cys Val Asn Gly Val Leu
                 20                  25                  30

Thr Pro Ser Ser Thr Leu Ser Pro Phe Pro Pro Glu Trp Asp
                 35                  40                  45

Leu Leu Phe Pro Arg Val Val Leu Ser Arg Gly Ala Ala Ala Gly
                 50                  55                  60

Pro Pro Leu Val Phe Leu Leu Glu Thr Gly Ala Phe Arg Glu Ser
                 65                  70                  75

Ala Gly Ala Arg Ala Asn Arg Ser Gln Arg Gly Val Ser Asp Thr
                 80                  85                  90

Ser Pro Ala Ser His Gln Gly Glu Leu Ala Val Cys Asp Ala Val
                 95                 100                 105

Ser Val Trp Val Thr Asp Pro Trp Thr Ala Val Asp Leu Gly Val
                110                 115                 120

Leu Glu Val Glu Val Leu Gly Glu Val Pro Ala Ala Val Gly Ser
                125                 130                 135

Ser Leu Arg Gln His Phe Phe Val Ala Arg Phe Glu Ala Asp Lys
                140                 145                 150

Ser Glu Glu Gly Gly Pro Gly Val Gly Gly Ala Ala Ala Gly
                155                 160                 165

Val Trp Thr Gly Gly His Trp Val Ser Glu Cys Lys Ala Lys Gln
                170                 175                 180

Ser Tyr Val Arg Ala Leu Thr Ala Asp Ala Gln Gly Arg Val Asp
                185                 190                 195

Trp Arg Trp Ile Gln Ile Gly Thr Ala Cys Val Cys Thr Leu Leu
                200                 205                 210
```

Ser Arg Thr Gly Arg Ala
          215  216

(2) INFORMATION FOR SEQ ID NO:9:

(i) SEQUENCE CHARACTERISTICS:
        (A) LENGTH: 1190 bases
        (B) TYPE: nucleic acid
        (C) STRANDEDNESS: single
        (D) TOPOLOGY: linear (xi) SEQUENCE DESCRIPTION: SEQ ID NO:9:

| | |
|---|---:|
| ACTGGAGCGC AGCACCACGC CCAGCTAATT TTGGTATTAT CAGTAGAGAT | 50 |
| GTTGTTTCAC AGTGTTGGCC AGGCTGCTCT CAAACTCCTG ACCTCAAGTC | 100 |
| AAACACCCGC CTCAGCCTCC CAAAGTGCTG GGACTACAGG TGTGAGCCAT | 150 |
| AGTGCCTGAC CTGTAGTTGT TGAATATTTA TTATTAATCT ACAAGTTGGG | 200 |
| TGTGATGCAA GTCCTTTATA TGGAGTCCCC CAAACTTCTA GAGCAAGGGC | 250 |
| TTCCCCATAA TCCTGGCAGG CAGGCCTCCC CTGGGGTTCC CAACTTCTGA | 300 |
| CCCCACTGAA GTGTTTATCT TCTTCCCTAA TCCCAGCCTC CTTTTCCCTG | 350 |
| TCTCCATGTG CTCTGAGAGA TGCTCTGAGA GATGCTCCTG CTCCCCCAGG | 400 |
| CTCCCTCCGC ATCCCCCTCA TTTTCCTCCT CCCCAGTGTG TCATTGGAGT | 450 |
| CCTAACCCCA TCCTCGACAT TGTCGCGTTT TCCTCCTCCA GAGTGGGACC | 500 |
| TTCTTTTCCC CCGAGTGGTC CTGTCTAGGG GTGCCGCTGC CGGGCCCCCT | 550 |
| CTGGTCTTCC TGCTGGAGAC TGGAGCCTTT CGGGAGTCAG CAGGCGCCCG | 600 |
| GGCCAACCGC AGCCAGCGTG GGGTGAGCGA TACTTCACCG GTGAGTCATC | 650 |
| AGGGTGAGCT GGCCGTGTGC GATGCAGTCA CTGTCTGGGT GACAGACCCC | 700 |
| TGGACTGCTG TGGACTTGGG TGTGCTCGAG GTGGAGGTGT TGGGTGAGGT | 750 |
| GCCTGCAGCT GGCAGCAGTT CCCTCCGCCA GCACTTCTTT GTTACCCGCT | 800 |
| TCGAGGCCGA TAAATCTAAG GAAGGTGGCC CGGGGGTAGG TGGAGGACCT | 850 |
| GCCGCCGGGG TGTGGACCGG GGGGCACTGG GTGTCTGAGT GCAAGGCCAA | 900 |
| GCAGTCCTAT GGGCGGGCAT TGACCACTGA TGCCCAGGGC CGTGTGGACT | 950 |
| GGCGATGGAT TCAAATTGGC ACTGCCTGTG TCTGCACACT CCTCAGCCGG | 1000 |
| ACTGGCCGGG CCTGAGACTT ATACCCAGGA ACTGGTCAGG CAGAAAAAGA | 1050 |
| ACAGAGCTGG ATGCTGAGAG ACCTCAGGGT TGGCCCAGCT GCTCTACGGA | 1100 |
| CGGACCCCAG TTGGGGAACT CATCAAATCA TCGCAAAATC TCAACTGTCT | 1150 |
| GAATTTGAGC TCAATCTCTG TAGGATGGGT GCAACAATGT | 1190 |

(2) INFORMATION FOR SEQ ID NO:10:

(i) SEQUENCE CHARACTERISTICS:
        (A) LENGTH: 257 amino acids
        (B) TYPE: amino acid
        (D) TOPOLOGY: linear (xi) SEQUENCE DESCRIPTION: SEQ ID NO:10:

Ser Lys Gly Phe Pro Ile Ile Leu Ala Gly Arg Pro Pro Leu Gly
 1               5                  10                  15

Phe Pro Thr Ser Asp Pro Thr Glu Val Phe Ile Phe Phe Pro Asn
                20                  25                  30

Pro Ser Leu Leu Phe Pro Val Ser Met Cys Ser Glu Arg Cys Ser

```
                 35                  40                  45
Glu Arg Cys Ser Cys Ser Pro Arg Leu Pro Pro His Pro Pro His
                 50                  55                  60

Phe Pro Pro Pro Gln Cys Val Ile Gly Val Leu Thr Pro Ser Ser
                 65                  70                  75

Thr Leu Ser Arg Phe Pro Pro Pro Glu Trp Asp Leu Leu Phe Pro
                 80                  85                  90

Arg Val Val Leu Ser Arg Gly Ala Ala Gly Pro Pro Leu Val
                 95                 100                 105

Phe Leu Leu Glu Thr Gly Ala Phe Arg Glu Ser Ala Gly Ala Arg
                110                 115                 120

Ala Asn Arg Ser Gln Arg Gly Val Ser Asp Thr Ser Pro Val Ser
                125                 130                 135

His Gln Gly Glu Leu Ala Val Cys Asp Ala Val Thr Val Trp Val
                140                 145                 150

Thr Asp Pro Trp Thr Ala Val Asp Leu Gly Val Leu Glu Val Glu
                155                 160                 165

Val Leu Gly Glu Val Pro Ala Ala Gly Ser Ser Ser Leu Arg Gln
                170                 175                 180

His Phe Phe Val Thr Arg Phe Glu Ala Asp Lys Ser Lys Glu Gly
                185                 190                 195

Gly Pro Gly Val Gly Gly Gly Pro Ala Ala Gly Val Trp Thr Gly
                200                 205                 210

Gly His Trp Val Ser Glu Cys Lys Ala Lys Gln Ser Tyr Gly Arg
                215                 220                 225

Ala Leu Thr Thr Asp Ala Gln Gly Arg Val Asp Trp Arg Trp Ile
                230                 235                 240

Gln Ile Gly Thr Ala Cys Val Cys Thr Leu Leu Ser Arg Thr Gly
                245                 250                 255

Arg Ala
    257

(2) INFORMATION FOR SEQ ID NO:11:

(i) SEQUENCE CHARACTERISTICS:
        (A) LENGTH: 971 bases
        (B) TYPE: nucleic acid
        (C) STRANDEDNESS: single
        (D) TOPOLOGY: linear (xi) SEQUENCE DESCRIPTION: SEQ ID NO:11:

TTTGAACTCC TGACCTCAAG TCAAACACCG CCTCAGCCTC CCAAAGTGCT           50

GGGACCACAG GTGTGAGCCA TAGTGCCTGA CCTGTAGTTG TTGAATATTT          100

ATTATTAATC TACAAGTTGG GTGTGATGCA AGTCCCATAC ATGGAGTCCC          150

CCAAACTTCT AGAGCAAGGG CTTCCCCATA ATCCTGGCAG GCAGGCCTCC          200

CCTGGGGTTC CCAACTTCTG ACCTCACTGA AGTGTTTATC CTCTTCTCTA          250

ATCCCAGCCT CCTTTTCCCT GTTTCCATGT CCTCTGAGAG ATGCTCCCGC          300

TCCCCCAGGC TCCCTCTGCA TCCCCCTCAT TTGCTTCCTC CCCAGTGTGT          350

CAATGGAGTC CTAACCCCCA CCCTTGACAT TGTCCCCTTT TCCTCCTCCA          400

GAGTGGGACC TTATTTTCCC CCAAGTGGTC CTGTCTAGGG GTGCCGCTGC          450

CGGGCCCCCT CTGGTCTTCC TGCTGGAGAC TGGGGCCTTT TGGGAGTCAG          500

CAGGCACCCG GGCCAACCGC AGCCAGCGAG GGGTGAGCGA TACTTCACCG          550
```

```
GCGAGTCATC AGGGTGAGCT GGCCGTGTGC GATGCAGTCA GTGTCTGGGT           600

GACAGACCCC CGGACCGCTG TGGACTTGGT TGTGCTCGAG GTGGAGGTGT           650

TGGGTGAGGT GCCTGCAGCT GGCAGCAGTT CCCTCCACCA ACACTTCTTT           700

GTCACCTGCT TCAAGGCCGA TAACTCTGAA GAAGGTGGCC CAGGGGTAGG           750

TGGAGGGGCT GCCGCTGGGG TGTGGACCGG GGGGCACTGG GTGTCTGAGT           800

GCAAGGCCAA GCAGTCCTAT GTGCGGGCAT TGACCGCTGA TGCCCAGGGC           850

CGTGTGGACT GGCGATGGAT TCAAACTGGC ACAGCCTGTG TCTGCACACT           900

CCTCAGCCGG ACTGGCCGGG CCTGAGACTT ATACCCAGGA ACTGGTCAGG           950

CAGAAAAAGA ACAGAGCTAG G                                          971
```

(2) INFORMATION FOR SEQ ID NO:12:

(i) SEQUENCE CHARACTERISTICS:
        (A) LENGTH: 186 amino acids
        (B) TYPE: amino acid
        (D) TOPOLOGY: linear (xi) SEQUENCE DESCRIPTION: SEQ ID NO:12:

```
Pro Pro Pro Leu Thr Leu Ser Pro Phe Pro Pro Glu Trp Asp
  1               5                  10                  15

Leu Ile Phe Pro Gln Val Val Leu Ser Arg Gly Ala Ala Gly
                 20                  25                  30

Pro Pro Leu Val Phe Leu Leu Glu Thr Gly Ala Phe Trp Glu Ser
                 35                  40                  45

Ala Gly Thr Arg Ala Asn Arg Ser Gln Arg Gly Val Ser Asp Thr
                 50                  55                  60

Ser Pro Ala Ser His Gln Gly Glu Leu Ala Val Cys Asp Ala Val
                 65                  70                  75

Ser Val Trp Val Thr Asp Pro Arg Thr Ala Val Asp Leu Val Val
                 80                  85                  90

Leu Glu Val Glu Val Leu Gly Glu Val Pro Ala Ala Gly Ser Ser
                 95                 100                 105

Ser Leu His Gln His Phe Phe Val Thr Cys Phe Lys Ala Asp Asn
                110                 115                 120

Ser Glu Glu Gly Gly Pro Gly Val Gly Gly Ala Ala Ala Gly
                125                 130                 135

Val Trp Thr Gly Gly His Trp Val Ser Glu Cys Lys Ala Lys Gln
                140                 145                 150

Ser Tyr Val Arg Ala Leu Thr Ala Asp Ala Gln Gly Arg Val Asp
                155                 160                 165

Trp Arg Trp Ile Gln Thr Gly Thr Ala Cys Val Cys Thr Leu Leu
                170                 175                 180

Ser Arg Thr Gly Arg Ala
                185 186
```

(2) INFORMATION FOR SEQ ID NO:13:

(i) SEQUENCE CHARACTERISTICS:
        (A) LENGTH: 130 amino acids
        (B) TYPE: amino acid
        (D) TOPOLOGY: linear (xi) SEQUENCE DESCRIPTION: SEQ ID NO:13:

Gly Val Ser Glu Thr Ala Pro Ala Ser Arg Arg Gly Glu Leu Ala

```
          1               5                  10                 15
Val Cys Asp Ala Val Ser Gly Trp Val Thr Asp Arg Arg Thr Ala
                 20                 25                 30

Val Asp Leu Arg Gly Arg Glu Val Glu Val Leu Gly Glu Val Pro
                 35                 40                 45

Ala Ala Gly Gly Ser Pro Leu Arg Gln Tyr Phe Phe Glu Thr Arg
                 50                 55                 60

Cys Lys Ala Asp Asn Ala Glu Glu Gly Gly Pro Gly Ala Gly Gly
                 65                 70                 75

Gly Gly Lys Arg Gly Val Asp Arg Arg His Trp Val Ser Glu Cys
                 80                 85                 90

Lys Ala Lys Gln Ser Tyr Val Arg Ala Leu Thr Ala Asp Ala Gln
                 95                100                105

Gly Arg Val Gly Trp Arg Trp Ile Arg Ile Asp Thr Ala Cys Val
                110                115                120

Cys Thr Leu Leu Ser Arg Thr Gly Arg Ala
                125                130
```

(2) INFORMATION FOR SEQ ID NO:14:

(i) SEQUENCE CHARACTERISTICS:
        (A) LENGTH: 130 amino acids
        (B) TYPE: amino acid
        (D) TOPOLOGY: linear (xi) SEQUENCE DESCRIPTION: SEQ ID NO:14:

```
Gly Val Ser Glu Thr Ala Pro Ala Ser Arg Arg Gly Glu Leu Ala
 1               5                  10                 15

Val Cys Asp Ala Val Ser Gly Trp Val Thr Asp Arg Arg Thr Ala
                 20                 25                 30

Val Asp Leu Arg Gly Arg Glu Val Glu Val Leu Gly Glu Val Pro
                 35                 40                 45

Ala Ala Gly Gly Ser Pro Leu Arg Gln Tyr Phe Phe Glu Thr Arg
                 50                 55                 60

Cys Lys Ala Asp Asn Ala Glu Glu Gly Gly Pro Gly Ala Gly Gly
                 65                 70                 75

Gly Gly His Arg Gly Val Asp Arg Arg His Trp Val Ser Glu Cys
                 80                 85                 90

Lys Ala Lys Gln Ser Tyr Val Arg Ala Leu Thr Ala Asp Ala Gln
                 95                100                105

Gly Arg Val Gly Trp Arg Trp Ile Arg Ile Asp Thr Ala Cys Val
                110                115                120

Cys Thr Leu Leu Ser Arg Thr Gly Arg Ala
                125                130
```

(2) INFORMATION FOR SEQ ID NO:15:

(i) SEQUENCE CHARACTERISTICS:
        (A) LENGTH: 130 amino acids
        (B) TYPE: amino acid
        (D) TOPOLOGY: linear (xi) SEQUENCE DESCRIPTION: SEQ ID NO:15:

```
Gly Val Ser Glu Thr Ala Pro Ala Ser Arg Arg Gly Glu Leu Ala
 1               5                  10                 15

Val Cys Asp Ala Val Ser Gly Trp Val Thr Asp Arg Arg Thr Ala
                 20                 25                 30
```

```
Val Asp Leu Arg Gly Arg Glu Val Glu Val Leu Gly Glu Val Pro
            35                  40                  45

Ala Ala Gly Gly Ser Pro Leu Arg Gln Tyr Phe Phe Glu Thr Arg
            50                  55                  60

Cys Lys Ala Asp Asn Ala Glu Glu Gly Gly Pro Gly Ala Gly Gly
            65                  70                  75

Gly Gly Gln Arg Gly Val Asp Arg Arg His Trp Val Ser Glu Cys
            80                  85                  90

Lys Ala Lys Gln Ser Tyr Val Arg Ala Leu Thr Ala Asp Ala Gln
            95                 100                 105

Gly Arg Val Gly Trp Arg Trp Ile Arg Ile Asp Thr Ala Cys Val
           110                 115                 120

Cys Thr Leu Leu Ser Arg Thr Gly Arg Ala
           125                 130
```

(2) INFORMATION FOR SEQ ID NO:16:

(i) SEQUENCE CHARACTERISTICS:
        (A) LENGTH: 130 amino acids
        (B) TYPE: amino acid
        (D) TOPOLOGY: linear (xi) SEQUENCE DESCRIPTION: SEQ ID NO:16:

```
Gly Val Ser Glu Thr Ala Pro Ala Ser Arg Arg Gly Glu Leu Ala
 1                   5                  10                  15

Val Cys Asp Ala Val Ser Gly Trp Val Thr Asp Arg Arg Thr Ala
            20                  25                  30

Val Asp Leu Arg Gly Arg Glu Val Glu Val Leu Gly Glu Val Pro
            35                  40                  45

Ala Ala Gly Gly Ser Pro Leu Arg Gln Tyr Phe Phe Glu Thr Arg
            50                  55                  60

Cys Lys Ala Asp Asn Ala Glu Glu Gly Gly Pro Gly Ala Gly Gly
            65                  70                  75

Gly Gly Arg Arg Gly Val Asp Arg Arg His Trp Val Ser Glu Cys
            80                  85                  90

Lys Ala Lys Gln Ser Tyr Val Arg Ala Leu Thr Ala Asp Ala Gln
            95                 100                 105

Gly Arg Val Gly Trp Arg Trp Ile Arg Ile Asp Thr Ala Cys Val
           110                 115                 120

Cys Thr Leu Leu Ser Arg Thr Gly Arg Ala
           125                 130
```

(2) INFORMATION FOR SEQ ID NO:17:

(i) SEQUENCE CHARACTERISTICS:
        (A) LENGTH: 130 amino acids
        (B) TYPE: amino acid
        (D) TOPOLOGY: linear (xi) SEQUENCE DESCRIPTION: SEQ ID NO:17:

```
Gly Val Ser Glu Thr Ala Pro Ala Ser Arg Arg Gly Glu Leu Ala
 1                   5                  10                  15

Val Cys Asp Ala Val Ser Gly Trp Val Thr Asp Arg Arg Thr Ala
            20                  25                  30

Val Asp Leu Arg Gly Arg Glu Val Glu Val Leu Gly Glu Val Pro
            35                  40                  45

Ala Ala Gly Gly Ser Pro Leu Arg Gln Tyr Phe Phe Glu Thr Arg
            50                  55                  60
```

Cys Lys Ala Asp Asn Ala Glu Glu Gly Gly Pro Gly Ala Gly Gly
                65                  70                  75

Gly Gly Cys Arg Gly Val Asp Arg Arg Glu Trp Val Ser Glu Cys
            80                  85                  90

Lys Ala Lys Gln Ser Tyr Val Arg Ala Leu Thr Ala Asp Ala Gln
        95                 100                 105

Gly Arg Val Gly Trp Arg Trp Ile Arg Ile Asp Thr Ala Cys Val
    110                 115                 120

Cys Thr Leu Leu Ser Arg Thr Gly Arg Ala
125                 130

(2) INFORMATION FOR SEQ ID NO:18:

(i) SEQUENCE CHARACTERISTICS:
        (A) LENGTH: 130 amino acids
        (B) TYPE: amino acid
        (D) TOPOLOGY: linear (xi) SEQUENCE DESCRIPTION: SEQ ID NO:18:

Gly Val Ser Glu Thr Ala Pro Ala Ser Arg Arg Gly Glu Leu Ala
1               5                  10                  15

Val Cys Asp Ala Val Ser Gly Trp Val Thr Asp Arg Arg Thr Ala
            20                  25                  30

Val Asp Leu Arg Gly Arg Glu Val Glu Val Leu Gly Glu Val Pro
        35                  40                  45

Ala Ala Gly Gly Ser Pro Leu Arg Gln Tyr Phe Phe Glu Thr Arg
    50                  55                  60

Cys Lys Ala Asp Asn Ala Glu Glu Gly Gly Pro Gly Ala Gly Gly
                65                  70                  75

Gly Gly Cys Arg Gly Val Asp Arg Arg Phe Trp Val Ser Glu Cys
            80                  85                  90

Lys Ala Lys Gln Ser Tyr Val Arg Ala Leu Thr Ala Asp Ala Gln
        95                 100                 105

Gly Arg Val Gly Trp Arg Trp Ile Arg Ile Asp Thr Ala Cys Val
    110                 115                 120

Cys Thr Leu Leu Ser Arg Thr Gly Arg Ala
125                 130

(2) INFORMATION FOR SEQ ID NO:19:

(i) SEQUENCE CHARACTERISTICS:
        (A) LENGTH: 130 amino acids
        (B) TYPE: amino acid
        (D) TOPOLOGY: linear (xi) SEQUENCE DESCRIPTION: SEQ ID NO:19:

Gly Val Ser Glu Thr Ala Pro Ala Ser Arg Arg Gly Glu Leu Ala
1               5                  10                  15

Val Cys Asp Ala Val Ser Gly Trp Val Thr Asp Arg Arg Thr Ala
            20                  25                  30

Val Asp Leu Arg Gly Arg Glu Val Glu Val Leu Gly Glu Val Pro
        35                  40                  45

Ala Ala Gly Gly Ser Pro Leu Arg Gln Tyr Phe Phe Glu Thr Arg
    50                  55                  60

Cys Lys Ala Asp Asn Ala Glu Glu Gly Gly Pro Gly Ala Gly Gly
                65                  70                  75

Gly Gly Cys Arg Gly Val Asp Arg Arg Pro Trp Val Ser Glu Cys

```
                    80                  85                  90
Lys Ala Lys Gln Ser Tyr Val Arg Ala Leu Thr Ala Asp Ala Gln
                95                 100                 105
Gly Arg Val Gly Trp Arg Trp Ile Arg Ile Asp Thr Ala Cys Val
            110                 115                 120
Cys Thr Leu Leu Ser Arg Thr Gly Arg Ala
        125                 130

(2) INFORMATION FOR SEQ ID NO:20:

(i) SEQUENCE CHARACTERISTICS:
        (A) LENGTH: 130 amino acids
        (B) TYPE: amino acid
        (D) TOPOLOGY: linear (xi) SEQUENCE DESCRIPTION: SEQ ID NO:20:

Gly Val Ser Glu Thr Ala Pro Ala Ser Arg Arg Gly Glu Leu Ala
  1               5                  10                  15
Val Cys Asp Ala Val Ser Gly Trp Val Thr Asp Arg Arg Thr Ala
                 20                  25                  30
Val Asp Leu Arg Gly Arg Glu Val Glu Val Leu Gly Glu Val Pro
                 35                  40                  45
Ala Ala Gly Gly Ser Pro Leu Arg Gln Tyr Phe Phe Glu Thr Arg
                 50                  55                  60
Cys Lys Ala Asp Asn Ala Glu Glu Gly Gly Pro Gly Ala Gly Gly
                 65                  70                  75
Gly Gly Cys Arg Gly Val Asp Arg Arg Tyr Trp Val Ser Glu Cys
                 80                  85                  90
Lys Ala Lys Gln Ser Tyr Val Arg Ala Leu Thr Ala Asp Ala Gln
                 95                 100                 105
Gly Arg Val Gly Trp Arg Trp Ile Arg Ile Asp Thr Ala Cys Val
            110                 115                 120
Cys Thr Leu Leu Ser Arg Thr Gly Arg Ala
        125                 130

(2) INFORMATION FOR SEQ ID NO:21:

(i) SEQUENCE CHARACTERISTICS:
        (A) LENGTH: 130 amino acids
        (B) TYPE: amino acid
        (D) TOPOLOGY: linear (xi) SEQUENCE DESCRIPTION: SEQ ID NO:21:

Gly Val Ser Glu Thr Ala Pro Ala Ser Arg Arg Gly Glu Leu Ala
  1               5                  10                  15
Val Cys Asp Ala Val Ser Gly Trp Val Thr Asp Arg Arg Thr Ala
                 20                  25                  30
Val Asp Leu Arg Gly Arg Glu Val Glu Val Leu Gly Glu Val Pro
                 35                  40                  45
Ala Ala Gly Gly Ser Pro Leu Arg Gln Tyr Phe Phe Glu Thr Arg
                 50                  55                  60
Cys Lys Ala Asp Asn Ala Glu Glu Gly Gly Pro Gly Ala Gly Gly
                 65                  70                  75
Gly Gly Cys Arg Gly Val Asp Arg Arg Trp Trp Val Ser Glu Cys
                 80                  85                  90
Lys Ala Lys Gln Ser Tyr Val Arg Ala Leu Thr Ala Asp Ala Gln
                 95                 100                 105
```

Gly Arg Val Gly Trp Arg Trp Ile Arg Ile Asp Thr Ala Cys Val
            110                 115                 120

Cys Thr Leu Leu Ser Arg Thr Gly Arg Ala
            125                 130

(2) INFORMATION FOR SEQ ID NO:22:

(i) SEQUENCE CHARACTERISTICS:
        (A) LENGTH: 130 amino acids
        (B) TYPE: amino acid
        (D) TOPOLOGY: linear (xi) SEQUENCE DESCRIPTION: SEQ ID NO:22:

Gly Val Ser Glu Thr Ala Pro Ala Ser Arg Arg Gly Glu Leu Ala
  1               5                  10                  15

Val Cys Asp Ala Val Ser Gly Trp Val Thr Asp Arg Arg Thr Ala
             20                  25                  30

Val Asp Leu Arg Gly Arg Glu Val Glu Val Leu Gly Glu Val Pro
             35                  40                  45

Ala Ala Gly Gly Ser Pro Leu Arg Gln Tyr Phe Phe Glu Thr Arg
             50                  55                  60

Cys Lys Ala Asp Asn Ala Ser Glu Gly Gly Pro Gly Ala Gly Gly
             65                  70                  75

Gly Gly Cys Arg Gly Val Asp Arg Arg His Trp Val Ser Glu Cys
             80                  85                  90

Lys Ala Lys Gln Ser Tyr Val Arg Ala Leu Thr Ala Asp Ala Gln
             95                 100                 105

Gly Arg Val Gly Trp Arg Trp Ile Arg Ile Asp Thr Ala Cys Val
            110                 115                 120

Cys Thr Leu Leu Ser Arg Thr Gly Arg Ala
            125                 130

(2) INFORMATION FOR SEQ ID NO:23:

(i) SEQUENCE CHARACTERISTICS:
        (A) LENGTH: 130 amino acids
        (B) TYPE: amino acid
        (D) TOPOLOGY: linear (xi) SEQUENCE DESCRIPTION: SEQ ID NO:23:

Gly Val Ser Glu Thr Ala Pro Ala Ser Arg Arg Gly Glu Leu Ala
  1               5                  10                  15

Val Cys Asp Ala Val Ser Gly Trp Val Thr Asp Arg Arg Thr Ala
             20                  25                  30

Val Asp Leu Arg Gly Arg Glu Val Glu Val Leu Gly Glu Val Pro
             35                  40                  45

Ala Ala Gly Gly Ser Pro Leu Arg Gln Tyr Phe Phe Glu Thr Arg
             50                  55                  60

Cys Lys Ala Asp Asn Ala Thr Glu Gly Gly Pro Gly Ala Gly Gly
             65                  70                  75

Gly Gly Cys Arg Gly Val Asp Arg Arg His Trp Val Ser Glu Cys
             80                  85                  90

Lys Ala Lys Gln Ser Tyr Val Arg Ala Leu Thr Ala Asp Ala Gln
             95                 100                 105

Gly Arg Val Gly Trp Arg Trp Ile Arg Ile Asp Thr Ala Cys Val
            110                 115                 120

Cys Thr Leu Leu Ser Arg Thr Gly Arg Ala
            125                 130

(2) INFORMATION FOR SEQ ID NO:24:

(i) SEQUENCE CHARACTERISTICS:
　　　　(A) LENGTH: 12 amino acids
　　　　(B) TYPE: amino acid
　　　　(D) TOPOLOGY: linear (xi) SEQUENCE DESCRIPTION: SEQ ID NO:24:

Arg Arg His Trp Val Ser Glu Cys Lys Ala Lys Gln
 1               5                  10      12

(2) INFORMATION FOR SEQ ID NO:25:

(i) SEQUENCE CHARACTERISTICS:
　　　　(A) LENGTH: 61 amino acids
　　　　(B) TYPE: amino acid
　　　　(D) TOPOLOGY: linear (xi) SEQUENCE DESCRIPTION: SEQ ID NO:25:

Gly Val Ser Glu Thr Ala Pro Ala Ser Arg Arg Gly Glu Leu Ala
 1               5                  10                  15

Val Cys Asp Ala Val Ser Gly Trp Val Thr Asp Arg Arg Thr Ala
                20                  25                  30

Val Asp Leu Arg Gly Arg Glu Val Glu Val Leu Gly Glu Val Pro
                35                  40                  45

Ala Ala Gly Gly Ser Pro Leu Arg Gln Tyr Phe Phe Glu Thr Arg
                50                  55                  60

Cys
 61

(2) INFORMATION FOR SEQ ID NO:26:

(i) SEQUENCE CHARACTERISTICS:
　　　　(A) LENGTH: 17 amino acids
　　　　(B) TYPE: amino acid
　　　　(D) TOPOLOGY: linear (xi) SEQUENCE DESCRIPTION: SEQ ID NO:26:

Gly Val Ser Glu Thr Ala Pro Ala Ser Arg Arg Gly Glu Leu Ala
 1               5                  10                  15

Val Cys
     17

(2) INFORMATION FOR SEQ ID NO:27:

(i) SEQUENCE CHARACTERISTICS:
　　　　(A) LENGTH: 45 amino acids
　　　　(B) TYPE: amino acid
　　　　(D) TOPOLOGY: linear (xi) SEQUENCE DESCRIPTION: SEQ ID NO:27:

Cys Asp Ala Val Ser Gly Trp Val Thr Asp Arg Arg Thr Ala Val
 1               5                  10                  15

Asp Leu Arg Gly Arg Glu Val Glu Val Leu Gly Glu Val Pro Ala
                20                  25                  30

Ala Gly Gly Ser Pro Leu Arg Gln Tyr Phe Phe Glu Thr Arg Cys
                35                  40                  45

(2) INFORMATION FOR SEQ ID NO:28:

(i) SEQUENCE CHARACTERISTICS:
　　　　(A) LENGTH: 62 amino acids (B) TYPE: amino acid
        (D) TOPOLOGY: linear (xi) SEQUENCE DESCRIPTION: SEQ ID NO:28:

Cys Asp Ala Val Ser Gly Trp Val Thr Asp Arg Arg Thr Ala Val
 1               5                  10                  15

Asp Leu Arg Gly Arg Glu Val Glu Val Leu Gly Glu Val Pro Ala
                20                  25                  30

Ala Gly Gly Ser Pro Leu Arg Gln Tyr Phe Phe Glu Thr Arg Cys
                35                  40                  45

Lys Ala Asp Asn Ala Glu Glu Gly Pro Gly Ala Gly Gly Gly
                50                  55                  60

Gly Cys
    62

(2) INFORMATION FOR SEQ ID NO:29:

(i) SEQUENCE CHARACTERISTICS:
        (A) LENGTH: 74 amino acids
        (B) TYPE: amino acid
        (D) TOPOLOGY: linear (xi) SEQUENCE DESCRIPTION: SEQ ID NO:29:

Cys Asp Ala Val Ser Gly Trp Val Thr Asp Arg Arg Thr Ala Val
 1               5                  10                  15

Asp Leu Arg Gly Arg Glu Val Glu Val Leu Gly Glu Val Pro Ala
                20                  25                  30

Ala Gly Gly Ser Pro Leu Arg Gln Tyr Phe Phe Glu Thr Arg Cys
                35                  40                  45

Lys Ala Asp Asn Ala Glu Glu Gly Pro Gly Ala Gly Gly Gly
                50                  55                  60

Gly Cys Arg Gly Val Asp Arg Arg His Trp Val Ser Glu Cys
                65                  70                  74

(2) INFORMATION FOR SEQ ID NO:30:

(i) SEQUENCE CHARACTERISTICS:
        (A) LENGTH: 103 amino acids
        (B) TYPE: amino acid
        (D) TOPOLOGY: linear (xi) SEQUENCE DESCRIPTION: SEQ ID NO:30:

Cys Asp Ala Val Ser Gly Trp Val Thr Asp Arg Arg Thr Ala Val
 1               5                  10                  15

Asp Leu Arg Gly Arg Glu Val Glu Val Leu Gly Glu Val Pro Ala
                20                  25                  30

Ala Gly Gly Ser Pro Leu Arg Gln Tyr Phe Phe Glu Thr Arg Cys
                35                  40                  45

Lys Ala Asp Asn Ala Glu Glu Gly Pro Gly Ala Gly Gly Gly
                50                  55                  60

Gly Cys Arg Gly Val Asp Arg Arg His Trp Val Ser Glu Cys Lys
                65                  70                  75

Ala Lys Gln Ser Tyr Val Arg Ala Leu Thr Ala Asp Ala Gln Gly
                80                  85                  90

Arg Val Gly Trp Arg Trp Ile Arg Ile Asp Thr Ala Cys
                95                  100         103

(2) INFORMATION FOR SEQ ID NO:31:

(i) SEQUENCE CHARACTERISTICS:
    (A) LENGTH: 105 amino acids
    (B) TYPE: amino acid
    (D) TOPOLOGY: linear (xi) SEQUENCE DESCRIPTION: SEQ ID NO:31:

Cys Asp Ala Val Ser Gly Trp Val Thr Asp Arg Thr Ala Val
 1               5                  10                 15

Asp Leu Arg Gly Arg Glu Val Glu Val Leu Gly Glu Val Pro Ala
                20                  25                  30

Ala Gly Gly Ser Pro Leu Arg Gln Tyr Phe Phe Glu Thr Arg Cys
                35                  40                  45

Lys Ala Asp Asn Ala Glu Glu Gly Gly Pro Gly Ala Gly Gly Gly
                50                  55                  60

Gly Cys Arg Gly Val Asp Arg Arg His Trp Val Ser Glu Cys Lys
                65                  70                  75

Ala Lys Gln Ser Tyr Val Arg Ala Leu Thr Ala Asp Ala Gln Gly
                80                  85                  90

Arg Val Gly Trp Arg Trp Ile Arg Ile Asp Thr Ala Cys Val Cys
                95                 100                 105

(2) INFORMATION FOR SEQ ID NO:32:

(i) SEQUENCE CHARACTERISTICS:
        (A) LENGTH: 17 amino acids
        (B) TYPE: amino acid
        (D) TOPOLOGY: linear (xi) SEQUENCE DESCRIPTION: SEQ ID NO:32:

Arg Gly Glu Leu Ala Val Cys Asp Ala Val Ser Gly Trp Val Thr
 1               5                  10                  15

Asp Arg
    17

(2) INFORMATION FOR SEQ ID NO:33:

(i) SEQUENCE CHARACTERISTICS:
        (A) LENGTH: 24 amino acids
        (B) TYPE: amino acid
        (D) TOPOLOGY: linear (xi) SEQUENCE DESCRIPTION: SEQ ID NO:33:

Arg Gly Glu Leu Ala Val Cys Asp Ala Val Ser Gly Trp Val Thr
 1               5                  10                  15

Asp Arg Arg Thr Ala Val Asp Leu Arg
                20                  24

(2) INFORMATION FOR SEQ ID NO:34:

(i) SEQUENCE CHARACTERISTICS:
        (A) LENGTH: 20 amino acids
        (B) TYPE: amino acid
        (D) TOPOLOGY: linear (xi) SEQUENCE DESCRIPTION: SEQ ID NO:34:

Arg Gly Arg Glu Val Glu Val Leu Gly Glu Val Pro Ala Ala Gly
 1               5                  10                  15

Gly Ser Pro Leu Arg
                20

(2) INFORMATION FOR SEQ ID NO:35:

(i) SEQUENCE CHARACTERISTICS:
        (A) LENGTH: 18 amino acids
        (B) TYPE: amino acid
        (D) TOPOLOGY: linear (xi) SEQUENCE DESCRIPTION: SEQ ID NO:35:

Cys Lys Ala Asp Asn Ala Glu Glu Gly Gly Pro Gly Ala Gly Gly
 1               5                  10                  15

Gly Gly Cys
        18

(2) INFORMATION FOR SEQ ID NO:36:

(i) SEQUENCE CHARACTERISTICS:
        (A) LENGTH: 9 amino acids
        (B) TYPE: amino acid
        (D) TOPOLOGY: linear (xi) SEQUENCE DESCRIPTION: SEQ ID NO:36:

Arg Gln Tyr Phe Phe Glu Thr Arg Cys
 1               5               9

(2) INFORMATION FOR SEQ ID NO:37:

(i) SEQUENCE CHARACTERISTICS:
        (A) LENGTH: 59 amino acids
        (B) TYPE: amino acid
        (D) TOPOLOGY: linear (xi) SEQUENCE DESCRIPTION: SEQ ID NO:37:

Cys Lys Ala Asp Asn Ala Glu Glu Gly Gly Pro Gly Ala Gly Gly
 1               5                  10                  15

Gly Gly Cys Arg Gly Val Asp Arg Arg His Trp Val Ser Glu Cys
                20                  25                  30

Lys Ala Lys Gln Ser Tyr Val Arg Ala Leu Thr Ala Asp Ala Gln
                35                  40                  45

Gly Arg Val Gly Trp Arg Trp Ile Arg Ile Asp Thr Ala Cys
                50                  55              59

(2) INFORMATION FOR SEQ ID NO:38:

(i) SEQUENCE CHARACTERISTICS:
        (A) LENGTH: 18 amino acids
        (B) TYPE: amino acid
        (D) TOPOLOGY: linear (xi) SEQUENCE DESCRIPTION: SEQ ID NO:38:

Cys Lys Ala Asp Asn Ala Glu Glu Gly Gly Pro Gly Ala Gly Gly
 1               5                  10                  15

Gly Gly Cys
        18

(2) INFORMATION FOR SEQ ID NO:39:

(i) SEQUENCE CHARACTERISTICS:
        (A) LENGTH: 42 amino acids
        (B) TYPE: amino acid
        (D) TOPOLOGY: linear (xi) SEQUENCE DESCRIPTION: SEQ ID NO:39:

Cys Arg Gly Val Asp Arg Arg His Trp Val Ser Glu Cys Lys Ala
 1               5                  10                  15

Lys Gln Ser Tyr Val Arg Ala Leu Thr Ala Asp Ala Gln Gly Arg
                20                  25                  30

```
Val Gly Trp Arg Trp Ile Arg Ile Asp Thr Ala Cys
            35                  40      42
```

(2) INFORMATION FOR SEQ ID NO:40:

(i) SEQUENCE CHARACTERISTICS:
        (A) LENGTH: 30 amino acids
        (B) TYPE: amino acid
        (D) TOPOLOGY: linear (xi) SEQUENCE DESCRIPTION: SEQ ID NO:40:

```
Cys Lys Ala Asp Asn Ala Glu Glu Gly Gly Pro Gly Ala Gly Gly
 1               5                  10                  15

Gly Gly Cys Arg Gly Val Asp Arg Arg His Trp Val Ser Glu Cys
            20                  25                  30
```

(2) INFORMATION FOR SEQ ID NO:41:

(i) SEQUENCE CHARACTERISTICS:
        (A) LENGTH: 19 amino acids
        (B) TYPE: amino acid
        (D) TOPOLOGY: linear (xi) SEQUENCE DESCRIPTION: SEQ ID NO:41:

```
Arg Cys Lys Ala Asp Asn Ala Glu Glu Gly Gly Pro Gly Ala Gly
 1               5                  10                  15

Gly Gly Gly Cys
            19
```

(2) INFORMATION FOR SEQ ID NO:42:

(i) SEQUENCE CHARACTERISTICS:
        (A) LENGTH: 58 amino acids
        (B) TYPE: amino acid
        (D) TOPOLOGY: linear (xi) SEQUENCE DESCRIPTION: SEQ ID NO:42:

```
Lys Ala Asp Asn Ala Glu Glu Gly Gly Pro Gly Ala Gly Gly Gly
 1               5                  10                  15

Gly Cys Arg Gly Val Asp Arg Arg His Trp Val Ser Glu Cys Lys
            20                  25                  30

Ala Lys Gln Ser Tyr Val Arg Ala Leu Thr Ala Asp Ala Gln Gly
            35                  40                  45

Arg Val Gly Trp Arg Trp Ile Arg Ile Asp Thr Ala Cys
            50                  55              58
```

(2) INFORMATION FOR SEQ ID NO:43:

(i) SEQUENCE CHARACTERISTICS:
        (A) LENGTH: 30 amino acids
        (B) TYPE: amino acid
        (D) TOPOLOGY: linear (xi) SEQUENCE DESCRIPTION: SEQ ID NO:43:

```
Lys Ala Asp Asn Ala Glu Glu Gly Gly Pro Gly Ala Gly Gly Gly
 1               5                  10                  15

Gly Cys Arg Gly Val Asp Arg Arg His Trp Val Ser Glu Cys Lys
            20                  25                  30
```

(2) INFORMATION FOR SEQ ID NO:44:

(i) SEQUENCE CHARACTERISTICS:
        (A) LENGTH: 20 amino acids (B) TYPE: amino acid
        (D) TOPOLOGY: linear (xi) SEQUENCE DESCRIPTION: SEQ ID NO:44:

Arg Gly Val Asp Arg Arg His Trp Val Ser Glu Cys Lys Ala Lys
 1               5                  10                  15

Gln Ser Tyr Val Arg
            20

(2) INFORMATION FOR SEQ ID NO:45:

(i) SEQUENCE CHARACTERISTICS:
        (A) LENGTH: 11 amino acids
        (B) TYPE: amino acid
        (D) TOPOLOGY: linear (xi) SEQUENCE DESCRIPTION: SEQ ID NO:45:

Arg Arg His Trp Val Ser Glu Cys Lys Ala Lys
 1               5                  10  11

(2) INFORMATION FOR SEQ ID NO:46:

(i) SEQUENCE CHARACTERISTICS:
        (A) LENGTH: 11 amino acids
        (B) TYPE: amino acid
        (D) TOPOLOGY: linear (xi) SEQUENCE DESCRIPTION: SEQ ID NO:46:

Thr Ala Asp Ala Gln Gly Arg Val Gly Trp Arg
 1               5                  10  11

(2) INFORMATION FOR SEQ ID NO:47:

(i) SEQUENCE CHARACTERISTICS:
        (A) LENGTH: 130 amino acids
        (B) TYPE: amino acid
        (D) TOPOLOGY: linear (xi) SEQUENCE DESCRIPTION: SEQ ID NO:47:

Gly Val Ser Glu Thr Ala Pro Ala Ser Arg Arg Gly Glu Leu Ala
 1               5                  10                  15

Val Cys Asp Ala Val Ser Gly Trp Val Thr Asp Arg Arg Thr Ala
                20                  25                  30

Val Asp Leu Arg Gly Arg Glu Val Glu Val Leu Gly Glu Val Pro
                35                  40                  45

Ala Ala Gly Gly Ser Pro Leu Arg Gln Tyr Phe Phe Glu Thr Arg
                50                  55                  60

Cys Lys Ala Asp Asn Ala Glu Glu Gly Pro Gly Ala Gly Gly
                65                  70                  75

Gly Gly Cys Arg Gly Val Asp Arg Arg His Trp Val Ser Glu Cys
                80                  85                  90

Lys Ala Lys Gln Ser Tyr Val Arg Ala Leu Thr Ala Asp Ala Gln
                95                 100                 105

Gly Arg Val Gly Trp Arg Trp Ile Arg Ile Asp Thr Ala Cys Val
               110                 115                 120

Cys Val Leu Thr Val Lys Arg Val Arg Arg
               125                 130

(2) INFORMATION FOR SEQ ID NO:48:

(i) SEQUENCE CHARACTERISTICS:
        (A) LENGTH: 91 amino acids (B) TYPE: amino acid
        (D) TOPOLOGY: linear (xi) SEQUENCE DESCRIPTION: SEQ ID NO:48:

Val Leu Gly Glu Val Pro Ala Ala Gly Gly Ser Pro Leu Arg Gln
 1               5                  10                  15

Tyr Phe Phe Glu Thr Arg Cys Lys Ala Asp Asn Ala Glu Glu Gly
                20                  25                  30

Gly Pro Gly Ala Gly Gly Gly Gly Cys Arg Gly Val Asp Arg Arg
                35                  40                  45

His Trp Val Ser Glu Cys Lys Ala Lys Gln Ser Tyr Val Arg Ala
                50                  55                  60

Leu Thr Ala Asp Ala Gln Gly Arg Val Gly Trp Arg Trp Ile Arg
                65                  70                  75

Ile Asp Thr Ala Cys Val Cys Val Leu Thr Val Lys Arg Val Arg
                80                  85                  90

Arg
 91

(2) INFORMATION FOR SEQ ID NO:49:

(i) SEQUENCE CHARACTERISTICS:
        (A) LENGTH: 91 amino acids
        (B) TYPE: amino acid
        (D) TOPOLOGY: linear (xi) SEQUENCE DESCRIPTION: SEQ ID NO:49:

Val Leu Gly Glu Val Pro Ala Ala Gly Gly Ser Pro Leu Arg Gln
 1               5                  10                  15

Tyr Phe Phe Glu Thr Arg Cys Lys Ala Asp Asn Ala Glu Glu Gly
                20                  25                  30

Gly Pro Gly Ala Gly Gly Gly Gly Cys Arg Gly Val Asp Arg Arg
                35                  40                  45

His Trp Val Ser Glu Cys Lys Ala Lys Gln Ser Tyr Val Arg Ala
                50                  55                  60

Leu Thr Ala Asp Ala Gln Gly Arg Val Gly Trp Arg Trp Ile Arg
                65                  70                  75

Ile Asp Thr Ala Cys Val Cys Ser Leu Thr Ile Lys Arg Ile Arg
                80                  85                  90

Ala
 91

(2) INFORMATION FOR SEQ ID NO:50:

(i) SEQUENCE CHARACTERISTICS:
        (A) LENGTH: 92 amino acids
        (B) TYPE: amino acid
        (D) TOPOLOGY: linear (xi) SEQUENCE DESCRIPTION: SEQ ID NO:50:

Val Leu Gly Glu Val Pro Ala Ala Gly Gly Ser Pro Leu Arg Gln
 1               5                  10                  15

Tyr Phe Phe Glu Thr Arg Cys Lys Ala Asp Asn Ala Glu Glu Gly
                20                  25                  30

Gly Pro Gly Ala Gly Gly Gly Gly Cys Arg Gly Val Asp Arg Arg
                35                  40                  45

His Trp Val Ser Glu Cys Lys Ala Lys Gln Ser Tyr Val Arg Ala
                50                  55                  60

```
Leu Thr Ala Asp Ala Gln Gly Arg Val Gly Trp Arg Trp Ile Arg
                65                  70                  75

Ile Asp Thr Ala Cys Val Cys Thr Leu Ser Arg Lys Ala Gly Arg
                80                  85                  90

Arg Ala
    92

(2) INFORMATION FOR SEQ ID NO:51:

(i) SEQUENCE CHARACTERISTICS:
        (A) LENGTH: 132 amino acids
        (B) TYPE: amino acid
        (D) TOPOLOGY: linear (xi) SEQUENCE DESCRIPTION: SEQ ID NO:51:

Asp Asp Asp Ser Pro Ile Ala Arg Arg Gly Glu Ile Ser Val Cys
  1               5                  10                  15

Asp Ser Val Ser Asp Trp Val Ser Ala Pro Asp Lys Asp Thr Ala
                20                  25                  30

Val Asp Ile Lys Gly Asp Asp Val Met Val Leu Lys Lys Val Gly
                35                  40                  45

Ile Asn His Ser Val Val Leu Gly Glu Val Pro Ala Ala Gly Gly
                50                  55                  60

Ser Pro Leu Arg Gln Tyr Phe Phe Glu Thr Arg Cys Lys Ala Asp
                65                  70                  75

Asn Ala Glu Glu Gly Gly Pro Gly Ala Gly Gly Gly Cys Arg
                80                  85                  90

Gly Val Asp Arg Arg His Trp Val Ser Glu Cys Lys Ala Lys Gln
                95                 100                 105

Ser Tyr Val Arg Ala Leu Thr Ala Asp Ala Gln Gly Arg Val Gly
               110                 115                 120

Trp Arg Trp Ile Arg Ile Asp Thr Ala Cys Val Cys
               125                 130     132

(2) INFORMATION FOR SEQ ID NO:52:

(i) SEQUENCE CHARACTERISTICS:
        (A) LENGTH: 142 amino acids
        (B) TYPE: amino acid
        (D) TOPOLOGY: linear (xi) SEQUENCE DESCRIPTION: SEQ ID NO:52:

Ser Ser Ser His Pro Ile Phe His Arg Gly Glu Phe Ser Val Cys
  1               5                  10                  15

Asp Ser Val Ser Val Trp Val Gly Asp Lys Thr Thr Ala Thr Asp
                20                  25                  30

Ile Lys Gly Lys Glu Val Met Val Leu Gly Glu Val Asn Ile Asn
                35                  40                  45

Asn Ser Val Val Leu Gly Glu Val Pro Ala Ala Gly Gly Ser Pro
                50                  55                  60

Leu Arg Gln Tyr Phe Phe Glu Thr Arg Cys Lys Ala Asp Asn Ala
                65                  70                  75

Glu Glu Gly Gly Pro Gly Ala Gly Gly Gly Cys Arg Gly Val
                80                  85                  90

Asp Arg Arg His Trp Val Ser Glu Cys Lys Ala Lys Gln Ser Tyr
                95                 100                 105

Val Arg Ala Leu Thr Ala Asp Ala Gln Gly Arg Val Gly Trp Arg
               110                 115                 120
```

```
Trp Ile Arg Ile Asp Thr Ala Cys Val Cys Val Cys Val Leu Ser
            125                 130                 135

Arg Lys Ala Val Arg Arg Ala
            140     142
```

(2) INFORMATION FOR SEQ ID NO:53:

(i) SEQUENCE CHARACTERISTICS:
        (A) LENGTH: 129 amino acids
        (B) TYPE: amino acid
        (D) TOPOLOGY: linear (xi) SEQUENCE DESCRIPTION: SEQ ID NO:53:

```
Gly Val Ser Glu Thr Ala Pro Ala Ser Arg Arg Gly Glu Leu Ala
 1               5                  10                  15

Val Cys Asp Ala Val Ser Gly Trp Val Thr Asp Arg Arg Thr Ala
                20                  25                  30

Val Asp Leu Arg Gly Arg Glu Val Glu Val Leu Gly Glu Val Pro
                35                  40                  45

Ala Ala Gly Gly Ser Pro Leu Arg Gln Tyr Phe Phe Glu Thr Arg
                50                  55                  60

Cys Lys Ala Asp Asn Ala Glu Glu Gly Gly Pro Gly Ala Gly Gly
                65                  70                  75

Gly Gly Arg Gly Val Asp Arg Arg His Trp Val Ser Glu Cys Lys
                80                  85                  90

Ala Lys Gln Ser Tyr Val Arg Ala Leu Thr Ala Asp Ala Gln Gly
                95                 100                 105

Arg Val Gly Trp Arg Trp Ile Arg Ile Asp Thr Ala Cys Val Cys
               110                 115                 120

Thr Leu Leu Ser Arg Thr Gly Arg Ala
               125                 129
```

(2) INFORMATION FOR SEQ ID NO:54:

(i) SEQUENCE CHARACTERISTICS:
        (A) LENGTH: 129 amino acids
        (B) TYPE: amino acid
        (D) TOPOLOGY: linear (xi) SEQUENCE DESCRIPTION: SEQ ID NO:54:

```
Gly Val Ser Glu Thr Ala Pro Ala Ser Arg Arg Gly Glu Leu Ala
 1               5                  10                  15

Val Cys Asp Ala Val Ser Gly Trp Val Thr Asp Arg Arg Thr Ala
                20                  25                  30

Val Asp Leu Arg Gly Arg Glu Val Glu Val Leu Gly Glu Val Pro
                35                  40                  45

Ala Ala Gly Gly Ser Pro Leu Arg Gln Tyr Phe Phe Glu Thr Arg
                50                  55                  60

Lys Ala Asp Asn Ala Glu Glu Gly Gly Pro Gly Ala Gly Gly Gly
                65                  70                  75

Gly Cys Arg Gly Val Asp Arg Arg His Trp Val Ser Glu Cys Lys
                80                  85                  90

Ala Lys Gln Ser Tyr Val Arg Ala Leu Thr Ala Asp Ala Gln Gly
                95                 100                 105

Arg Val Gly Trp Arg Trp Ile Arg Ile Asp Thr Ala Cys Val Cys
               110                 115                 120

Thr Leu Leu Ser Arg Thr Gly Arg Ala
```

125                 129

(2) INFORMATION FOR SEQ ID NO:55:

(i) SEQUENCE CHARACTERISTICS:
        (A) LENGTH: 124 amino acids
        (B) TYPE: amino acid
        (D) TOPOLOGY: linear (xi) SEQUENCE DESCRIPTION: SEQ ID NO:55:

Gly Val Ser Glu Thr Ala Pro Ala Ser Arg Arg Gly Glu Leu Ala
  1               5                  10                  15

Val Cys Asp Ala Val Ser Gly Trp Val Thr Asp Arg Arg Thr Ala
                 20                  25                  30

Val Asp Leu Arg Gly Arg Glu Val Glu Val Leu Gly Glu Val Pro
                 35                  40                  45

Ala Ala Gly Gly Ser Pro Leu Arg Arg Cys Lys Ala Asp Asn Ala
                 50                  55                  60

Glu Glu Gly Gly Pro Gly Ala Gly Gly Gly Cys Arg Gly Val
                 65                  70                  75

Asp Arg Arg His Trp Val Ser Glu Cys Lys Ala Lys Gln Ser Tyr
                 80                  85                  90

Val Arg Ala Leu Thr Ala Asp Ala Gln Gly Arg Val Gly Trp Arg
                 95                 100                 105

Trp Ile Arg Ile Asp Thr Ala Cys Val Cys Thr Leu Leu Ser Arg
                110                 115                 120

Thr Gly Arg Ala
            124

(2) INFORMATION FOR SEQ ID NO:56:

(i) SEQUENCE CHARACTERISTICS:
        (A) LENGTH: 107 amino acids
        (B) TYPE: amino acid
        (D) TOPOLOGY: linear (xi) SEQUENCE DESCRIPTION: SEQ ID NO:56:

Gly Val Ser Glu Thr Ala Pro Ala Ser Arg Arg Gly Glu Leu Ala
  1               5                  10                  15

Val Cys Asp Ala Val Ser Gly Trp Val Thr Asp Arg Arg Thr Ala
                 20                  25                  30

Val Asp Leu Arg Gly Arg Glu Val Glu Val Leu Gly Glu Val Pro
                 35                  40                  45

Ala Ala Gly Gly Ser Pro Leu Arg Gln Tyr Phe Phe Glu Thr Arg
                 50                  55                  60

Arg His Trp Val Ser Glu Cys Lys Ala Lys Gln Ser Tyr Val Arg
                 65                  70                  75

Ala Leu Thr Ala Asp Ala Gln Gly Arg Val Gly Trp Arg Trp Ile
                 80                  85                  90

Arg Ile Asp Thr Ala Cys Val Cys Thr Leu Leu Ser Arg Thr Gly
                 95                 100                 105

Arg Ala
    107

(2) INFORMATION FOR SEQ ID NO:57:

(i) SEQUENCE CHARACTERISTICS:
        (A) LENGTH: 126 amino acids
        (B) TYPE: amino acid (D) TOPOLOGY: linear (xi) SEQUENCE DESCRIPTION: SEQ ID NO:57:

Gly Val Ser Glu Thr Ala Pro Ala Ser Arg Arg Gly Glu Leu Ala
 1               5                  10                  15

Val Cys Asp Ala Val Ser Gly Trp Val Thr Asp Arg Arg Thr Ala
                20                  25                  30

Val Asp Leu Arg Gly Arg Glu Val Glu Val Leu Gly Glu Val Pro
                35                  40                  45

Ala Ala Gly Gly Ser Pro Leu Arg Gln Tyr Phe Phe Glu Thr Arg
                50                  55                  60

Cys Lys Ala Asp Asn Ala Glu Glu Gly Pro Gly Ala Gly Gly
65                  70                  75

Gly Gly Cys Arg Gly Val Asp Arg Arg Glu Cys Lys Ala Lys Gln
                80                  85                  90

Ser Tyr Val Arg Ala Leu Thr Ala Asp Ala Gln Gly Arg Val Gly
                95                  100                 105

Trp Arg Trp Ile Arg Ile Asp Thr Ala Cys Val Cys Thr Leu Leu
                110                 115                 120

Ser Arg Thr Gly Arg Ala
                125 126

(2) INFORMATION FOR SEQ ID NO:58:

(i) SEQUENCE CHARACTERISTICS:
        (A) LENGTH: 114 amino acids
        (B) TYPE: amino acid
        (D) TOPOLOGY: linear (xi) SEQUENCE DESCRIPTION: SEQ ID NO:58:

Gly Val Ser Glu Thr Ala Pro Ala Ser Arg Arg Gly Glu Leu Ala
 1               5                  10                  15

Val Cys Asp Ala Val Ser Gly Trp Val Thr Asp Arg Arg Thr Ala
                20                  25                  30

Val Asp Leu Arg Gly Arg Glu Val Glu Val Leu Gly Glu Val Pro
                35                  40                  45

Ala Ala Gly Gly Ser Pro Leu Arg Gln Tyr Phe Phe Glu Thr Arg
                50                  55                  60

Cys Lys Ala Asp Asn Ala Glu Glu Gly Pro Gly Ala Gly Gly
65                  70                  75

Gly Gly Cys Arg Gly Val Asp Arg Arg His Ala Asp Ala Gln Gly
                80                  85                  90

Arg Val Gly Trp Arg Trp Ile Arg Ile Asp Thr Ala Cys Val Cys
                95                  100                 105

Thr Leu Leu Ser Arg Thr Gly Arg Ala
                110                 114

(2) INFORMATION FOR SEQ ID NO:59:

(i) SEQUENCE CHARACTERISTICS:
        (A) LENGTH: 130 amino acids
        (B) TYPE: amino acid
        (D) TOPOLOGY: linear (xi) SEQUENCE DESCRIPTION: SEQ ID NO:59:

Gly Val Ser Glu Thr Ala Pro Ala Ser Arg Arg Gly Glu Leu Ala
 1               5                  10                  15

Val Cys Asp Ala Val Ser Gly Trp Val Thr Asp Arg Arg Thr Ala

```
                    20                  25                  30

Val Asp Leu Arg Gly Arg Glu Val Glu Val Leu Gly Glu Val Pro
                    35                  40                  45

Ala Ala Gly Gly Ser Pro Leu His Gln Tyr Phe Phe Glu Thr Arg
                    50                  55                  60

Cys Lys Ala Asp Asn Ala Glu Glu Gly Pro Gly Ala Gly Gly
                65                  70                  75

Gly Gly Cys Arg Gly Val Asp Arg Arg His Trp Val Ser Glu Cys
                    80                  85                  90

Lys Ala Lys Gln Ser Tyr Val Arg Ala Leu Thr Ala Asp Ala Gln
                    95                 100                 105

Gly Arg Val Gly Trp Arg Trp Ile Arg Ile Asp Thr Ala Cys Val
                   110                 115                 120

Cys Thr Leu Leu Ser Arg Thr Gly Arg Ala
                   125                 130

(2) INFORMATION FOR SEQ ID NO:60:

(i) SEQUENCE CHARACTERISTICS:
        (A) LENGTH: 130 amino acids
        (B) TYPE: amino acid
        (D) TOPOLOGY: linear (xi) SEQUENCE DESCRIPTION: SEQ ID NO:60:

Gly Val Ser Glu Thr Ala Pro Ala Ser Arg Arg Gly Glu Leu Ala
  1               5                  10                  15

Val Cys Asp Ala Val Ser Gly Trp Val Thr Asp Arg Arg Thr Ala
                    20                  25                  30

Val Asp Leu Arg Gly Arg Glu Val Glu Val Leu Gly Glu Val Pro
                    35                  40                  45

Ala Ala Gly Gly Ser Pro Leu Arg Gln Tyr Phe Phe Glu Thr Arg
                    50                  55                  60

Cys Lys Ala Asp Asn Ala Glu Glu Gly Pro Gly Ala Gly Gly
                65                  70                  75

Gly Gly Cys Arg Gly Val Asp Arg Arg His Trp Val Ser Glu Cys
                    80                  85                  90

His Ala Lys Gln Ser Tyr Val Arg Ala Leu Thr Ala Asp Ala Gln
                    95                 100                 105

Gly Arg Val Gly Trp Arg Trp Ile Arg Ile Asp Thr Ala Cys Val
                   110                 115                 120

Cys Thr Leu Leu Ser Arg Thr Gly Arg Ala
                   125                 130

(2) INFORMATION FOR SEQ ID NO:61:

(i) SEQUENCE CHARACTERISTICS:
        (A) LENGTH: 130 amino acids
        (B) TYPE: amino acid
        (D) TOPOLOGY: linear (xi) SEQUENCE DESCRIPTION: SEQ ID NO:61:

Gly Val Ser Glu Thr Ala Pro Ala Ser Arg Arg Gly Glu Leu Ala
  1               5                  10                  15

Val Cys Asp Ala Val Ser Gly Trp Val Thr Asp Arg Arg Thr Ala
                    20                  25                  30

Val Asp Leu Arg Gly Arg Glu Val Glu Val Leu Gly Glu Val Pro
                    35                  40                  45
```

```
Ala Ala Gly Gly Ser Pro Leu Arg Gln Tyr Phe Glu Thr Arg
            50                  55                  60

Cys Lys Ala Asp Asn Ala Glu Glu Gly Gly Pro Gly Ala Gly Gly
                65                  70                  75

Gly Gly Cys Arg Gly Val Asp Arg Arg His Trp Val Ser Glu Cys
            80                  85                  90

Lys Ala Lys Gln Ser Tyr Val Arg Ala Leu Thr Ala Asp Ala Gln
            95                  100                 105

Gly Arg Phe Gly Trp Arg Trp Ile Arg Ile Asp Thr Ala Cys Val
            110                 115                 120

Cys Thr Leu Leu Ser Arg Thr Gly Arg Ala
            125                 130
```

(2) INFORMATION FOR SEQ ID NO:62:

(i) SEQUENCE CHARACTERISTICS:
        (A) LENGTH: 130 amino acids
        (B) TYPE: amino acid
        (D) TOPOLOGY: linear (xi) SEQUENCE DESCRIPTION: SEQ ID NO:62:

```
Gly Val Ser Glu Thr Ala Pro Ala Ser Arg Arg Gly Glu Leu Ala
1               5                   10                  15

Val Cys Asp Ala Val Ser Gly Trp Val Thr Asp Arg Arg Thr Ala
            20                  25                  30

Val Asp Leu Arg Gly Arg Glu Val Glu Val Leu Gly Glu Val Pro
            35                  40                  45

Ala Ala Gly Gly Ser Pro Leu Arg Gln Tyr Phe Phe Glu Thr Arg
            50                  55                  60

Cys Lys Ala Asp Asn Ala Glu Glu Gly Gly Pro Gly Ala Gly Gly
            65                  70                  75

Gly Gly Cys Arg Gly Val Asp Arg Gln His Trp Val Ser Glu Cys
            80                  85                  90

Lys Ala Lys Gln Ser Tyr Val Arg Ala Leu Thr Ala Asp Ala Gln
            95                  100                 105

Gly Arg Val Gly Trp Arg Trp Ile Arg Ile Asp Thr Ala Cys Val
            110                 115                 120

Cys Thr Leu Leu Ser Arg Thr Gly Arg Ala
            125                 130
```

(2) INFORMATION FOR SEQ ID NO:63:

(i) SEQUENCE CHARACTERISTICS:
        (A) LENGTH: 130 amino acids
        (B) TYPE: amino acid
        (D) TOPOLOGY: linear (xi) SEQUENCE DESCRIPTION: SEQ ID NO:63:

```
Gly Val Ser Glu Thr Ala Pro Ala Ser Arg Arg Gly Glu Leu Ala
1               5                   10                  15

Val Cys Asp Ala Val Ser Gly Trp Val Thr Asp Arg Arg Thr Ala
            20                  25                  30

Val Asp Leu Arg Gly Arg Glu Val Glu Val Leu Gly Glu Val Pro
            35                  40                  45

Ala Ala Gly Gly Ser Pro Leu Arg Gln Tyr Phe Phe Glu Thr Arg
            50                  55                  60

Cys Lys Ala Asp Asn Ala Glu Glu Gly Gly Pro Gly Ala Gly Gly
            65                  70                  75
```

Gly Gly Cys Arg Gly Val Asp Arg His His Trp Val Ser Glu Cys
            80                  85                  90

Lys Ala Lys Gln Ser Tyr Val Arg Ala Leu Thr Ala Asp Ala Gln
            95                  100                 105

Gly Arg Val Gly Trp Arg Trp Ile Arg Ile Asp Thr Ala Cys Val
            110                 115                 120

Cys Thr Leu Leu Ser Arg Thr Gly Arg Ala
            125                 130

(2) INFORMATION FOR SEQ ID NO:64:

(i) SEQUENCE CHARACTERISTICS:
        (A) LENGTH: 130 amino acids
        (B) TYPE: amino acid
        (D) TOPOLOGY: linear (xi) SEQUENCE DESCRIPTION: SEQ ID NO:64:

Gly Val Ser Glu Thr Ala Pro Ala Ser Arg Arg Gly Glu Leu Ala
 1               5                  10                  15

Val Cys Asp Ala Val Ser Gly Trp Val Thr Asp Arg Arg Thr Ala
            20                  25                  30

Val Asp Leu Arg Gly Arg Glu Val Glu Val Leu Gly Glu Val Pro
            35                  40                  45

Ala Ala Gly Gly Ser Pro Leu Arg Gln Tyr Phe Phe Glu Thr Arg
            50                  55                  60

Cys Lys Ala Asp Asn Ala Glu Glu Gly Pro Gly Ala Gly Gly
            65                  70                  75

Gly Gly Cys Arg Gly Val Asp Arg Asn His Trp Val Ser Glu Cys
            80                  85                  90

Lys Ala Lys Gln Ser Tyr Val Arg Ala Leu Thr Ala Asp Ala Gln
            95                  100                 105

Gly Arg Val Gly Trp Arg Trp Ile Arg Ile Asp Thr Ala Cys Val
            110                 115                 120

Cys Thr Leu Leu Ser Arg Thr Gly Arg Ala
            125                 130

(2) INFORMATION FOR SEQ ID NO:65:

(i) SEQUENCE CHARACTERISTICS:
        (A) LENGTH: 130 amino acids
        (B) TYPE: amino acid
        (D) TOPOLOGY: linear (xi) SEQUENCE DESCRIPTION: SEQ ID NO:65:

Gly Val Ser Glu Thr Ala Pro Ala Ser Arg Arg Gly Glu Leu Ala
 1               5                  10                  15

Val Cys Asp Ala Val Ser Gly Trp Val Thr Asp Arg Arg Thr Ala
            20                  25                  30

Val Asp Leu Arg Gly Arg Glu Val Glu Val Leu Gly Glu Val Pro
            35                  40                  45

Ala Ala Gly Gly Ser Pro Leu Arg Gln Tyr Phe Phe Glu Thr Arg
            50                  55                  60

Cys Lys Ala Asp Asn Ala Glu Glu Gly Pro Gly Ala Gly Gly
            65                  70                  75

Gly Gly Cys Arg Gly Val Asp Arg Thr His Trp Val Ser Glu Cys
            80                  85                  90

Lys Ala Lys Gln Ser Tyr Val Arg Ala Leu Thr Ala Asp Ala Gln

```
                95                 100                105

Gly Arg Val Gly Trp Arg Trp Ile Arg Ile Asp Thr Ala Cys Val
                110                115                120

Cys Thr Leu Leu Ser Arg Thr Gly Arg Ala
                125                130

(2) INFORMATION FOR SEQ ID NO:66:

(i) SEQUENCE CHARACTERISTICS:
        (A) LENGTH: 130 amino acids
        (B) TYPE: amino acid
        (D) TOPOLOGY: linear (xi) SEQUENCE DESCRIPTION: SEQ ID NO:66:

Gly Val Ser Glu Thr Ala Pro Ala Ser Arg Arg Gly Glu Leu Ala
 1               5                  10                 15

Val Cys Asp Ala Val Ser Gly Trp Val Thr Asp Arg Arg Thr Ala
                20                 25                 30

Val Asp Leu Arg Gly Arg Glu Val Glu Val Leu Gly Glu Val Pro
                35                 40                 45

Ala Ala Gly Gly Ser Pro Leu Arg Gln Tyr Phe Phe Glu Thr Arg
                50                 55                 60

Cys Lys Ala Asp Asn Ala Glu Glu Gly Gly Pro Gly Ala Gly Gly
                65                 70                 75

Gly Gly Cys Arg Gly Val Asp Arg Tyr His Trp Val Ser Glu Cys
                80                 85                 90

Lys Ala Lys Gln Ser Tyr Val Arg Ala Leu Thr Ala Asp Ala Gln
                95                 100                105

Gly Arg Val Gly Trp Arg Trp Ile Arg Ile Asp Thr Ala Cys Val
                110                115                120

Cys Thr Leu Leu Ser Arg Thr Gly Arg Ala
                125                130

(2) INFORMATION FOR SEQ ID NO:67:

(i) SEQUENCE CHARACTERISTICS:
        (A) LENGTH: 130 amino acids
        (B) TYPE: amino acid
        (D) TOPOLOGY: linear (xi) SEQUENCE DESCRIPTION: SEQ ID NO:67:

Gly Val Ser Glu Thr Ala Pro Ala Ser Arg Arg Gly Glu Leu Ala
 1               5                  10                 15

Val Cys Asp Ala Val Ser Gly Trp Val Thr Asp Arg Arg Thr Ala
                20                 25                 30

Val Asp Leu Arg Gly Arg Glu Val Glu Val Leu Gly Glu Val Pro
                35                 40                 45

Ala Ala Gly Gly Ser Pro Leu Arg Gln Tyr Phe Phe Glu Thr Arg
                50                 55                 60

Cys Lys Ala Asp Asn Ala Glu Glu Gly Gly Pro Gly Ala Gly Gly
                65                 70                 75

Gly Gly Cys Arg Gly Val Asp Arg Trp His Trp Val Ser Glu Cys
                80                 85                 90

Lys Ala Lys Gln Ser Tyr Val Arg Ala Leu Thr Ala Asp Ala Gln
                95                 100                105

Gly Arg Val Gly Trp Arg Trp Ile Arg Ile Asp Thr Ala Cys Val
                110                115                120
```

Cys Thr Leu Leu Ser Arg Thr Gly Arg Ala
            125                 130

(2) INFORMATION FOR SEQ ID NO:68:

(i) SEQUENCE CHARACTERISTICS:
        (A) LENGTH: 130 amino acids
        (B) TYPE: amino acid
        (D) TOPOLOGY: linear (xi) SEQUENCE DESCRIPTION: SEQ ID NO:68:

Gly Val Ser Glu Thr Ala Pro Ala Ser Arg Arg Gly Glu Leu Ala
 1               5                  10                  15

Val Cys Asp Ala Val Ser Gly Trp Val Thr Asp Arg Arg Thr Ala
                20                  25                  30

Val Asp Leu Arg Gly Arg Glu Val Glu Val Leu Gly Glu Val Pro
                35                  40                  45

Ala Ala Gly Gly Ser Pro Leu Arg Gln Tyr Phe Phe Glu Thr Arg
                50                  55                  60

Cys Lys Ala Asp Asn Ala Glu Glu Gly Gly Pro Gly Ala Gly Gly
                65                  70                  75

Gly Gly Cys Arg Gly Val Asp Arg Arg His Trp Val Ser Glu Cys
                80                  85                  90

Lys Ala Lys Gln Ser Tyr Val Arg Ala Leu Thr Ala Asp Ala Gln
                95                  100                 105

Gly Arg Val Gly Trp Arg Trp Ile Arg Ile Glu Thr Ala Cys Val
                110                 115                 120

Cys Thr Leu Leu Ser Arg Thr Gly Arg Ala
            125                 130

(2) INFORMATION FOR SEQ ID NO:69:

(i) SEQUENCE CHARACTERISTICS:
        (A) LENGTH: 130 amino acids
        (B) TYPE: amino acid
        (D) TOPOLOGY: linear (xi) SEQUENCE DESCRIPTION: SEQ ID NO:69:

Gly Val Ser Glu Thr Ala Pro Ala Ser Arg Arg Gly Glu Leu Ala
 1               5                  10                  15

Val Cys Asp Ala Val Ser Gly Trp Val Thr Asp Arg Arg Thr Ala
                20                  25                  30

Val Asp Leu Arg Gly Arg Glu Val Glu Val Leu Gly Glu Val Pro
                35                  40                  45

Ala Ala Gly Gly Ser Pro Leu Arg Gln Tyr Phe Phe Glu Thr Arg
                50                  55                  60

Cys Lys Ala Asp Asn Ala Glu Glu Gly Gly Pro Gly Ala Gly Gly
                65                  70                  75

Gly Gly Cys Arg Gly Val Asp Arg Arg His Trp Val Ser Glu Cys
                80                  85                  90

Lys Ala Lys Gln Ser Tyr Val Arg Ala Leu Thr Ala Asp Ala Gln
                95                  100                 105

Gly Arg Val Gly Trp Arg Trp Ile Arg Ile Asn Thr Ala Cys Val
                110                 115                 120

Cys Thr Leu Leu Ser Arg Thr Gly Arg Ala
            125                 130

(2) INFORMATION FOR SEQ ID NO:70:

(i) SEQUENCE CHARACTERISTICS:
        (A) LENGTH: 130 amino acids
        (B) TYPE: amino acid
        (D) TOPOLOGY: linear (xi) SEQUENCE DESCRIPTION: SEQ ID NO:70:

Gly Val Ser Glu Thr Ala Pro Ala Ser Arg Arg Gly Glu Leu Ala
 1               5                  10                  15

Val Cys Asp Ala Val Ser Gly Trp Val Thr Asp Arg Arg Thr Ala
                20                  25                  30

Val Asp Leu Arg Gly Arg Glu Val Glu Val Leu Gly Glu Val Pro
                35                  40                  45

Ala Ala Gly Gly Ser Pro Leu Arg Gln Tyr Phe Phe Glu Thr Arg
                50                  55                  60

Cys Lys Ala Asp Asn Ala Glu Glu Gly Pro Gly Ala Gly Gly
                65                  70                  75

Gly Gly Cys Arg Gly Val Asp Arg Arg His Trp Val Ser Glu Cys
                80                  85                  90

Lys Ala Lys Gln Ser Tyr Val Arg Ala Leu Thr Ala Asp Ala Gln
                95                  100                 105

Gly Arg Val Gly Trp Arg Trp Ile Arg Ile Gln Thr Ala Cys Val
                110                 115                 120

Cys Thr Leu Leu Ser Arg Thr Gly Arg Ala
                125                 130

(2) INFORMATION FOR SEQ ID NO:71:

(i) SEQUENCE CHARACTERISTICS:
        (A) LENGTH: 130 amino acids
        (B) TYPE: amino acid
        (D) TOPOLOGY: linear (xi) SEQUENCE DESCRIPTION: SEQ ID NO:71:

Gly Val Ser Glu Thr Ala Pro Ala Ser Arg Arg Gly Glu Leu Ala
 1               5                  10                  15

Val Cys Asp Ala Val Ser Gly Trp Val Thr Asp Arg Arg Thr Ala
                20                  25                  30

Val Asp Leu Arg Gly Arg Glu Val Glu Val Leu Gly Glu Val Pro
                35                  40                  45

Ala Ala Gly Gly Ser Pro Leu Arg Gln Tyr Phe Phe Glu Thr Arg
                50                  55                  60

Cys Lys Ala Asp Asn Ala Glu Glu Gly Pro Gly Ala Gly Gly
                65                  70                  75

Gly Gly Cys Arg Gly Val Asp Arg Arg His Trp Val Ser Glu Cys
                80                  85                  90

Lys Ala Lys Gln Ser Tyr Val Arg Ala Leu Thr Ala Asp Ala Gln
                95                  100                 105

Gly Arg Val Gly Trp Arg Trp Ile Arg Ile Tyr Thr Ala Cys Val
                110                 115                 120

Cys Thr Leu Leu Ser Arg Thr Gly Arg Ala
                125                 130

(2) INFORMATION FOR SEQ ID NO:72:

(i) SEQUENCE CHARACTERISTICS:
        (A) LENGTH: 130 amino acids
        (B) TYPE: amino acid
        (D) TOPOLOGY: linear (xi) SEQUENCE DESCRIPTION: SEQ ID NO:72:

Gly Val Ser Glu Thr Ala Pro Ala Ser Arg Arg Gly Glu Leu Ala
1               5                   10                  15

Val Cys Asp Ala Val Ser Gly Trp Val Thr Asp Arg Arg Thr Ala
                20                  25                  30

Val Asp Leu Arg Gly Arg Glu Val Glu Val Leu Gly Glu Val Pro
                35                  40                  45

Ala Ala Gly Gly Ser Pro Leu Arg Gln Tyr Phe Phe Glu Thr Arg
                50                  55                  60

Cys Lys Ala Asp Asn Ala Glu Glu Gly Pro Gly Ala Gly Gly
                65                  70                  75

Gly Gly Cys Arg Gly Val Asp Arg Arg His Trp Val Ser Glu Cys
                80                  85                  90

Lys Ala Lys Gln Ser Tyr Val Arg Ala Leu Thr Ala Asp Ala Gln
                95                  100                 105

Gly Arg Val Gly Trp Arg Trp Ile Arg Ile Ser Thr Ala Cys Val
                110                 115                 120

Cys Thr Leu Leu Ser Arg Thr Gly Arg Ala
                125                 130

(2) INFORMATION FOR SEQ ID NO:73:

(i) SEQUENCE CHARACTERISTICS:
        (A) LENGTH: 130 amino acids
        (B) TYPE: amino acid
        (D) TOPOLOGY: linear (xi) SEQUENCE DESCRIPTION: SEQ ID NO:73:

Gly Val Ser Glu Thr Ala Pro Ala Ser Arg Arg Gly Glu Leu Ala
1               5                   10                  15

Val Cys Asp Ala Val Ser Gly Trp Val Thr Asp Arg Arg Thr Ala
                20                  25                  30

Val Asp Leu Arg Gly Arg Glu Val Glu Val Leu Gly Glu Val Pro
                35                  40                  45

Ala Ala Gly Gly Ser Pro Leu Arg Gln Tyr Phe Phe Glu Thr Arg
                50                  55                  60

Cys Lys Ala Asp Asn Ala Glu Glu Gly Pro Gly Ala Gly Gly
                65                  70                  75

Gly Gly Cys Arg Gly Val Asp Arg Arg His Trp Val Ser Glu Cys
                80                  85                  90

Lys Ala Lys Gln Ser Tyr Val Arg Ala Leu Thr Ala Asp Ala Gln
                95                  100                 105

Gly Arg Val Gly Trp Arg Trp Ile Arg Ile Thr Thr Ala Cys Val
                110                 115                 120

Cys Thr Leu Leu Ser Arg Thr Gly Arg Ala
                125                 130

(2) INFORMATION FOR SEQ ID NO:74:

(i) SEQUENCE CHARACTERISTICS:
        (A) LENGTH: 4 amino acids
        (B) TYPE: amino acid
        (D) TOPOLOGY: linear (xi) SEQUENCE DESCRIPTION: SEQ ID NO:74:

Ile Lys Thr Gly
1           4

(2) INFORMATION FOR SEQ ID NO:75:

(i) SEQUENCE CHARACTERISTICS:
        (A) LENGTH: 5 amino acids
        (B) TYPE: amino acid
        (D) TOPOLOGY: linear (xi) SEQUENCE DESCRIPTION: SEQ ID NO:75:

Glu Ile Lys Thr Gly
 1           5

(2) INFORMATION FOR SEQ ID NO:76:

(i) SEQUENCE CHARACTERISTICS:
        (A) LENGTH: 6 amino acids
        (B) TYPE: amino acid
        (D) TOPOLOGY: linear (xi) SEQUENCE DESCRIPTION: SEQ ID NO:76:

Glu Ile Lys Thr Gly Asn
 1           5   6

(2) INFORMATION FOR SEQ ID NO:77:

(i) SEQUENCE CHARACTERISTICS:
        (A) LENGTH: 4 amino acids
        (B) TYPE: amino acid
        (D) TOPOLOGY: linear (xi) SEQUENCE DESCRIPTION: SEQ ID NO:77:

Ser Pro Val Lys
 1           4

(2) INFORMATION FOR SEQ ID NO:78:

(i) SEQUENCE CHARACTERISTICS:
        (A) LENGTH: 4 amino acids
        (B) TYPE: amino acid
        (D) TOPOLOGY: linear (xi) SEQUENCE DESCRIPTION: SEQ ID NO:78:

Lys Ser Ser Ala
 1           4

(2) INFORMATION FOR SEQ ID NO:79:

(i) SEQUENCE CHARACTERISTICS:
        (A) LENGTH: 6 amino acids
        (B) TYPE: amino acid
        (D) TOPOLOGY: linear (xi) SEQUENCE DESCRIPTION: SEQ ID NO:79:

Tyr Ala Glu His Lys Ser
 1           5   6

(2) INFORMATION FOR SEQ ID NO:80:

(i) SEQUENCE CHARACTERISTICS:
        (A) LENGTH: 7 amino acids
        (B) TYPE: amino acid
        (D) TOPOLOGY: linear (xi) SEQUENCE DESCRIPTION: SEQ ID NO:80:

Arg Tyr Ala Glu His Lys Ser
 1           5      7

(2) INFORMATION FOR SEQ ID NO:81:

(i) SEQUENCE CHARACTERISTICS:
        (A) LENGTH: 8 amino acids
        (B) TYPE: amino acid
        (D) TOPOLOGY: linear (xi) SEQUENCE DESCRIPTION: SEQ ID NO:81:

```
Arg Tyr Ala Glu His Lys Ser His
 1               5               8
```

(2) INFORMATION FOR SEQ ID NO:82:

(i) SEQUENCE CHARACTERISTICS:
        (A) LENGTH: 7 amino acids
        (B) TYPE: amino acid
        (D) TOPOLOGY: linear (xi) SEQUENCE DESCRIPTION: SEQ ID NO:82:

```
Tyr Ala Glu His Lys Ser His
 1               5       7
```

(2) INFORMATION FOR SEQ ID NO:83:

(i) SEQUENCE CHARACTERISTICS:
        (A) LENGTH: 5 amino acids
        (B) TYPE: amino acid
        (D) TOPOLOGY: linear (xi) SEQUENCE DESCRIPTION: SEQ ID NO:83:

```
Ala Asn Arg Thr Ser
 1               5
```

(2) INFORMATION FOR SEQ ID NO:84:

(i) SEQUENCE CHARACTERISTICS:
        (A) LENGTH: 4 amino acids
        (B) TYPE: amino acid
        (D) TOPOLOGY: linear (xi) SEQUENCE DESCRIPTION: SEQ ID NO:84:

```
Ala Asn Arg Thr
 1           4
```

(2) INFORMATION FOR SEQ ID NO:85:

(i) SEQUENCE CHARACTERISTICS:
        (A) LENGTH: 4 amino acids
        (B) TYPE: amino acid
        (D) TOPOLOGY: linear (xi) SEQUENCE DESCRIPTION: SEQ ID NO:85:

```
Asn Arg Thr Ser
 1           4
```

(2) INFORMATION FOR SEQ ID NO:86:

(i) SEQUENCE CHARACTERISTICS:
        (A) LENGTH: 4 amino acids
        (B) TYPE: amino acid
        (D) TOPOLOGY: linear (xi) SEQUENCE DESCRIPTION: SEQ ID NO:86:

```
Lys Glu Ala Arg
 1           4
```

(2) INFORMATION FOR SEQ ID NO:87:

(i) SEQUENCE CHARACTERISTICS:
        (A) LENGTH: 5 amino acids
        (B) TYPE: amino acid
        (D) TOPOLOGY: linear (xi) SEQUENCE DESCRIPTION: SEQ ID NO:87:

Lys Glu Ala Arg Pro
 1               5

(2) INFORMATION FOR SEQ ID NO:88:

(i) SEQUENCE CHARACTERISTICS:
        (A) LENGTH: 4 amino acids
        (B) TYPE: amino acid
        (D) TOPOLOGY: linear (xi) SEQUENCE DESCRIPTION: SEQ ID NO:88:

Ile Asp Asp Lys
 1           4

(2) INFORMATION FOR SEQ ID NO:89:

(i) SEQUENCE CHARACTERISTICS:
        (A) LENGTH: 4 amino acids
        (B) TYPE: amino acid
        (D) TOPOLOGY: linear (xi) SEQUENCE DESCRIPTION: SEQ ID NO:89:

Ser Glu Asn Asn
 1           4

(2) INFORMATION FOR SEQ ID NO:90:

(i) SEQUENCE CHARACTERISTICS:
        (A) LENGTH: 5 amino acids
        (B) TYPE: amino acid
        (D) TOPOLOGY: linear (xi) SEQUENCE DESCRIPTION: SEQ ID NO:90:

Thr Ser Glu Asn Asn
 1               5

(2) INFORMATION FOR SEQ ID NO:91:

(i) SEQUENCE CHARACTERISTICS:
        (A) LENGTH: 6 amino acids
        (B) TYPE: amino acid
        (D) TOPOLOGY: linear (xi) SEQUENCE DESCRIPTION: SEQ ID NO:91:

Thr Ser Glu Asn Asn Lys
 1               5   6

(2) INFORMATION FOR SEQ ID NO:92:

(i) SEQUENCE CHARACTERISTICS:
        (A) LENGTH: 4 amino acids
        (B) TYPE: amino acid
        (D) TOPOLOGY: linear (xi) SEQUENCE DESCRIPTION: SEQ ID NO:92:

Lys Leu Val Gly
 1           4

(2) INFORMATION FOR SEQ ID NO:93:

(i) SEQUENCE CHARACTERISTICS:
    (A) LENGTH: 47 amino acids
    (B) TYPE: amino acid
    (D) TOPOLOGY: linear (xi) SEQUENCE DESCRIPTION: SEQ ID NO:93:

```
Cys Cys Gly Cys Gly Cys Gly Cys Thr Cys Thr Ala Gly Ala Gly
  1               5                  10                  15

Thr Cys Gly Ala Cys Ala Ala Gly Cys Ala Gly Thr Ala Cys Thr
                 20                  25                  30

Thr Cys Thr Ala Thr Gly Ala Gly Ala Cys Gly Ala Ala Gly Thr
                 35                  40                  45

Gly Thr
     47
```

(2) INFORMATION FOR SEQ ID NO:94:

(i) SEQUENCE CHARACTERISTICS:
        (A) LENGTH: 47 amino acids
        (B) TYPE: amino acid
        (D) TOPOLOGY: linear (xi) SEQUENCE DESCRIPTION: SEQ ID NO:94:

```
Cys Cys Gly Cys Gly Cys Gly Cys Thr Cys Thr Ala Gly Ala Gly
  1               5                  10                  15

Thr Cys Gly Ala Cys Ala Ala Ala Cys Ala Ala Thr Ala Thr Thr
                 20                  25                  30

Thr Thr Thr Thr Cys Gly Ala Ala Ala Cys Cys Cys Gly Ala Thr
                 35                  40                  45

Gly Cys
     47
```

(2) INFORMATION FOR SEQ ID NO:95:

(i) SEQUENCE CHARACTERISTICS:
        (A) LENGTH: 47 amino acids
        (B) TYPE: amino acid
        (D) TOPOLOGY: linear (xi) SEQUENCE DESCRIPTION: SEQ ID NO:95:

```
Cys Cys Gly Cys Gly Cys Gly Cys Thr Cys Thr Ala Gly Ala Gly
  1               5                  10                  15

Thr Cys Gly Ala Cys Ala Ala Gly Cys Ala Gly Thr Ala Cys Thr
                 20                  25                  30

Thr Cys Thr Ala Thr Gly Ala Gly Ala Cys Thr Ala Ala Gly Thr
                 35                  40                  45

Gly Thr
     47
```

(2) INFORMATION FOR SEQ ID NO:96:

(i) SEQUENCE CHARACTERISTICS:
        (A) LENGTH: 47 amino acids
        (B) TYPE: amino acid
        (D) TOPOLOGY: linear (xi) SEQUENCE DESCRIPTION: SEQ ID NO:96:

```
Cys Cys Gly Cys Gly Cys Gly Cys Thr Cys Thr Ala Gly Ala Gly
  1               5                  10                  15

Thr Cys Gly Ala Cys Ala Ala Gly Cys Ala Gly Thr Ala Cys Thr
                 20                  25                  30
```

Thr Cys Thr Ala Thr Gly Ala Gly Ala Cys Ala Ala Ala Gly Thr
                 35                  40                  45

Gly Thr
    47

(2) INFORMATION FOR SEQ ID NO:97:

(i) SEQUENCE CHARACTERISTICS:
        (A) LENGTH: 45 amino acids
        (B) TYPE: amino acid
        (D) TOPOLOGY: linear (xi) SEQUENCE DESCRIPTION: SEQ ID NO:97:

Cys Gly Gly Cys Thr Cys Ala Gly Gly Gly Cys Cys Gly Ala Ala
  1               5                  10                  15

Thr Thr Cys Gly Cys Ala Cys Ala Cys Gly Cys Ala Gly Gly Ala
                 20                  25                  30

Ala Gly Thr Ala Thr Cys Thr Ala Thr Cys Cys Thr Thr Ala Thr
                 35                  40                  45

(2) INFORMATION FOR SEQ ID NO:98:

(i) SEQUENCE CHARACTERISTICS:
        (A) LENGTH: 45 amino acids
        (B) TYPE: amino acid
        (D) TOPOLOGY: linear (xi) SEQUENCE DESCRIPTION: SEQ ID NO:98:

Cys Gly Gly Cys Thr Cys Ala Gly Gly Gly Cys Cys Gly Ala Ala
  1               5                  10                  15

Thr Thr Cys Ala Cys Ala Thr Ala Cys Ala Cys Ala Ala Gly Cys
                 20                  25                  30

Gly Gly Thr Gly Thr Cys Ala Ala Thr Thr Cys Gly Gly Ala Thr
                 35                  40                  45

(2) INFORMATION FOR SEQ ID NO:99:

(i) SEQUENCE CHARACTERISTICS:
        (A) LENGTH: 45 amino acids
        (B) TYPE: amino acid
        (D) TOPOLOGY: linear (xi) SEQUENCE DESCRIPTION: SEQ ID NO:99:

Cys Gly Gly Cys Thr Cys Ala Gly Gly Gly Cys Cys Gly Ala Ala
  1               5                  10                  15

Thr Thr Cys Gly Cys Ala Gly Ala Cys Gly Cys Ala Gly Gly Ala
                 20                  25                  30

Thr Gly Thr Ala Thr Cys Gly Ala Thr Gly Cys Thr Ala Ala Thr
                 35                  40                  45

(2) INFORMATION FOR SEQ ID NO:100:

(i) SEQUENCE CHARACTERISTICS:
        (A) LENGTH: 45 amino acids
        (B) TYPE: amino acid
        (D) TOPOLOGY: linear (xi) SEQUENCE DESCRIPTION: SEQ ID NO:100:

Cys Gly Gly Cys Thr Cys Ala Gly Gly Gly Cys Cys Gly Ala Ala

-continued

```
            1               5              10              15
Thr Thr Cys Gly Cys Ala Ala Ala Cys Gly Cys Ala Gly Gly Ala
                       20              25              30
Thr Gly Thr Ala Thr Cys Gly Ala Thr Gly Cys Thr Ala Ala Thr
                       35              40              45
```

NEUROTROPHIC FACTOR

This is a divisional of co-pending application(s) U.S. Ser. No. 08/426,419 filed on Apr. 19, 1995, now abandoned which was a continuation of application U.S. Ser. No. 08/030,013, filed Mar. 22, 1993, now abandoned which is a 371 of PCT/US91/06950 filed Sep. 24, 1991, which was a continuation-in-part application of U.S. Ser. No. 07/648,482, filed Jan. 31, 1991, now abandoned which was a continuation-in-part application of U.S. Ser. No. 07/587,707, filed Sep. 25, 1990, now U.S. Pat. No. 5,364,769 which applications are incorporated herein by reference and to which applications priority is claimed under 35 USC § 120.

FIELD OF THE INVENTION

This application relates to proteins which are involved in the growth, regulation or maintenance of nervous tissue. In particular, it relates to a nerve-derived factors having homology to NGF.

BACKGROUND OF THE INVENTION

Nerve growth factor (NGF) is a protein which has prominent effects on developing sensory and sympathetic neurons of the peripheral nervous system. NGF acts via specific cell surface receptors on responsive neurons to support neuronal survival, promote neurite outgrowth, and enhance neurochemical differentiation. NGF actions are accompanied by alterations in neuronal membranes (Connolly et al., 1981, J. Cell. Biol: 90:176; Skaper and Varon, 1980, Brain Res. 197:379), in the state of phosphorylation of neuronal proteins (Yu, et al., 1980, J. Biol. Chem. 255:10481; Haleqoua and Patrick, 1980, Cell 22:571), and in the abundance of certain mRNAs and proteins likely to play a role in neuronal differentiation and function (Tiercy and Shooter, 1986, J. Cell. Biol. 103:2367).

Forebrain cholinergic neurons also respond to NGF and may require NGF for trophic support. (Hefti, 1986, J. Neurosci., 6:2155). Indeed, the distribution and ontogenesis of NGF and its receptor in the central nervous system (CNS) suggest that NGF acts as a target-derived neurotrophic factor for basal forebrain cholinergic neurons (Korsching, November/December 1986, Trends in Neuro. Sci., pp 570–573).

While a number of animal homologues to NGF have become known, it was not until recently that an apparently distinct nerve growth factor was identified that nonetheless bears some homology to NGF (Leibrock et al., 1989, Nature 341:149). This factor, called brain-derived neurotropic factor (BDNF), now also called NT-2, was purified from pig brain, and a partial amino acid sequence determined both from the N-terminal end and from fragments purified after cleavages. The longest sequence, compiled from several overlapping fragments, was used to synthesize two sets of oligonucleotides that were used to prime the amplification of a pig genomic template using the polymerase chain reaction (PCR). The nucleotide sequence between the two primers was determined and used to synthesize specific primers for further PCRs on a complementary DNA template obtained by reverse transcription of total RNA isolated from the superior colliculus of the pig brain. The nucleotide sequence so obtained contained an opening reading frame coding for a protein of 252 amino acids, starting with the first methionine codon found after four in-frame stop codons. Leibrock, et al. speculate that there is no reason to think that BDNF and NGF should be the only members of a family of neurotropic proteins having in common structural and functional characteristics, and the authors hope that these common structural features could be used to aid the discovery of other members.

More recently, another novel neurotrophic factor closely related to βNGF and BDNF was discovered, called neuronal factor (NF), or neurotrophin-3 (NT-3). (Hohn, et al., 1990, Nature 344:339; Maisonpierre, et al., 1990, Science 247:1446; Rosenthal, et al., 1990, Neuron 4:767. Both BDNF and NT-3 share approximately 50% of their amino acids with βNGF. High levels of mRNA coding for BDNF and NT-3 occur in the adult rodent brain. βNGF, BDNF, and NT-3 support survival of selected populations of chick sensory neurons, suggesting independent roles in the regulation of neuronal survival during development.

Neuronal survival and growth is also affected by growth factors for non-neuronal cells, including fibroblast growth factor (FGF), epidermal growth factor, and insulin-like growth factors. (Morrison, et al., 1987, Science 238:72; Walicke, 1988, J. Neurosci. 8:2618; Bhat, 1983, Dev. Brain Res. 11:315). Basic FGF (bFGF) supports initial survival and subsequent fiber outgrowth of dissociated rodent fetal neurons in culture. While neurons from many brain regions are affected, the proportion of neurons surviving varies among brain regions, suggesting that subpopulations of neurons are responsive to bFGF. (Morrison, et al., 1986, Proc. Natl. Acad. Sci. 83:7537; Walicke, et al., 1986, Proc. Natl. Acad. Sci. USA 83:3012). Since bFGF lacks a signal sequence typical for released proteins, and since bFGF levels present in the brain are much larger than those of βNGF and BDNF, it has been questioned whether bFGF plays a physiological role as neurotrophic factor and has been proposed that bFGF acts as "injury factor" released in events involving cellular destruction. (Thoenen, et al., 1987, Rev. Physiol. Biochem. Pharmacol. 109:145).

Another neurotrophic factor having potential therapeutic use for peripheral nervous system disorders, ciliary neurotrophic factor (CNTF), has been cloned and expressed. (Lin, et al., 1989, Science, 246:1023). CNTF, which was purified from adult rabbit sciatic nerves, acts on the peripheral nervous system and appears to be completely unrelated to NGF.

It is an object to identify a fourth neurotrophic factor in the NGF family and to obtain nucleic acid encoding such a factor.

It is another object to synthesize such a new factor in recombinant cell culture.

It is yet another object to provide variants and modified forms of such a new factor.

It is an additional object to prepare immunogens for raising antibodies, as well as to obtain antibodies, capable of binding such a new factor or variant or modified form thereof.

Another object is to provide diagnostic and therapeutic compositions comprising such a new factor or variant or modified forms thereof, and methods of therapeutic treatment.

SUMMARY OF THE INVENTION

These and other objects of the invention apparent to the ordinary artisan are accomplished by first providing a nucleic acid sequence comprising at least a portion of the coding sequence for a new nerve-derived factor related to NGF, BDNF, and NT-3, hereafter termed neurotrophic factor-4 (NT-4).

In one aspect, the invention provides an isolated nucleic acid encoding NT-4. In another aspect, the invention provides a vector comprising this nucleic acid. In a third aspect, the invention supplies a recombinant host cell comprising this nucleic acid. In yet another aspect, the invention furnishes a composition comprising NT-4 from an animal species, which composition is free of contaminating polypeptides of that animal species.

The nucleic acid encoding NT-4 is also used in hybridization assays to identify and to isolate nucleic acids having substantial sequence homology to the nucleic acid encoding NT-4.

NT-4 or fragments thereof (which also may be synthesized by in vitro methods) are fused (by recombinant expression or in vitro covalent methods) to an immunogenic polypeptide and this, in turn, is used to immunize an animal in order to raise antibodies against an NT-4 epitope. Anti-NT-4 is recovered from the serum of immunized animals. Alternatively, monoclonal antibodies are prepared from cells of the immunized animal in conventional fashion. Antibodies identified by routine screening will bind to NT-4 but will not substantially cross-react with NGF, BDNF, or NT-3. Immobilized anti-NT-4 antibodies are useful particularly in the diagnosis (in vitro or in vivo) or purification of NT-4.

Substitutional, deletional, or insertional mutants of NT-4 are prepared in vitro or recombinant methods and screened for immuno-crossreactivity with NT-4 and for NT-4 antagonist or agonist activity.

NT-4 also is derivatized in vitro in order to prepare immobilized NT-4 and labelled NT-4, particularly for purposes of diagnosis of NT-4 or its antibodies, or for affinity purification of NT-4 antibodies.

NT-4, or a variant or modified form thereof, or anti-NT-4 antibody is formulated into physiologically acceptable vehicles, especially for therapeutic use. Such vehicles include sustained-release formulations.

In another aspect, the invention provides a method for producing NT-4, or a variant or modified form thereof, comprising culturing a transformed host cell and recovering the desired polypeptide from the host cell culture.

NT-4 has been found to have a broad tissue distribution and is structurally related to NGF, BDNF, and NT-3. Its presence in the brain and muscle tissue indicates that it may be useful as a therapeutic agent for neurodegenerative diseases and damaged nerve cells, e.g., nerves damaged as a result of trauma.

Therefore, in another aspect, the invention provides a method for treating a neurodegenerative disease or damaged nerve cells comprising administering to a mammal an effective amount of NT-4, or a variant or modified form thereof.

BRIEF DESCRIPTION OF THE DRAWINGS

FIG. 1 shows the partial nucleotide sequence for the human NT-4 gene (SEQ ID NO. 1) and the deduced amino acid sequence (SEQ ID NO. 2), including the entire nucleotide and amino acid sequences for mature human NT-4. The arrow indicates where the mature sequence begins, the asterisk indicates where the sequence begins for calculating homology with other members of the neurotrophic factor family, and the stop codon is circled. The amino acids are numbered from the N-terminus of the mature region.

FIG. 2 shows the homologies among the amino acid sequences of human NT-2 (SEQ ID NO. 3), NT-3 (SEQ ID NO. 4), and NGF (SEQ ID NO. 5), and the mature and partial precursor portion of NT-4 (SEQ ID NO. 6). The locations of the sense (NGX-54) and antisense (AR1) primer sites on the sequence are marked with vertical solid arrows, and the start of the mature region is indicated with an arrow.

FIG. 3 shows the nucleotide sequence of a cDNA encoding a portion of human NT-4β (SEQ ID NO. 7), and the deduced amino acid sequence of this portion of NT-4β (SEQ ID NO. 8).

FIG. 4 shows the nucleotide sequence of a genomic DNA encoding human NT-4γ (SEQ ID NO. 9), and the deduced amino acid sequence (SEQ ID NO. 10). The first in-frame Met residue is located at nucleotide positions 356–358, and is the putative start codon of human NT-4γ.

FIG. 5 shows the nucleotide sequence of a genomic DNA encoding human NT-4Δ (SEQ ID NO. 11), and the deduced amino acid sequence of this portion of NT-4Δ (SEQ ID NO. 12).

FIG. 6 shows the homologies among the amino acid sequences of human NT-4, NT-4β, NT-4γ, and NT-4Δ. The arrow indicates where the sequence of mature human NT-4 begins.

DETAILED DESCRIPTION OF THE PREFERRED EMBODIMENTS

As used herein, "NT-4" refers to a polypeptide having the amino acid sequence shown in FIG. 1 for mature human NT-4, amino acid sequence variants of such polypeptide, peptide fragments of mature human NT-4 and said amino acid sequence variants, which peptides are at least about 5 amino acids in length and comprise an immune epitope or other biologically active site of the corresponding polypeptide, and modified forms of mature human NT-4 and said amino acid sequence variants and peptide fragments wherein the polypeptide or peptide has been covalently modified by substitution with a moiety other than a naturally occurring amino acid; provided, however, that the particular amino acid sequence variant, peptide fragment, or modified form thereof under consideration is novel and unobvious over the prior art, and is not NGF, BDNF, or NT-3 of any animal species or any fragment or modified form of such NGF, BDNF, or NT-3.

NT-4 nucleic acid is RNA or DNA which encodes a NT-4 polypeptide or which hybridizes to such DNA and remains stably bound to it under stringent conditions and is greater than about 10 bases in length; provided, however, that such hybridizing nucleic acid is novel and unobvious over any prior art nucleic acid including that which encodes or is complementary to nucleic acid encoding NGF, BDNF, or NT-3. Stringent conditions are those which (1) employ low ionic strength and high temperature for washing, for example, 0.15 M NaCl/0.015 M sodium citrate/0.1% NaDodSO$_4$ at 50° C., or (2) use during hybridization a denaturing agent such as formamide, for example, 50% (vol/vol) formamide with 0.1% bovine serum albumin/0.1% Ficoll/0.1% polyvinylpyrrolidone/50 mM sodium phosphate buffer at pH 6.5 with 750 mM NaCl, 75 mM sodium citrate at 42° C.

DNA encoding NT-4 is obtained from brain tissue cDNA libraries, or genomic DNA, or by in vitro synthesis. Hybridizing nucleic acid generally is obtained by in vitro synthesis. identification of NT-4 DNA most conveniently is accomplished by probing human cDNA or genomic libraries by labeled oligonucleotide sequences selected from the FIG. 1 sequence in accord with known criteria, among which is that the sequence should be of sufficient length and sufficiently unambiguous that false positives are minimized. Typically, a $^{32}$P-labeled oligonucleotide having about 30 to 50 bases is sufficient, particularly if the oligonucleotide contains one or more codons for methionine or tryptophan. Isolated nucleic acid will be DNA that is identified and separated from contaminant nucleic acid encoding other polypeptides from the source of nucleic acid. The nucleic acid may be labeled for diagnostic purposes.

Amino acid sequence variants of NT-4 are polypeptides having an amino acid sequence which differs from that shown in FIG. 1 for mature human NT-4 by virtue of the insertion, deletion, and/or substitution of one or more amino acid residues within the FIG. 1 sequence. Amino acid sequence variants generally will be at least about 75% homologous (and often greater than 85% homologous) to mature human NT-4 based on a comparison of the amino acids present at each position within the sequences, after aligning the sequences to provide for maximum homology.

Amino acid sequence variants of NT-4 may be naturally occurring or may be prepared synthetically, such as by introducing appropriate nucleotide changes into a previously isolated NT-4 DNA, or by in vitro synthesis of the desired variant polypeptide. As indicated above, such variants will comprise deletions from, or insertions or substitutions of, one or more amino acid residues within the amino acid sequence shown for mature human NT-4 in FIG. 1. Any combination of deletion, insertion, and substitution is made to arrive at an amino acid sequence variant of NT-4, provided that the resulting variant polypeptide possesses a desired characteristic. The amino acid changes also may result in further modifications of NT-4 upon expression in recombinant hosts, e.g. introducing or moving sites of glycosylation, or introducing membrane anchor sequences (in accordance with PCT WO 89/01041 published Feb. 9, 1989).

Preferably, an amino acid sequence variant of NT-4 that is naturally occurring, including, for example, a naturally occurring allele, will be produced by recombinant means by expressing in a suitable host cell genomic DNA or cDNA comprising the nucleotide coding sequence for such naturally occurring variant. Other amino acid sequence variants of NT-4 will be produced by making predetermined mutations in a previously isolated NT-4 DNA. There are two principal variables to consider in making such predetermined mutations: the location of the mutation site and the nature of the mutation. In general, the location and nature of the mutation chosen will depend upon the NT-4 characteristic to be modified. For example, candidate NT-4 antagonists or super agonists initially will be selected by locating amino acid residues that are identical or highly conserved among NGF, BDNF, NT-3, and NT-4. Those residues then will be modified in series, e.g., by (1) substituting first with conservative choices and then with more radical selections depending upon the results achieved, (2) deleting the target, residue, or (3) inserting residues of the same or different class adjacent to the located site, or combinations of options 1–3.

One helpful technique is called "ala scanning". Here, an amino acid residue or group of target residues are identified and substituted by alanine or polyalanine. Those domains demonstrating functional sensitivity to the alanine substitutions then are refined by introducing further or other variants at or for the sites of alanine substitution.

Obviously, such variations which, for example, convert NT-4 into NGF, BDNF, or NT-3 are not included within the scope of this invention, nor are any other NT-4 variants or polypeptide sequences that are not novel and unobvious over the prior art. Thus, while the site for introducing an amino acid sequence variation is predetermined, the nature of the mutation per se need not be predetermined. For example, to optimize the performance of a mutation at a given site, ala scanning or random mutagenesis is conducted at the target codon or region and the expressed NT-4 variants are screened for the optimal combination of desired activity.

Amino acid sequence deletions generally range from about 1 to 30 residues, more preferably about 1 to 10 residues, and typically are contiguous. Deletions may be introduced into regions of low homology among BDNF, NGF, NT-3, and NT-4 to modify the activity of NT-4. Deletions from NT-4 in areas of substantial homology with BDNF, NT-3, and NGF will be more likely to modify the biological activity of NT-4 more significantly. The number of consecutive deletions will be selected so as to preserve the tertiary structure of NT-4 in the affected domain, e.g., beta-pleated sheet or alpha helix.

Amino acid sequence insertions include amino- and/or carboxyl-terminal fusions ranging in length from one residue to polypeptides containing a thousand or more residues, as well as intrasequence insertions of single or multiple amino acid residues. Intrasequence insertions (i.e., insertions within the mature NT-4 sequence) may range generally from about 1 to 10 residues, more preferably 1 to 5, most preferably 1 to 3. An example of a terminal insertion includes fusion of a heterologous N-terminal signal sequence to the N-terminus of the NT-4 molecule to facilitate the secretion of mature NT-4 from recombinant hosts. Such signals generally will be homologous to the intended host cell and include STII or Ipp for E. coli, alpha factor for yeast, and viral signals such as herpes gD for mammalian cells. Other insertions include the fusion of an immunogenic polypeptide such as a bacterial or yeast protein to the N- or C-termini of NT-4.

The third group of variants are those in which at least one amino acid residue in NT-4, and preferably only one, has been removed and a different residue inserted in its place. An example is the replacement of arginine and lysine by other amino acids to render the NT-4 resistent to proteolysis by serine proteases, thereby creating a variant of NT-4 that is more stable. The sites of greatest interest for substitutional mutagenesis include sites where the amino acids found in BDNF, NGF, NT-3, and NT-4 are substantially different in terms of side chain bulk, charge of hydrophobicity, but where there also is a high degree of homology at the selected site within various animal analogues of NGF, NT-3, and BDNF (e.g., among all the animal NGFs, all the animal NT-3s, and all the BDNFs). This analysis will highlight residues that may be involved in the differentiation of activity of the trophic factors, and therefore, variants at these sites may affect such activities. Examples of such sites in mature human NT-4, numbered from the N-terminal end, and exemplary substitutions include NT-4 (G78→K, H, Q or R) (SEQ ID NOS. 13, 14, 15, and 16, respectively) and NT-4 (R85→E, F, P, Y or W) (SEQ ID NOS. 17, 18, 19, 20, and 21, respectively). Other sites of interest are those in which the residues are identical among all animal species' BDNF, NGF, NT-3, and NT-4, this degree of conformation suggesting importance in achieving biological activity common to all four factors. These sites, especially those falling within a sequence of at least 3 other identically conserved sites, are substituted in a relatively conservative manner. Such conservative substitutions are shown in Table 1 under the heading of preferred substitutions. If such substitutions result in a change in biological activity, then more substantial changes, denominated exemplary substitutions in Table 1, or as further described below in reference to amino acid classes, are introduced and the products screened.

TABLE 1

| Original Residue | Exemplary Substitutions | Preferred Substitutions |
| --- | --- | --- |
| Ala (A) | val; leu; ile | val |
| Arg (R) | lys; gln; asn | lys |
| Asn (N) | gln; his; lys; arg | gln |
| Asp (D) | glu | glu |
| Cys (C) | ser | ser |
| Gln (Q) | asn | asn |
| Glu (E) | asp | asp |
| Gly (G) | pro | pro |
| His (H) | asn; gln; lys; arg; | arg |
| Ile (I) | leu; val; met; ala; phe; norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala | leu |
| Pro (P) | gly | gly |
| Ser (S) | thr | thr |
| Thr (T) | ser | ser |
| Trp (W) | tyr | tyr |
| Tyr (Y) | trp; phe; thr; ser | phe |
| Val (V) | ile; leu; met; phe; ala; norleucine | leu |

Sites particularly suited for conservative substitutions include, numbered from the N-terminus of the mature human NT-4, R11, G12, E13, V16, D18, W23, V24, D26, V40, L41, Q54, Y55, F56, E58, T59, G77, R79, G80, H85, W86, A99, L100, T101, W110, R111, W112, I113, R114, I115, D116, and A118. Cysteine residues not involved in maintaining the proper conformation of NT-4 also may be substituted, generally with serine, in order to improve the oxidative stability of the molecule and prevent aberrant crosslinking. Sites other than those set forth in this paragraph are suitable for deletional or insertional studies generally described above.

Substantial modifications in function or immunological identity are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side chain properties:

(1) hydrophobic: norleucine, met, ala, val, leu, ile;

(2) neutral hydrophilic: cys, ser, thr;

(3) acidic: asp, glu;

(4) basic: asn, gln, his, lys, arg;

(5) residues that influence chain orientation: gly, pro; and (6) aromatic: trp, tyr, phe.

Non-conservative substitutions will entail exchanging a member of one of these classes for another. Such substituted residues also may be introduced into the conservative substitution sites set forth above or, more preferably, into the remaining (non-conserved) sites.

Examples of NT-4 variants include NT-4(E67→S or T) (SEQ ID NOS. 22 and 23, respectively) (this adds an N-linked glycosylation site); NT-4(R83-Q94) (SEQ ID NO. 24); NT-4(G1-C61) (SEQ ID NO. 25) (variants so depicted are fragments containing the residues indicated); NT-4(G1-C17) (SEQ ID NO. 26); NT-4(C17-C61) (SEQ ID NO. 27); NT-4(C17-C78) (SEQ ID NO. 28); NT-4(C17-C90) (SEQ ID NO. 29); NT-4(C17-C119) (SEQ ID NO. 30); NT-4(C17-C121) (SEQ ID NO. 31); NT-4(R11-R27) (SEQ ID NO. 32); NT-4(R11-R34) (SEQ ID NO. 33); NT-4(R34-R53) (SEQ ID NO. 34); NT-4(C61-C78) (SEQ ID NO. 35); NT-4(R53-C61) (SEQ ID NO. 36); NT-4(C61-C119) (SEQ ID NO. 37); NT-4(C61-C78) (SEQ ID NO. 38); NT-4(C78-C119) (SEQ ID NO. 39); NT-4(C61-C90) (SEQ ID NO. 40); NT-4(R60-C78) (SEQ ID NO. 41); NT-4(K62-C119) (SEQ ID NO. 42); NT-4(K62-K91) (SEQ ID NO. 43); NT-4(R79-R98) (SEQ ID NO. 44); NT-4(R83-K93) (SEQ ID NO. 45); NT-4 (T101–R111) (SEQ ID NO. 46); NT-4(G1-C121) VLTVKRVRR (SEQ ID NO. 47); NT-4(V40-C121) VLTVKRVRR (SEQ ID NO. 48); NT-4(V40-C121) SLTIKRIRA (SEQ ID NO. 49); NT-4(V40-C121) TLSRK-AGR RA (SEQ ID NO. 50); DDDSPIARRGEISVCDSVS-DWVSAPDKDTAVD IKGDDVMVLKKVGINHSV NT-4 (V40-C121) (SEQ ID NO. 51); hNGF(S1-V48) NT-4(V40-C121) hNGF(V109-A120) (SEQ ID NO. 52); NT-4(ΔC78) (SEQ ID NO. 53); NT-4(ΔC61) (SEQ ID NO. 54); NT-4 (ΔQ54-ΔT59) (SEQ ID NO. 55) (variants depicted in this fashion comprise deletions of the indicated span of residues, inclusive); NT-4(ΔR60-ΔD82) (SEQ ID NO. 56); NT-4 (ΔH85-ΔS88) (SEQ ID NO. 57); NT-4(ΔW86-ΔT101) (SEQ ID NO. 58); NT-4(R53→H) (SEQ ID NO. 59); NT-4 (K91→H) (SEQ ID NO. 60); NT-4(V108→F) (SEQ ID NO. 61); NT-4(R84→Q, H, N, T, Y or W) (SEQ ID NOS. 62, 63, 64, 65, 66, and 67, respectively); and NT-4(D116→E, N, Q, Y, S or T) (SEQ ID NOS. 68, 69, 70, 71, 72, and 73, respectively.

Also included in NT-4 wherein position 70 is substituted with an amino acid residue other than G, E, D or P; position 71 with other than A, P or M; and/or position 83 with other than R, D, S or K; as well as cyclized NT-4 fragments, including cyclic polypeptides comprising the sequences IKTG (SEQ ID NO. 74), EIKTG (SEQ ID NO. 75), EIK-TGN (SEQ ID NO. 76), SPV, SPVK (SEQ ID NO. 77), HQV, KSS, KSSA (SEQ ID NO. 78), YAEHKS (SEQ ID NO. 79), RYAEHKS (SEQ ID NO. 80), RYAEHKSH (SEQ ID NO. 81), YAEHKSH (SEQ ID NO. 82), ANRTS (SEQ ID NO. 83), NRT, ANRT (SEQ ID NO. 84), NRTS (SEQ ID NO. 85), KEA, KEAR (SEQ ID NO. 86), KEARP (SEQ ID NO. 87), IDDK (SEQ ID NO. 88) SENN (SEQ ID NO. 89), TSENN (SEQ ID NO. 90), TSENNK (SEQ ID NO. 91) or KLVG (SEQ ID NO. 92).

Also within the scope hereof are BDNF, NT-3, and NGF amino acid sequence variants having analogous structures to the NT-4 variants set forth herein. For example, the analogous positions of NGF, NT-3, and BDNF are substituted with a residue other than D, E, or P, respectively, in analogy to the same mutation at position 70 of NT-4.

DNA encoding amino acid sequence variants of NT-4 may be isolated from a natural source (in the case of naturally occurring amino acid sequence variants) or may be prepared by site-specific mutagenesis of DNA that encodes an earlier prepared variant or a nonvariant version of NT-4. Site-specific mutagenesis allows the production of NT-4 variants through the use of specific oligonucleotide sequences that encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 20 to 25 nucleotides in length is preferred, with about 5 to 10 residues on both sides of the junction of the sequence being altered. In general, the technique of site-specific mutagenesis is well known in the art, as exemplified by publications such as Adelman, et al., 1983, DNA 2:183.

As will be appreciated, the site-specific mutagenesis technique typically employs a phage vector that exists in both a single-stranded and double-stranded form. Typical vectors useful in site-directed mutagenesis include vectors such as the M13 phage, for example, as disclosed by Messing, et al., 1981, *Third Cleveland Symposium on Macromolecules and Recombinant DNA*, (A. Walton, Ed., Elsevier, Amsterdam). These phage are readily commercially available and their use is generally well known to those skilled in the art. Also, plasmid vectors that contain a single-stranded phage origin of replication (Veira, et al., 1987, Meth. Enzymol. 153:3) may be employed to obtain single-stranded DNA. Alternatively, nucleotide substitutions are introduced by synthesizing the appropriate DNA fragment in vitro and amplifying it by polymerase chain reaction (PCR) procedures known per se in the art.

In general, site-directed mutagenesis in accordance herewith is performed by first obtaining a single-stranded vector that includes within its sequence a DNA sequence that encodes the relevant protein. An oligonucleotide primer bearing the desired mutated sequence is prepared, generally synthetically, for example, by the method of Crea, et al., 1978, Proc. Natl. Acad. Sci. 75:5765). This primer is then annealed with the single-stranded protein-sequence-containing vector, and subjected to DNA-polymerizing enzymes such as *E. coli* polymerase I Klenow fragment, to complete the synthesis of the mutation-bearing strand. Thus, a heteroduplex is formed wherein one strand encodes the original non-mutated sequence and the second strand bears the desired mutation. This heteroduplex vector is then used to transform appropriate cells such as JM101 cells and clones are selected that include recombinant vectors bearing the mutated sequence arrangement.

After such a clone is selected, the mutated region may be removed and placed in an appropriate vector for protein production, generally an expression vector of the type that is typically employed for transformation of an appropriate host.

Most deletions and insertions, and substitutions in particular, of amino acids in NT-4 are not expected to produce radical changes in its characteristics, and single substitutions will preserve at least one immune epitope in the NT-4 polypeptide.

Since it is often difficult to predict in advance the characteristics of a variant NT-4, it will be appreciated that some screening will be needed to identify a variant having a desired characteristic. One can screen for enhanced trophic activity, differential neuron cell type specificity, stability in recombinant cell culture or in plasma (e.g. against proteolytic cleavage), possession of antagonist activity, oxidative stability, ability to be secreted in elevated yields, and the like. For example, a change in the immunological character of the NT-4 polypeptide, such as affinity for a given antibody, is measured by a competitive-type immunoassay. Changes in the enhancement or suppression of neurotrophic activities by the candidate mutants are measured by dendrite outgrowth or explant cell survival assays. Modifications of such protein properties as redox or thermal stability, hydrophobicity, susceptibility to proteolytic degradation, or the tendency to aggregate with carriers or into multimers are assayed by methods well known in the art.

Trypsin or other protease cleavage sites are identified by inspection of the encoded amino acid sequence for paired basic amino acid residues, e.g. combinations of adjacent arginyl and lysinyl residues. These are rendered inactive to protease by substituting one of the residues with another residue, preferably a basic residue such as glutamine or a hydrophobic residue such as serine; by deleting one or both of the basic residues; by inserting a prolyl residue immediately after the last basic residue; or by inserting another residue between the two basic residues.

An amino acid sequence variant of NT-4 typically is produced by recombinant means, that is, by expression of nucleic acid encoding the variant NT-4 in recombinant cell culture, and, optionally, purification of the variant polypeptide from the cell culture, for example, by bioassay of the variant's activity or by adsorption on an immunoaffinity column comprising rabbit anti-NT-4 polyclonal antibodies (which will bind to at least one immune epitope of the variant which is also present in native NT-4). Small peptide fragments, on the order of 40 residues or less, are conveniently made by in vitro methods.

Once DNA encoding NT-4 is obtained, typically it is then ligated into a replicable vector for further cloning or for expression. Vectors are useful for performing two functions in collaboration with compatible host cells (a host-vector system). One function is to facilitate the cloning of the DNA that encodes the NT-4, i.e., to produce usable quantities of the nucleic acid. The other function is to direct the expression of NT-4. One or both of these functions are performed by the vector-host system. The vectors will contain different components depending upon the function they are to perform as well as the host cell that is selected for cloning or expression.

Each vector will contain DNA that encodes NT-4 as described above. Typically, this will be DNA that encodes the NT-4 in its mature form linked at its amino terminus to a secretion signal. This secretion signal preferably is the NT-4 presequence that normally directs the secretion of NT-4 from human cells in vivo. However, suitable secretion signals also include signals from other animal NT-4, signals from NGF, NT-2, or NT-3, viral signals, or signals from secreted polypeptides of the same or related species.

Figure 2:
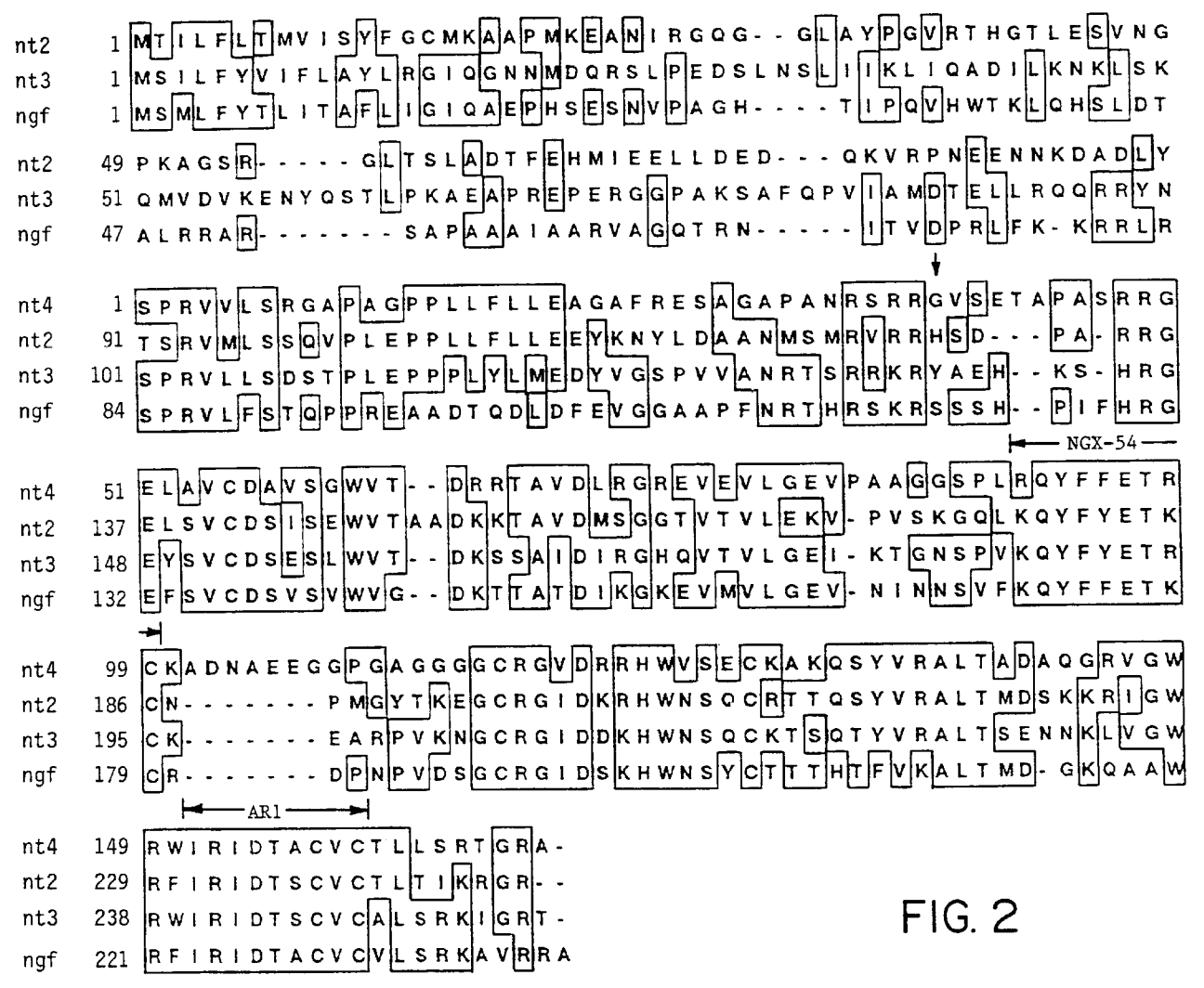

If the signal sequence is from another neurotrophic polypeptide, it may be the precursor sequence shown in FIG. 2 which extends from the initiating methionine (M) residue of NT-2, NT-3, or NGF up to the arginine (R) residue just before the first amino acid of the mature protein, or a consensus or combination sequence from any two or more of those precursors taking into account homologous regions of the precursors. The DNA for such precursor region is ligated in reading frame to DNA encoding the mature NT-4.

Expression and cloning vectors contain a nucleotide sequence that enables the vector to replicate in one or more selected host cells. Generally, in cloning vectors this sequence is one that enables the vector to replicate independently of the host chromosomes, and includes origins of replication or autonomously replicating sequences. Such sequences are well-known for a variety of bacteria, yeast and viruses. The origin of replication from the well-known plasmid pBR322 is suitable for most gram negative bacteria, the $2\mu$ plasmid origin for yeast and various vital origins (SV40, polyoma, adenovirus, VSV or BPV) are useful for cloning vectors in mammalian cells. Origins are not needed for mammalian expression vectors (the SV40 origin may typically be used only because it contains the early promoter). Most expression vectors are "shuttle" vectors, i.e. they are capable of replication in at least one class of organisms but can be transfected into another organism for expression. For example, a vector is cloned in *E. coli* and then the same vector is transfected into yeast or mammalian cells for expression even though it is not capable of replicating independently of the host cell chromosome.

DNA also is cloned by insertion into the host genome. This is readily accomplished with bacillus species, for example, by including in the vector a DNA sequence that is complementary to a sequence found in bacillus genomic DNA. Transfection of bacillus with this vector results in homologous recombination with the genome and insertion of NT-4 DNA. However, the recovery of genomic DNA encoding NT-4 is more complex than that of an exogenously replicated vector because restriction enzyme digestion is required to excise the NT-4 DNA.

Expression and cloning vectors should contain a selection gene, also termed a selectable marker. Typically, this is a gene that encodes a protein necessary for the survival or growth of a host cell transformed with the vector. The presence of this gene ensures that any host cell which deletes the vector will not obtain an advantage in growth or reproduction over transformed hosts. Typical selection genes encode proteins that (a) confer resistance to antibiotics or other toxins, e.g. ampicillin, neomycin, methotrexate or tetracycline, (b) complement auxotrophic deficiencies, or (c) supply critical nutrients not available from complex media, e.g. the gene encoding D-alanine racemase for bacilli.

A suitable selection gene for use in yeast is the trp 1 gene present in the yeast plasmid YRp7 (Stinchcomb, et al., 1979, Nature 282:39; Kingsman, et al., 1979, Gene 7:141; Tschemper, et al., 1980, Gene 10:157). The trp 1 gene provides a selection marker for a mutant strain of yeast lacking the ability to grow in tryptophan, for example, ATCC No. 44076 or PEP4-1 (Jones, 1977, Genetics 85:12). The presence of the trp1 lesion in the yeast host cell genome then provides an effective environment for detecting transformation by growth in the absence of tryptophan. Similarly, Leu2 deficient yeast strains (ATCC 20,622 or 38,626) are complemented by known plasmids bearing the Leu2 gene.

Examples of suitable selectable markers for mammalian cells are dihydrofolate reductase (DHFR) or thymidine kinase. Such markers enable the identification of cells which were competent to take up the NT-4 nucleic acid. The mammalian cell transformants are placed under selection pressure which only the transformants are uniquely adapted to survive by virtue of having taken up the marker. Selection pressure is imposed by culturing the transformants under conditions in which the concentration of selection agent in the medium is successively changed, thereby leading to amplification of both the selection gene and the DNA that encodes NT-4. Amplification is the process by which genes in greater demand for the production of a protein critical for growth are reiterated in tandem within the chromosomes of successive generations of recombinant cells. Increased quantities of NT-4 are synthesized from the amplified DNA.

For example, cells transformed with the DHFR selection gene are first identified by culturing all of the transformants in a culture medium which contains methotrexate (Mtx), a competitive antagonist of DHFR. An appropriate host cell in this case is the Chinese hamster ovary (CHO) cell line deficient in DHFR activity, prepared and propagated as described by Urlaub and Chasin, 1980, Proc. Nat. Acad. Sci. 77:4216. A particularly useful DHFR is a mutant DHFR that is highly resistant to Mtx (EP 117,060A). The transformed cells then are exposed to increased levels of Mtx. This leads to the synthesis of multiple copies of the DHFR gene and, concomitantly, multiple copies of other DNA comprising the expression vectors, such as the DNA encoding NT-4. Alternatively, host cells transformed by an expression vector comprising DNA sequences encoding NT-4, DHFR protein, and aminoglycoside 3' phosphotransferase (APH) can be selected by cell growth in medium containing an aminoglycosidic antibiotic such as kanamycin or neomycin or G418. Because eukaryotic cells do not normally express an endogenous APH activity, genes encoding APH protein, commonly referred to as neo' genes, may be used as dominant selectable markers in a wide range of eukaryotic host cells, by which cells transformed by the vector can readily be identified.

Other methods, vectors and host cells suitable for adaptation to the synthesis of NT-4 in recombinant vertebrate cell culture are described in Gething, et al., 1981, Nature 293:620; Mantei, et al., 1979, Nature 281:40; and Levinson, et al., EP 117,060A and 117,058A. A particularly useful plasmid for mammalian cell culture expression of NT-4 is pRK5 (EP Pub. No. 307,247) or pSVI6B (PCT Pub. No. WO90/08291, published Jun. 13, 1991).

Expression vectors, unlike cloning vectors, should contain a promoter which is recognized by the host organism and is operably linked to the NT-4 nucleic acid. Promoters are untranslated sequences located upstream from the start codon of a structural gene (generally within about 100 to 1000 bp) that control the transcription and translation of nucleic acid under their control. They typically fall into two classes, inducible and constitutive. Inducible promoters are promoters that initiate increased levels of transcription from DNA under their control in response to some change in culture conditions, e.g. the presence or absence of a nutrient or a change in temperature. At this time a large number of promoters recognized by a variety of potential host cells are well known. These promoters are operably linked to NT-4-encoding DNA by removing them from their gene of origin by restriction enzyme digestion, followed by insertion 5' to the start codon for NT-4. This is not to say that the genomic NT-4 promoter is not usable. However, heterologous promoters generally will result in greater transcription and higher yields of expressed NT-4.

Nucleic acid is operably linked when it is placed into a functional relationship with another nucleic acid sequence. For example, DNA for a presequence or secretory leader is operably linked to DNA for a polypeptide if it is expressed as a preprotein which participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, operably linked means that the DNA sequences being linked are contiguous and, in the case of a secretory leader, contiguous and in reading phase. Linking is accomplished by ligation at convenient restriction sites. If such sites do not exist then synthetic oligonucleotide adaptors or linkers are used in accord with conventional practice.

Promoters suitable for use with prokaryotic hosts include the β-lactamase and lactose promoter systems (Chang, et al., 1978, Nature 275:615; Goeddel, et al., 1979, Nature 281:544), alkaline phosphatase, a tryptophan (trp) promoter system (Goeddel, 1980, Nucleic Acids Res. 8:4057 and EPO Appln. Publ. No. 36,776) and hybrid promoters such as the tac promoter (H. de Boer, et al., 1983, Proc. Nat'l. Acad. Sci. 80:21). However, other known bacterial promoters are suitable. Their nucleotide sequences have been published, thereby enabling a skilled worker operably to ligate them to DNA encoding NT-4 (Siebenlist, et al., 1980, Cell 20:269) using linkers or adaptors to supply any required restriction sites. Promoters for use in bacterial systems also will contain a Shine-Dalgarno (S.D.) sequence operably linked to the DNA encoding NT-4.

Suitable promoting sequences for use with yeast hosts include the promoters for 3-phosphoglycerate kinase (Hitzeman, et al., 1980, J. Biol. Chem. 255:2073) or other glycolytic enzymes (Hess, et al., 1968, J. Adv. Enzyme Reg. 7:149; Holland, 1978, Biochemistry 17:4900), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in R. Hitzeman, eta l., EP 73,657A. Yeast enhancers also are advantageously used with yeast promoters.

Transcription of NT-4-encoding DNA in mammalian host cells is controlled by promoters obtained from the genomes of viruses such as polyoma, cytomegalovirus, adenovirus, retroviruses, hepatitis-B virus and most preferably Simian Virus 40 (SV40), or from heterologous mammalian promoters, e.g. the actin promoter. The early and late promoters of the SV40 virus are conveniently obtained as an SV40 restriction fragment which also contains the SV40 viral origin of replication (Fiers, eta l., 1978, Nature 273:113). Of course, promoters from the host cell or related species also are useful herein.

Transcription of NT-4-encoding DNA in mammalian host cells may be increased by inserting an enhancer sequence into the vector. An enhancer is a nucleotide sequence, usually about from 10–300 bp, that acts on a promoter to increase its transcription and does so in a manner that is relatively orientation and position independent. Many enhancer sequences are now known from mammalian genes (globin, elastase, albumin, α-fetoprotein and insulin). Typically, however, one will use an enhancer from a eukaryotic cell virus. Examples include the SV40 enhancer on the late side of the replication origin (bp 100–270), the cytomegalovirus early promoter enhancer, the polyoma enhancer on the late side of the replication origin, and adenoviral enhancers. The enhancer may be spliced into the vector at a position 5' or 3' to the NT-4-encoding sequence, but is preferably located at a site 5' from the promoter.

Expression vectors used in eukaryotic host cells (yeast, fungi, insect, plant, animal, human or nucleated cells from other multicellular organisms) will also contain sequences necessary for the termination of transcription and for stabilizing the mRNA. Such sequences are commonly available from the 5' and, occasionally 3' untranslated regions of eukaryotic or viral DNAs or cDNAs. These regions contain regions that are transcribed as polyadenylated segments in the untranslated portion of the mRNA encoding NT-4. The 3' untranslated regions also include the transcription termination sites.

Suitable host cells for cloning or expressing the vectors herein are the prokaryote, yeast or higher eukaryote cells described above. Suitable prokaryotes include gram negative or gram positive organisms, for example *E. coli* or bacilli. A preferred cloning host is *E. coli* 294 (ATCC 31,446) although other gram negative or gram positive prokaryotes such as *E. coli* B, *E. coli* X1776 (ATCC 31,537), *E. coli* W3110 (ATCC 27,325), pseudomonas species, or *Serratia marcesans* are suitable.

In addition to prokaryotes, eukaryotic microbes such as filamentous fungi or yeast are suitable hosts for NT-4-encoding vectors. *Saccharomvces cervisiae*, or common baker's yeast, is the most commonly used among lower eukaryotic host microorganisms. However, a number of other genera, species and strains are commonly available and useful herein.

Suitable host cells for the expression of NT-4 are derived from multicellular organisms. Such host cells are capable of complex processing and glycosylation activities. In principle, any higher eukaryotic cell culture is workable, whether from vertebrate or invertebrate culture, although cells from mammals such as humans are preferred. Propagation of such cells in culture is per se well known. (*Tissue Culture*, 1973, Kruse and Patterson, Eds., Academic Press, New York). Examples of useful mammalian host cell lines are VERO and HeLa cells, Chinese hamster ovary cell lines, the WI38, BHK, COS-7, MDCK cell lines and human embryonic kidney cell line 293.

Host cells are transformed with the above-described expression or cloning vectors and cultured in conventional nutrient media modified as is appropriate for inducing promoters or selecting transformants containing amplified genes. The culture conditions, such as temperature, pH and the like, suitably are those previously used with the host cell selected for cloning or expression, as the case may be, and will be apparent to the ordinary artisan.

NT-4 preferably is recovered from the culture medium as a secreted protein, although it also may be recovered from host cell lysates when directly expressed without a secretory signal. When NT-4 is expressed in a recombinant cell other than one of human origin, the NT-4 is thus completely free of proteins of human origin. However, it is necessary to purify NT-4 from recombinant cell proteins in order to obtain preparations that are substantially homogeneous as to protein. As a first step, the culture medium or lysate is centrifuged to remove particulate cell debris. NT-4 thereafter is purified from contaminant soluble proteins, for example, by fractionation on immunoaffinity or ion exchange columns; ethanol precipitation; reverse phase HPLC; chromatography on silica or on a cation exchange resin such as DEAE; chromatofocusing; SDS-PAGE; ammonium sulfate precipitation; or gel electrophoresis using, for example, Sephadex G-75. NT-4 variants in which residues have been deleted, inserted or substituted relative to native NT-4 are recovered in the same fashion as native NT-4, taking account of any substantial changes in properties occasioned by the variation. For example, preparation of an NT-4 fusion with another protein, e.g. a bacterial or viral antigen, facilitates purification because an immunoaffinity column containing antibody to the antigen can be used to adsorb the fusion protein. A protease inhibitor such as phenyl methyl sulfonyl fluoride (PMSF) may be useful to inhibit proteolytic degradation during purification, and antibiotics may be included to prevent the growth of adventitious contaminants. One skilled in the art will appreciate that purification methods suitable for native NT-4 may require modification to account for changes in the character of NT-4 or its variants upon expression in recombinant cell culture.

Peptide fragments of NT-4 and modified forms of NT-4 also are included within the scope of this invention. Peptide fragments having up to about 40 amino residues may be conveniently prepared by in vitro synthesis.

Covalent modifications are made by reacting targeted amino acid residues of an NT-4 polypeptide or peptide fragment with an organic derivatizing agent that is capable of reacting with selected side chains of the N- or C-terminal residues.

Cysteinyl residues most commonly are reacted with α-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, α-bromo-β-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylpyrocarbonate at pH 5.5–7.0 because this agent is relatively specific for the histidyl side chain. Para-bromophenacyl bromide also is useful; the reaction is preferably performed in 0.1M sodium cacodylate at pH 6.0.

Lysinyl and amino terminal residues are reacted with succinic or other carboxylic acid anhydrides. Derivatization with these agents has the effect of reversing the charge of the lysinyl residues. Other suitable reagents for derivatizing α-amino-containing residues include imidoesters such as methyl picolinimidate; pyridoxal phosphate; pyridoxal; chloroborohydride; trinitrobenzenesulfonic acid; O-methylisourea; 2,4-pentanedione; and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high $pK_a$ of the guanidine functional group. Furthermore, these reagents may react with the groups of lysine as well as the arginine epsilon-amino group.

The specific modification of tyrosyl residues may be made, with particular interest in introducing spectral labels into tyrosyl residues by reaction with aromatic diazonium compounds or tetranitromethane. Most commonly, N-acetylimidizole and tetranitromethane are used to form O-acetyl tyrosyl species and 3-nitro derivatives, respectively. Tyrosyl residues are iodinated using $^{126}I$ or $^{131}I$ to prepare labeled proteins for use in radioimmunoassay, the chloramine T method described above being suitable.

Carboxyl side groups (aspartyl or glutamyl) are selectively modified by reaction with carbodiimides (R'-N=C=N-R') such as 1-cyclohexyl-3-(2-morpholinyl-4-ethyl) carbodiimide or 1-ethyl-3-(4-azonia-4,4-dimethylpentyl) carbodiimide. Furthermore, aspartyl and glutamyl residues are converted to asparaginyl and glutaminyl residues by reaction with ammonium ions.

Derivatization with bifunctional agents is useful for crosslinking NT-4 to a water-insoluble support matrix or surface for use in the method for purifying anti-NT-4 antibodies, and vice versa. Commonly used crosslinking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), and bifunctional maleimides such as bis-N-maleimido-1,8-octane. Derivatizing agents such as methyl-3-[(p-azidophenyl)dithio] propioimidate yield photoactivatable intermediates that are capable of forming crosslinks in the presence of light. Alternatively, reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440 are employed for protein immobilization.

Glutaminyl and asparaginyl residues are frequently deamidated to the corresponding glutamyl and aspartyl residues. Alternatively, these residues are deamidated under mildly acidic conditions. Either form of these residues falls within the scope of this invention.

Other modifications include hydroxylation of proline and lysine, phosphorylation of hydroxyl groups of seryl or threonyl residues, methylation of the α-amino groups of lysine, arginine, and histidine side chains (Creighton, *Proteins: Structure and Molecular Properties*, W. H. Freeman & Co., San Francisco, pp. 79–86), acetylation of the N-terminal amine, and amidation of any C-terminal carboxyl group. NT-4 also is covalently linked to nonproteinaceous polymers, e.g. polyethylene glycol, polypropylene glycol or polyoxyalkylenes, in the manner set forth in U.S. patent application Ser. No. 07/275,296 or U.S. Pat. Nos. 4,640,835; 4,496,689; 4,301,144; 4,670,417; 4,791,192 to 4,179,337.

NT-4 in purified form, that is, in a form where the NT-4 is substantially free of other polypeptides or peptides, may be entrapped in microcapsules prepared, for example, by coacervation techniques or by interfacial polymerization (for example, hydroxymethylcellulose or gelatin-microcapsules and poly-(methylmethacylate) microcapsules, respectively), in colloidal drug delivery systems (for example, liposomes, albumin microspheres, microemulsions, nano-particles and nanocapsules) or in macroemulsions. Such techniques are disclosed in *Remington's Pharmaceutical Sciences*, 16th edition, 1980, (A. Osol, Ed).

NT-4 is believed to find use as an agent for enhancing the survival or inducing the outgrowth of nerve cells. It, therefore, is useful in the therapy of degenerative disorders of the nervous system ("neurodegenerative diseases"), including such diseases as Alzheimer's disease, Parkinson's disease, Huntington's chorea, ALS, peripheral neuropathies, and other conditions characterized by necrosis or loss of neurons, whether central, peripheral, or motorneurons. In addition, it may be useful for treating damaged nerve cells, e.g., nerves damaged by traumatic conditions such as burns and wounds, diabetes, kidney dysfunction, and the toxic effects of chemotherapeutics used to treat cancer and AIDS. It also is useful as a component of culture media for use in culturing nerve cells in vitro. Finally, NT-4 preparations are useful as standards in assays for NT-4 and in competitive-type receptor binding assays when labelled with radioiodine, enzymes, fluorophores, spin labels, and the like.

Therapeutic formulations of NT-4 are prepared or storage by mixing NT-4 having the desired degree of purity with optional physiologically acceptable carriers, excipients or stabilizers (*Remington's Pharmaceutical Sciences*, supra), in the form of lyophilized cake or aqueous solutions. Acceptable carriers, excipients or stabilizers are nontoxic to recipients at the dosages and concentrations employed, and include buffers such as phosphate, citrate and other organic acids; antioxidants including ascorbic acid; low molecular weight (less than about 10 residues) polypeptides; proteins, such as serum albumin, gelatin or immunoglobulins; hydrophilic polymers such as polyvinylpyrrolidone, amino acids such as glycine, glutamine, asparagine, arginine or lysine; monosaccharides, disaccharides and other carbohydrates including glucose, mannose, or dextrins; chelating agents such as EDTA; sugar alcohols such as mannitol or sorbitol; salt-forming counterions such as sodium; and/or nonionic surfactants such as Tween, Pluronics or PEG.

NT-4 to be used for in vivo administration must be sterile. This is readily accomplished by filtration through sterile filtration membranes, prior to or following lyophilization and reconstitution. NT-4 ordinarily will be stored in lyophilized form.

Therapeutic NT-4 compositions generally are placed into a container having a sterile access port, for example, an intravenous solution bag or vial having a stopper pierceable by a hypodermic injection needle.

NT-4 optionally is combined with or administered in concert with other neurotrophic factors including NGF, NT-3, and/or BDNF and is used with other conventional therapies for degenerative nervous disorders.

The route of NT-4 or NT-4 antibody administration is in accord with known methods, e.g. Injection or infusion by intravenous, intraperitoneal, intracerebral, intramuscular, intraocular, intraarterial and intralesional routes, topical administration, or by sustained release systems as noted below. NT-4 is administered continuously by infusion into the fluid reservoirs of the CNS, although bolus injection is acceptable. NT-4 preferably is administered into the ventricles of the brain or otherwise introduced into the CNS or spinal fluid. It should be administered by an indwelling catheter using a continuous administration means such as a pump, or it can be administered by implantation, e.g., intracerebral implantation, of a sustained-release vehicle. More specifically, NT-4 can be injected through chronically implanted cannulas or chronically infused with the help of osmotic minipumps. Subcutaneous pumps are available that deliver proteins through a small tubing to the cerebral ventricles. Highly sophisticated pumps can be refilled through the skin and their delivery rate can be set without surgical intervention. Examples of suitable administration protocols and delivery systems involving a subcutaneous pump device or continuous intracerebroventricular infusion through a totally implanted drug delivery system are those used for the administration of dopamine, dopamine agonists, and cholinergic agonists to Alzheimer patients and animal models for Parkinson's disease described by Harbaugh, 1987, J. Neural Transm. Suppl., 24:271; and DeYebenes, et al., 1987, Mov. Disord. 2:143. NT-4 antibody is administered in the same fashion, or by administration into the blood stream of lymph.

Suitable examples of sustained release preparations include semipermeable polymer matrices in the form of shaped articles, e.g. films, or microcapsules. Sustained release matrices include polyesters, hydrogels, polylactides (U.S. Pat. No. 3,773,919, EP 58,481), copolymers of L-glutamic acid and gamma ethyl-L-glutamate (Sidman, et al., 1983, Biopolymers 22:547), poly (2-hydroxyethyl-methacrylate) (Langer, et al., 1981, J. Biomed. Mater. Res. 15:167; Langer, 1982, Chem. Tech. 12:98), ethylene vinyl acetate (Langer, et al., ld.) or poly-D-(-)-3-hydroxybutyric acid (EP 133,988A). Sustained release NT-4 compositions also include liposomally entrapped NT-4. Liposomes containing NT-4 are prepared by methods known per se. (Epstein, et al., 1985, Proc. Natl. Acad. Sci. 82:3688; Hwang, et al., 1980, Proc. Natl. Acad. Sci. USA 77:4030; DE 3,218,121A; EP 52322A; EP 36676A; EP 88046A; EP 143949A; EP 142641A; Japanese Pat. App. No. 83-118008; U.S. Pat. Nos. 4,485,045 and 4,544,545; and EP 102,324A). Ordinarily the liposomes are of the small (about 200–800 Angstroms) unilamelar type in which the lipid content is greater than about 30 mol. % cholesterol, the selected proportion being adjusted for the optimal NT-4 therapy.

An effective amount of NT-4 to be employed therapeutically will depend, for example, upon the therapeutic objectives, the route of administration, and the condition of the patient. Accordingly, it will be necessary for the therapist to titer the dosage and modify the route of administration as required to obtain the optimal therapeutic effect. A typical daily dosage might range from about 1 $\mu$g/kg to up to 100 mg/kg or more, depending on the factors mentioned above. Typically, the clinician will administer NT-4 until a dosage is reached that repairs, maintains, and, optimally, reestablishes neuron function. The progress of this therapy is easily monitored by conventional assays.

Polyclonal antibodies to NT-4 generally are raised in animals by multiple subcutaneous (sc) or intraperitoneal (ip) injections of NT-4 and an adjuvant. It may be useful to conjugate NT-4 or a fragment containing the target amino acid sequence to a protein which is immunogenic in the species to be immunized, e.g., keyhole limpet hemocyanin, serum albumin, bovine thyroglobulin, or soybean trypsin inhibitor using a bifunctional or derivatizing agent, for example, maleimodobenzoyl sulfosuccinimide ester (conjugation through cysteine residues), N-hydroxysuccinimide (through lysine residues), glutaraldehyde, succinic anhydride, $SOCl_2$, or $R^1N=C=NR$.

Animals are immunized against the immunogenic conjugates or derivatives by combining 1 mg or 1 $\mu$g of conjugate (for rabbits or mice, respectively) with 3 volumes of Freund's complete adjuvant and injecting the solution intradermally at multiple sites. One month later the animals are boosted with ⅕ to ⅒ the original amount of conjugate i Freund's complete adjuvant by subcutaneous injection at multiple sites. 7 to 14 days later animals are bled and the serum is assayed for anti-NT-4 titer. Animals are boosted until the titer plateaus. Preferably, the animal is boosted with the conjugate of the same NT-4 polypeptide, but conjugated to a different protein and/or through a different cross-linking agent. Conjugates also can be made in recombinant cell culture as protein fusions. Also, aggregating agents such as alum are used to enhance the immune response.

Monoclonal antibodies are prepared by recovering spleen cells from immunized animals and immortalizing the cells in conventional fashion, e.g. by fusion with myeloma cells or by EB virus transformation and screening for clones expressing the desired antibody.

NT-4 antibodies are useful in diagnostic assays for NT-4 or its antibodies. The antibodies are labelled in the same fashion as NT-4 described above and/or are immobilized on an insoluble matrix. In one embodiment of a receptor binding assay, an antibody composition which binds to all or a selected plurality of members of the NT-4 family is immobilized on an insoluble matrix, the test sample is contacted with the immobilized antibody composition in order to adsorb all NT-4 family members, and then the immobilized family members are contacted with a plurality of antibodies specific for each member, each of the antibodies being individually identifiable as specific for a predetermined family member, as by unique labels such as discrete fluorophores or the like. By determining the presence and/or amount of each unique label, the relative proportion and amount of each family member can be determined.

NT-4 antibodies also are useful for the affinity purification of NT-4 from recombinant cell culture or natural sources. NT-4 antibodies that do not detectably cross-react with NGF, NT-3, or BDNF can be used to purify NT-4 free from these other family members.

Suitable diagnostic assays for NT-4 and its antibodies are well known per se. In addition to the bioassay described above, competitive, sandwich and steric inhibition immunoassay techniques are useful. The competitive and sandwich methods employ a phase separation step as an integral part of the method while steric inhibition assays are conducted in a single reaction mixture. Fundamentally, the same procedures are used for the assay of NT-4 and for substances that bind NT-4, although certain methods will be favored depending upon the molecular weight of the substance being assayed. Therefore, the substance to be tested is referred to herein as an analyte, irrespective of its status otherwise as an antigen or antibody, and proteins which bind to the analyte are denominated binding partners, whether they be antibodies, cell surface receptors or antigens.

Analytical methods for NT-4 or its antibodies all use one or more of the following reagents: labelled analyte analogue, immobilized analyte analogue, labelled binding partner, immobilized binding partner and steric conjugates. The labelled reagents also are known as "tracers".

The label used is any detectable functionality which does not interfere with the binding of analyte and its binding partner. Numerous labels are known for use in immunoassay, examples including enzymes such as horseradish peroxidase, radioisotopes such as $^{14}$C and $^{131}$I, fluorophores such as rare earth chelates or fluorescein, stable free radicals and the like. Conventional methods are available to covalently bind these labels to proteins or polypeptides. Such bonding methods are suitable for use with NT-4 or its antibodies, all of which are proteinaceous.

Immobilization of reagents is required for certain assay methods. Immobilization entails separating the binding partner from any analyte which remains free in solution. This conventionally is accomplished by either insolubilizing the binding partner or analyte analogue before the assay procedure, as by adsorption to a water insoluble matrix or surface (Bennich, et al., U.S. Pat. No. 3,720,760), by covalent coupling (for example using glutaraldehyde cross-linking), or by insolubilizing the partner or analogue afterward, e.g., by immunoprecipitation.

Other assay methods, known as competitive or sandwich assays, are well established and widely used in the commercial diagnostics industry.

Competitive assays rely on the ability of a labelled analogue (the "tracer") to compete with the test sample analyte for a limited number of binding sites on a common binding partner. The binding partner generally is insolubilized before or after the competition and then the tracer and analyte bound to the binding partner are separated from the unbound tracer and analyte. This separation is accomplished by decanting (where the binding partner was preinsolubilized) or by centrifuging (where the binding partner was precipitated after the competitive reaction). The amount of test sample analyte is inversely proportional to the amount of bound tracer as measured by the amount of marker substance. Dose-response curves with known amounts of analyte are prepared and compared with the test results in order to quantitatively determine the amount of analyte present in the test sample. These assays are called ELISA systems when enzymes are used as the detectable markers.

Another species of competitive assay, called a "homogeneous" assay, does not require a phase separation. Here, a conjugate of an enzyme with the analyte is prepared and used such that when anti-analyte binds to the analyte the presence of the anti-analyte modifies the enzyme activity. In this case, NT-4 or its immunologically active fragments are conjugated with a bifunctional organic bridge to an enzyme such as peroxidase. Conjugates are selected for use with anti-NT-4 so that binding of the anti-NT-4 inhibits or potentiates the enzyme activity of the label. This method per se is widely practiced under the name of EMIT.

Steric conjugates are used in steric hindrance methods for homogeneous assay. These conjugates are synthesized by covalently linking a low molecular weight hapten to a small analyte so that antibody to hapten substantially is unable to bind the conjugate at the same time as anti-analyte. Under this assay procedure the analyte present in the test sample will bind anti-analyte, thereby allowing anti-hapten to bind the conjugate, resulting in a change in the character of the conjugate hapten, e.g., a change in fluorescence when the hapten is a fluorophore.

Sandwich assays particularly are useful for the determination of NT-4 or NT-4 antibodies. In sequential sandwich assays an immobilized binding partner is used to adsorb test sample analyte, the test sample is removed as by washing, the bound analyte is used to adsorb labelled binding partner and bound material then separated from residual tracer. The amount of bound tracer is directly proportional to test sample analyte. In "simultaneous" sandwich assays test sample is not separated before adding the labelled binding partner. A sequential sandwich assay using an anti-NT-4 monoclonal antibody as one antibody and a polyclonal anti-NT-4 antibody as the other is useful in testing samples for NT-4 activity.

The foregoing are merely exemplary diagnostic assays for NT-4 and antibodies. Other methods now or hereafter developed for the determination of these analytes are included within the scope hereof, including the bioassay described above.

The following examples are offered by way of illustration and not by way of limitation.

EXAMPLE I

Attempts to identify and isolate DNA encoding NT-4 from human genomic and cDNA libraries using NGF and BDNF probes were unsuccessful. Instead, to identify the NT-4 gene, it was necessary to amplify human genomic DNA using the polymerase chain reaction (PCR) (Mullis, et al., 1987, Cold Spring Harbor Symp. Quant. Biol. 51:263). Human genomic placental DNA (prepared as described in Maniatis, et al., 1982, *Molecular Cloning: A Laboratory Manual*, Cold Spring Harbor Laboratory, New York, in the section on preparing a genomic DNA library) was employed as template for the above-identified primers, since the active forms of NGF, BDNF, and NT-3 are encoded by a single exon (Leibrock, et al., supra; Hohn, et al., supra; Maisonpierre, et al., supra; Rosenthal, et al., supra).

Amino acid sequences for NGF, BDNF, and NT-3 were scanned for regions of common homology. A number of these regions were identified and single stranded primer pools containing restriction sites for Sal, Xba, and EcoRI were prepared that were complementary to all possible sequences of DNA for the plus and minus strands of the selected NGF, BDNF, and NT-3 sequences. The primer pool for the sense strand corresponded to residues 50–58 of (mature human βNGF) NGF, designated NGX-54. The sense primer comprised the following sequence of alternatives (SEQ ID NOS. 93, 94, 95 and 96, respectively):

```
5'-CCGCGCGCTCTAGAGTCGACAAGCAGTACTTCTATGAGACGAAGTGT-3'
              A  A  T   T TC  A   CCGA    C
                                          T
                                          A
```

The primer pool for the antisense strand corresponded to residues 102–110 of NGF (designated AR1) and comprised the following sequence of alternatives (SEQ ID NOS. 97, 98, 99 and 100, respectively):

```
5'-CGGCTCAGGGCCGAATTCGCACACGCAGGAAGTATCTATCCTTAT-3'
              A  T  A  CG  G   A   T GG
              G          T       G G A
              A
```

Note that each primer sequence has a restriction site at its 5' end in order to facilitate cloning the amplified sequences. Careful selection of amplification conditions allowed amplification of NT-4 sequence despite the fact that these pools were considerably larger than the conventional pools used heretofore for shorter amino acid sequences (ranging from 32 to 32,000 fold degeneracy. (Lee, et al., 1988, Science 239:1288; Strathmann, et al., 1989, Proc. Nat. Acad. Sci. 86:7407; Leibrock, et al. supra). The primers were employed to prepare amplified DNA which was then sequenced. The conditions for amplification were as follows:

I. PCR with Human genomic placental DNA
   denat. 95° C. 5' once initially
   denat. 95° C. 1' }
   anneal 55° C. 1' }45 cycles
   extens. 72° C. 1' }
   extens. 72° C. 15'
   10 μl 10x buffer (final=50 mM KCl, 10 mM Tris pH 8.4, 3.0 mM MgCl$_2$)
   3 μl human genomic DNA (3 μg)
   7.5 ng/μl primer (approx. 1 μg=~2.6 μM of 33 mer, therefore 10$^3$ degen=nM, 10$^6$=pM)
   7.5 ng/μl primer
   10 μl 10x of dNTPs (final=0.2 mM dNTPs)
   1 μl Taq polymerase
   61 μl dH$_2$O
   100 μl V$_T$ II. Cut with SalI and EcoRI, generate and gel purify fragments of the expected size, about 210 bp, and subclone into the M13-based vector, M13 mp 18 (Pharmacia).

NGF, BDNF, and NT-3 clones were identified by hybridization with oligonucleotides derived from unique regions of these respective cDNA sequences. Plasmids containing non-hybridizing inserts were sequenced (Smith, 1980, Meth. Enzymol. 65:560) and their potential translation products were analyzed for homology with NGF, BDNF, and NT-3.

This procedure revealed the presence of about 500 NGF, BDNF, and NT-3 clones, and 78 unrelated clones. In addition, three DNA fragments encoding part of a novel NGF-related factor were identified and collectively designated NT-4. The low abundance of NT-4 clones generated by PCR was caused by the poor homology between its DNA sequence and the PCR primers.

Screening of a human fetal brain cDNA library (Rosenthal, et al., 1987, EMBO J. 6:3641) using the genomic placental clone as a probe did not yield any positive clones. To obtain a complete human NT-4 homolog, a human genomic library was also screened (Maniatis, et al., 1978, Cell 15:687) and a 6-kb DNA fragment was isolated. This fragment was found to contain a single open reading frame encoding a polypeptide of 168 amino acids encompassing the NT-4 mature polypeptide.

The full nucleotide sequence and deduced amino acid sequence of human mature NT-4 and at least a portion of its precursor region is shown in FIG. 1. The entire precursor region, including the signal sequence, may be depicted between the initiating methionine shown and the last Arg of the cleavage site before the mature sequence begins. If this is the case, the precursor region of NT-4 is much shorter than the precursor regions of NGF, BDNF, and NT-3, shown in FIG. 2. Assignment of the initiation codon for NT-4 was made based on the location of the initiation codon in NGF, BDNF, and NT-3, and its mature amino acid sequence has 46.5%, 55.4%, and 52.2% sequence identity to mature NGF, BDNF, and NT-3, respectively, based on the BLAST or Fasta program. (See FIG. 2).

The active mature forms of NGF, BDNF, and NT-3 are homodimers of 13–14 kD proteins that are generated from their ca. 30 kD precursors (Leibrock, et al., supra; Maisonpierre, et al., supra; Hohn, et al., supra; Greene and Shooter, 1980, Ann Rev. Neurosci. 3:353). The NT-4 precursor protein sequence also showed a potential tetrabasic cleavage site before the mature region begins, indicating that all four members of this protein family may be similarly processed. Processing at this site would result in a 13.14 kD (130 amino acid) polypeptide.

To assess the possible function of NT-4, its tissue distribution was determined by Northern blot analysis. In the rat, NT-4 mRNA was found in varying levels in every tissue examined, i.e., heart, muscle, kidney, liver, spleen, gut, lung, and spinal cord, and in several brain regions, including cerebellum and cortex. This broad organ localization of NT-4 mRNA suggested that in the peripheral nervous system, NT-4 could serve as a target-derived trophic factor for sympathetic, sensory, and/or motor neurons. This theory is tested by expressing DNA encoding recombinant human NT-4 and assaying its various activities.

EXAMPLE II

The following protocol for expressing NT-4 DNA and purifying the resultant NT-4 is expected to provide sufficient NT-4 for assay purposes. This example also provides expected assays to be employed to test the purified NT-4 and compare it to NGF.

A cytomegalovirus-based expression vector called pRK5, described in Gorman, et al., 1990, DNA and Protein Engineering Techniques 2:1 and in EP Pub. No. 307,247, published Mar. 15, 1989, is employed as the expression vector. The NT-4 genomic DNA is cut from the phage in which it was cloned. This DNA fragment is then ligated into pRK5 previously cut with the appropriate restriction enzymes to accommodate the DNA fragment using standard ligation methodology (Maniatis et al., 1982, *Molecular Cloning: A Laboratory Manual*, Cold Spring Harbor Laboratory, New York). The resulting vector is called pRK-5hNT-4.

A human embryonal kidney 293 cell line (Graham, et al., 1977, J. Gen. Virol. 36:59) is grown to confluence. Ten μg of the NT-4 plasmid DNA (pRK-5hNT-4) is mixed with 1 μg of DNA encoding the VA RNA gene (Thimmappaya, et al., 1982, Cell 31:543) and dissolved in 500 μl of 1 mM Tris-HCl, 0.1 mM EDTA, 0.227 M CaCl$_2$. Added to this (dropwise while vortexing) is 500 μl of 50 mM HEPES (pH 7.35), 280 mM NaCl, 1.5 mM NaPO$_4$, and the precipitate is allowed to form for 10 min. at 25° C. The suspended precipitate is then added to the cells (in 100 mM plate) and allowed to settle for four hours in the incubator. The medium is then aspirated off and 2 ml of 20% glycerol in phosphate-buffered saline is added for 30 sec. The cells are washed twice with 5 ml of serum-free medium, then fresh medium is added, and the cells are incubated for five days.

The 293 cells are also transfected in the same way with pRK5 alone.

Twenty-four hours after the transfections, the medium is replaced and cells are incubated for 12 hours in the presence of 200 µCi/ml $^{36}$S-cysteine and 200 µCi $^{35}$S-methionine. Conditioned medium is then collected, concentrated 5-fold by lyophilization, and loaded on a 15% SDS gel, which is subsequently enhanced, dried, and exposed to film for two hours. These data are expected to indicate the presence of a polypeptide of approximately the expected size (14–15 kD).

Large-scale expression of NT-4 is performed by transiently introducing by the dextran sulfate method (Sompayrac and Danna, 1981, Proc. Natl. Acad. Sci. 12:7575) 700 µg of pRK-5hNT-4 into the human embryonal kidney 293 cell line grown to maximal density (1.5 liters) in a 3-liter Belco microcarrier spinner flask. The cells are first concentrated from the spinner flask by centrifugation, and washed with phosphate-buffered saline (PBS), and the DNA-dextran precipitate is incubated on the cell pellet for four hours. The cells are treated with 20% glycerol for 90 seconds, washed with a medium such as 50:50 DMEM: F-12 medium, and re-introduced into a 3-liter spinner flask containing 1.5 liter of the above medium plus 5 µg/ml bovine insulin and 0.1 µg/ml bovine transferrin. The above protocol is performed for three separate 3-liter cultures.

After 4 days approximately 5 liters of conditioned media from the large-scale expression described above is centrifuged and filtered to remove cells and debris, and concentrated 100-fold. The buffer, salts, and other small molecules are exchanged by dialysis into 25 mM sodium borate, pH 9.0, and 4 M urea, and applied to a 5 cm.×5 cm. DEAE Sepharose Fast-Flow ion-exchange chromatography column (Pharmacia, Inc.). The pH of column effluent (495 ml) is neutralized (pH 7.0) by the addition of 0.1 volume of 250 mM 3-(N-morpholino)propanesulfonic acid (MOPS) buffer to give a final composition of 25 mM MOPS, pH 7.0, and 4 M urea. This sample is applied to a 2.5 cm.×2.5 cm. S-Sepharose ion-exchange chromatography column (Pharmacia), washed, and eluted with 25 mM MOPS, pH 7.0, 4 M urea, and 0.5 M NaCl (40 ml).

Two different assays indicate the presence of recombinant human NT-4 in the S-Sepharose salt eluant (130 ng/ml, 5 µg total): 1) 48-hour neuronal survival and neurite outgrowth in three types of chick embryonal peripheral ganglionic neurons: paravertebral sympathetic chain ganglion neurons, spinal sensory neurons of dorsal root ganglia (lumbosacral region), and nodose ganglion neurons, and 2) immunocross-reactivity in an ELISA assay (Lucas, et al., 1989, J. Endocrinol. 120:449) utilizing polyclonal antibodies to human β-NGF, which can be generated as described above in the Description Section using β-NGF as immunogen rather than NT-4. The S-Sepharose eluant is dialyzed into 1 M acetic acid and 4 M urea, concentrated 10-fold, applied to a S-300 Sephacryl gel-filtration column (1.5 cm.×44 cm.), and chromatographed in the same buffer.

Aliquots of 200 µl are taken from each 1 ml fraction collected, dialyzed against 1 M acetic acid, lyophilized, and redissolved in 30 µl Laemmli SDS-PAGE sample buffer (Laemmli, 1970, Nature 227:680). Human β-NGF is obtained in a similar manner. Following SDS-PAGE, the silver-stained gel indicates a single, prominently stained polypeptide of approximately 15 kD. A 3-ml pool of S-300 column eluted fractions corresponding to this SDS-PAGE analyzed region is made, and 1 ml (0.5 nmole) is submitted to N-terminal amino acid sequence analysis by Edman degradation performed on a prototype automated amino acid sequencer (Kohr, EP Pat. Pub. No. 257,735). N-terminal sequence analysis gives a single sequence starting with a glycine residue predicted by the tetrabasic cleavage sequence ending in an arginine, and predicted by the processing of preproNGF to mature β-NGF.

The initial sequencing cycles may be quantitated to indicate the amount of recovery of the purified human NT-4 from the three-column process. The purified recombinant human NT-4 is dialyzed into 0.1% acetic acid to give a final concentration of 3.25 µg/ml. This stock material may be diluted into neuronal cell media (DMEM high glucose with 10% fetal bovine serum) at various concentrations from 4 to 60 ng/ml for carrying out various bioassays.

For larger-scale production of NT-4, the preferred vector is a SV40-driven vector such as pSVI6B described above, the preferred host cells are Chinese hamster ovary cells, and the preferred culture medium is a DMEM or 1:1 DMEM: F12 medium with levels of glucose elevated to optimize product yield or the serum-free medium described in U.S. Pat. No. 4,767,704.

Purified NT-4 is analyzed for neurotrophic activities on several types of primary embryonal day-10 chick neurons as described by Davies, in Nerve Growth Factors, 1989, (R. A. Rush, Ed., John Wiley & Sons, Boston), pp. 95–109. Thus, paravertebral sympathetic chain ganglia (SG), dorsal root (lumbosacral) ganglia (DRG), and nodose ganglia (NG) are dissected from day-10 chick embryos. The neuronal cells are dispersed from the ganglia with trypsin or pancreatin (GIBCO) and preplated twice to reduce the number of non-neuronal cells. Cells are counted and seeded in a 96-well tissue culture plate that had been pretreated with polyornithine (500 µg/ml) and laminin (10 µg/ml). (Lindsay, et al., 1985, Dev. Biol. 112:319). The cell seeding numbers are SG and DRG, 4000 cells per well; NG, 2000 cells per well.

Purified mouse submaxillary gland β-NGF used in the assays is obtained from Biomedical Technologies, Inc. and dissolved in 0.1% acetic acid to a concentration of 10 µg/ml. Purified recombinant human NT-4 dialyzed into 0.1% acetic acid at a final concentration of 3.25 µg/ml is used. Cells are incubated with or without the factors for 48 hours and phase-bright cell bodies which had elaborated neurites 5x the length of the cell body are counted. Individual perikaryons can be counted in the cultures of DRG and NG neurons. However, the perikaryons of SG neurons aggregate and cell aggregates are scored. The cell survival at maximal response is approximately 20–40% for DRG and NG neurons, whereas SG neurons are likely higher since aggregates are scored. Four experiments are carried out utilizing each of NGF and NT-4.

NT-4 is expected to be most active on peripheral neurons. In vertebrates, peripheral neurons are derived from two distinct embryonic sources: the neural crest and the neural placodes (LeDouarin and Smith, 1988, Ann. Rev. Cell Biol. 4:375). Neural crest-derived cells give rise to neurons and to the supporting cells of the peripheral nervous system and the placode-derived cells give rise to some sensory cells and cranial neurons.

The neural crest-derived dorsal root sensory ganglia (DRG) cells project to the CNS and to peripheral tissues, and are dependent on neurotrophic factors derived from both targets. (Lindsay, et al., 1985, Dev. Biol. 112:319). This dual dependency is a possible mechanism to ensure the survival only of neurons that form all the appropriate connections. Placode-derived nodose sensory ganglia (NG), which are also dually connected and respond to the CNS factor BDNF, do not respond to the peripherally derived trophic factor (NGF). Thus, peripheral target innervation by NG neurons is likely to be ensured by an alternative mechanism or via other factors.

The presence of NT-4 in the brain and the periphery suggests additional functions and raises the possibility that it could be valuable for treating diseases such as alzheimer's, Parkinson's, or Huntington's chorea that are caused by brain neuron degeneration and/or treating damaged nerves due to trauma or preventing damage to peripheral nerve cells. NT-4 could be tested for central neurological functions in an established animal lesion model such as that of Hefti, supra, or in aged rats or monkeys.

EXAMPLE III

To identify naturally occurring amino acid sequence variants of NT-4, the genomic DNA fragment described above, comprising the coding sequence for mature human NT-4, was used as a hybridization probe to screen for homologous DNAs in the human fetal brain cDNA library (Rosenthal, et al., 1987, EMBO J., 6:3641) and in a human lymphocyte genomic DNA library (Stratagene, La Jolla, Calif.).

Hybridization and washing of filters containing the library DNAs were performed under high stringency conditions: Hybridization of radiolabelled NT-4 probe to the filters was performed in a solution of 50% formamide, 5x SSC (1x= 0.15 M NaCl, 0.015 M sodium citrate), 0.1% sodium dodecyl sulfate (SDS), 0.1% sodium pyrophosphate, 50 mM sodium phosphate pH 6.8, 2x Denhardt's solution (1x= 0.02% Ficoll, 0.02% polyvinylpyrrolidone, 0.02% bovine serum albumin), 10% dextran sulfate, at 42° C. for 20 hrs. Washing of the filters was performed in an aqueous solution of 0.1x SSC, 0.1% SDS at 42° C.

Three DNAs were identified that had significant sequence homology with the DNA encoding mature human NT-4. The complete nucleotide sequences of those homologous DNAs is shown in FIGS. 3, 4, and 5, along with the deduced amino acid sequence of the polypeptides they encode, which polypeptides are referred to as NT-4β, NT-4γ, and NT-4Δ, respectively. The DNA encoding human NT-4β, having the sequence shown in FIG. 3, was isolated from the human fetal brain cDNA library. The nucleotide sequence shown in FIG. 3 appears to encode a portion of human NT-4β. A full length cDNA, encoding the entirety of human NT-4β, is readily obtained by probing the human fetal brain cDNA library with the cDNA disclosed in FIG. 3. The DNA encoding human NT-4γ, having the sequence shown in FIG. 4, was isolated from the human lymphocyte genomic DNA library. The DNA encoding human NT-4Δ, having the sequence shown in FIG. 5, also was isolated from the human lymphocyte genomic DNA library.

Figure 6:
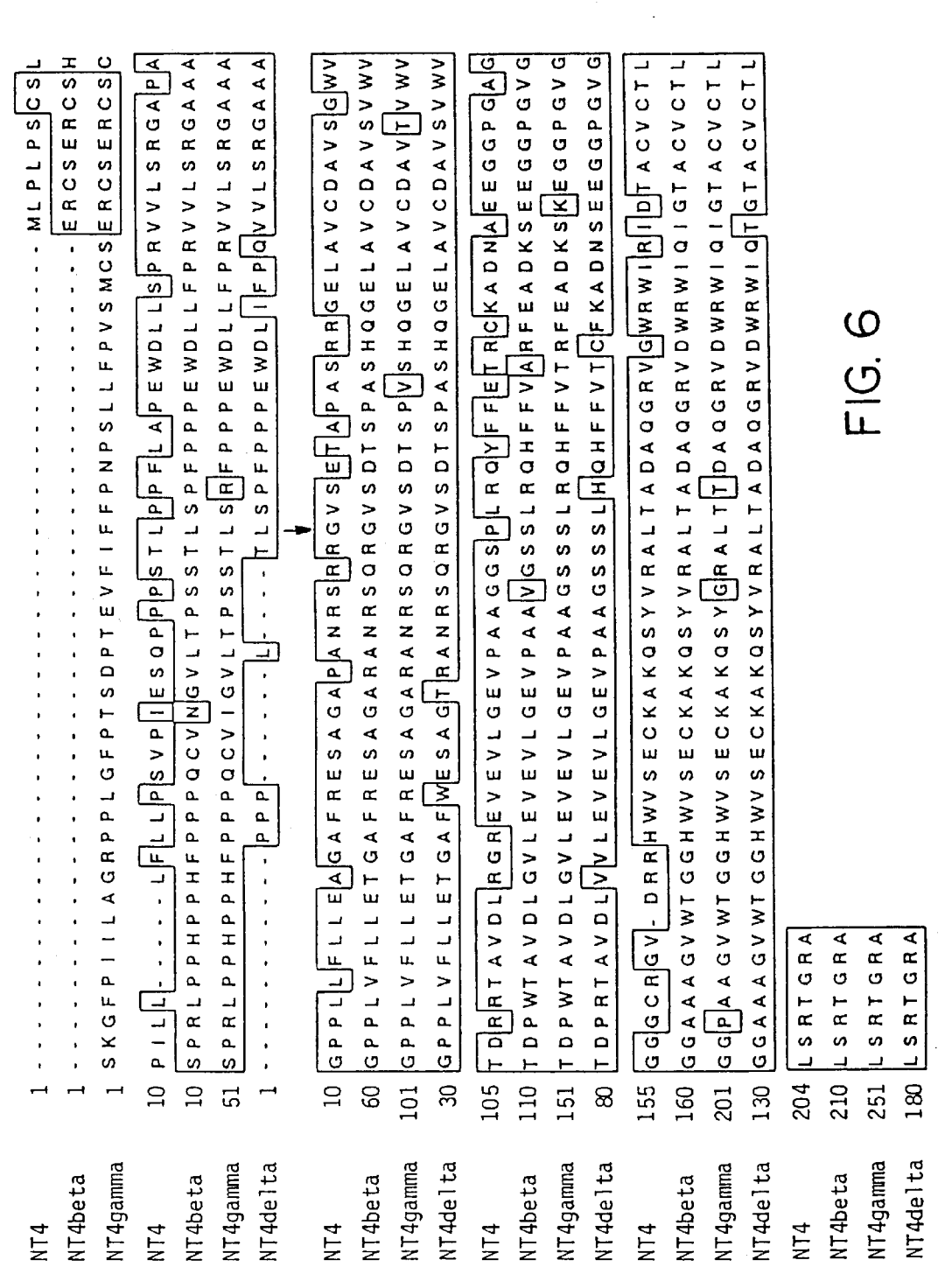

FIG. 6 shows the homologies among the amino acid sequences of human NT-4, NT-4β, NT-4γ, and NT-4Δ. The amino acid sequence of human NT-4 has at least about 75% sequence homology (identity) to each of NT-4β NT-4γ, and NT-4Δ, based on the alignment of the amino acid sequences as shown in FIG. 6. As is apparent, NT-4β, NT-4γ, and NT-4 Δ are amino acid sequence variants of human NT-4, as defined herein, differing from human NT-4 by virtue of various amino acid insertions, and substitutions.

Because of NT-4β, NT-4γ, and NT-4Δ are naturally occurring amino acid sequence variants of human NT-4, it is expected that NT-4β, NT-4γ, and NT-4Δ, like NT-4, have a role in regulating the normal growth and/or development of vertebrate neural tissue. NT-4β, NT-4γ, and NT-4Δ are readily produced by recombinant means by expression in a suitable host cell transformed with an expression vector comprising DNA encoding those polypeptides, as described above. NT-4β, NT-4γ, and NT-4Δ are analyzed for neurotrophic activities as described above for NT-4.

In summary, NT-4 is a novel trophic factor with a broad tissue distribution. It complements NGF, BDNF, and NT-3, which are trophic factors for some peripheral neurons. NT-4β, NT-4γ, and NT-4Δ are novel amino acid sequence variants of NT-4. Each of these factors can likely act alone or in concert on defined subsets of neurons to achieve the correct neuronal connections both in the peripheral and central nervous system.

What is claimed is:

1. An isolated nucleic acid comprising a nucleic acid sequence that encodes an amino acid sequence at least 75% homologous to the amino acid sequence for mature human NT-4 of SEQ ID NO.:2, and that hybridizes under stringent conditions to DNA having SEQ ID NO.:1 sequence encoding mature NT-4.

2. A vector comprising the nucleic acid of claim 1.

3. A host cell comprising the nucleic acid of claim 1.

4. A method for producing NT-4, comprising culturing the host cell of claim 3 and recovering NT-4 from the host cell culture.

5. The method of claim 4 wherein the NT-4 is recovered from the host cell culture medium.

6. A nucleic acid of claim 1 that is a naturally-occurring mammalian nucleic acid.

7. An isolated nucleic acid of claim 1, wherein the amino acid homology is greater than 85%.

8. An isolated acid of claim 1, wherein the nucleic acid sequence encodes an amino acid sequence of mature NT-4 of SEQ ID NO.:2 that is substituted at one to three amino acid positions.

9. An isolated nucleic acid of claim 8, wherein the amino acid sequence is substituted at a scrine protease cleavage site to prevent protease cleavage at that site.

10. An isolated nucleic acid of claim 8, wherein the amino acid sequence is substituted at a glycosylation site.

11. An isolated nucleic acid of claim 8, wherein at least one substitution is a conservative substitution.

12. The isolated nucleic acid of claim 1, encoding an amino acid sequence comprising an intrasequence insertion of 1 to 5 amino acids in the amino acid sequence of mature human NT-4 of SEQ ID NO:2.

13. The isolated nucleic acid of claim 12, wherein the encoded amino acid sequence comprises an intrasequence insertion of 1 to 3 amino acids.

14. The isolated nucleic acid of claim 1, encoding an amino acid sequence comprising a deletion of 1 to 10 amino acids in the amino acid sequence of mature human NT-4 of SEQ ID NO:2.

15. An isolated nucleic acid encoding neurotrophic factor 4 (NT-4) having the amino acid sequence depicted in any one of FIGS. 1, 3, 4 and 5 (SEQ ID NOS:2, 8, 10 and 12).

16. An isolated nucleic acid comprising, a nucleic acid sequence encoding an amino acid sequence of mature NT-4 of SEQ ID NO.:2 that is substituted at one amino acid position.

17. An isolated nucleic acid comprising a nucleotide sequence encoding mature NT-4β of FIG. 3 (SEQ ID NO:8), mature NT-4γ of FIG. 4 (SEQ ID NO:10), or mature NT-4Δ of FIG. 5 (SEQ ID NO:12).

18. An isolated nucleic acid comprising a nucleotide sequence encoding mature NT-4β of FIG. 3 (SEQ ID NO:8), mature NT-4γ of FIG. 4 (SEQ ID NO:10), or mature NT-4Δ of FIG. 5 (SEQ ID NO:12), wherein the amino acid sequence is substituted at one to three amino acid positions.

19. A vector comprising the nucleic acid of claim 16, 17 or 18.

20. A host cell comprising the vector of claim 19.

21. A method for producing NT-4, comprising culturing the host cell of claim 20 and recovering NT-4 from the host cell culture.

22. The method of claim 21 wherein the NT-4 is recovered from the host cell culture medium.

23. An isolated nucleic acid of claim 17 comprising the nucleotide sequence shown in FIG. 3 (SEQ ID NO:7) for mature human NT-4β.

24. An isolated nucleic acid of claim 17 comprising the nucleic acid sequence shown in FIG. 4 (SEQ ID NO:9) for mature human NT-4γ.

25. An isolated nucleic acid of claim 17 comprising the nucleotide sequence shown in FIG. 5 (SEQ ID NO:11) for mature human NT-4Δ.

26. The nucleic acid of claim 18, wherein the nucleic acid sequence encodes an amino acid sequence of mature NT-4 that is substituted at one position.

27. The nucleic acid of claim 18, wherein the amino acid sequence is substituted at a serine protease cleavage site to prevent protease cleavage at that site.

28. The nucleic acid of claim 18, wherein the amino acid sequence is substituted at a glycosylation site.

29. The nucleic acid of claim 18, wherein at least one substitution is a conservative substitution.

* * * * *